United States Patent
Van Leeuwen

(10) Patent No.: US 10,808,235 B2
(45) Date of Patent: Oct. 20, 2020

(54) BETA-GLUCOSIDASE AND USES THEREOF

(71) Applicant: DSM IP ASSETS B.V., Heerlen (NL)

(72) Inventor: Johannes Gustaaf Ernst Van Leeuwen, Echt (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 15/781,857

(22) PCT Filed: Dec. 8, 2016

(86) PCT No.: PCT/EP2016/080240
§ 371 (c)(1),
(2) Date: Jun. 6, 2018

(87) PCT Pub. No.: WO2017/097895
PCT Pub. Date: Jun. 15, 2017

(65) Prior Publication Data
US 2018/0362945 A1    Dec. 20, 2018

(30) Foreign Application Priority Data

| Dec. 10, 2015 | (EP) | 15198788 |
| Dec. 10, 2015 | (EP) | 15198826 |
| Dec. 10, 2015 | (EP) | 15198893 |
| Dec. 10, 2015 | (EP) | 15198902 |

(51) Int. Cl.
| C12N 9/34 | (2006.01) |
| C12N 9/42 | (2006.01) |
| C12P 19/14 | (2006.01) |
| C12P 19/02 | (2006.01) |
| C12N 15/80 | (2006.01) |

(52) U.S. Cl.
CPC .......... *C12N 9/2428* (2013.01); *C12N 9/2437* (2013.01); *C12N 9/2445* (2013.01); *C12P 19/02* (2013.01); *C12P 19/14* (2013.01); *C12N 15/80* (2013.01); *C12Y 302/01003* (2013.01)

(58) Field of Classification Search
CPC ........ C12P 19/02; C12P 19/14; C12N 9/2445; C12N 15/18; C12Y 302/01003
USPC ................. 435/209, 69.1, 105, 200
See application file for complete search history.

(56) References Cited

U.S. PATENT DOCUMENTS 9,441,214 B2    9/2016 Schoonneveld-Bergmans et al.

FOREIGN PATENT DOCUMENTS

| WO | 2011/063308 A2 | 5/2011 |
| WO | 2012/000890 A1 | 1/2012 |
| WO | 2013/028928 A1 | 2/2013 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Zong, Zhiyou et al., "Computer-Assisted Rational Modifications to Improve the Thermostability of β-Glucosidase from Penicillium piceum H16", Bioenergy Research, Mar. 15, 2015, pp. 1384-1390, vol. 8, No. 3, Springer US, Boson, US.
International Search Report of International Patent Application No. PCT/EP2016/080240 dated Mar. 6, 2017.

* cited by examiner

*Primary Examiner* — Robert B Mondesi
*Assistant Examiner* — Mohammad Y Meah
(74) *Attorney, Agent, or Firm* — McBee Moore & Vanik IP, LLC

(57) ABSTRACT

The application relates to a polypeptide having beta-glucosidase activity, its method of production and its uses.

8 Claims, 1 Drawing Sheet
Specification includes a Sequence Listing.

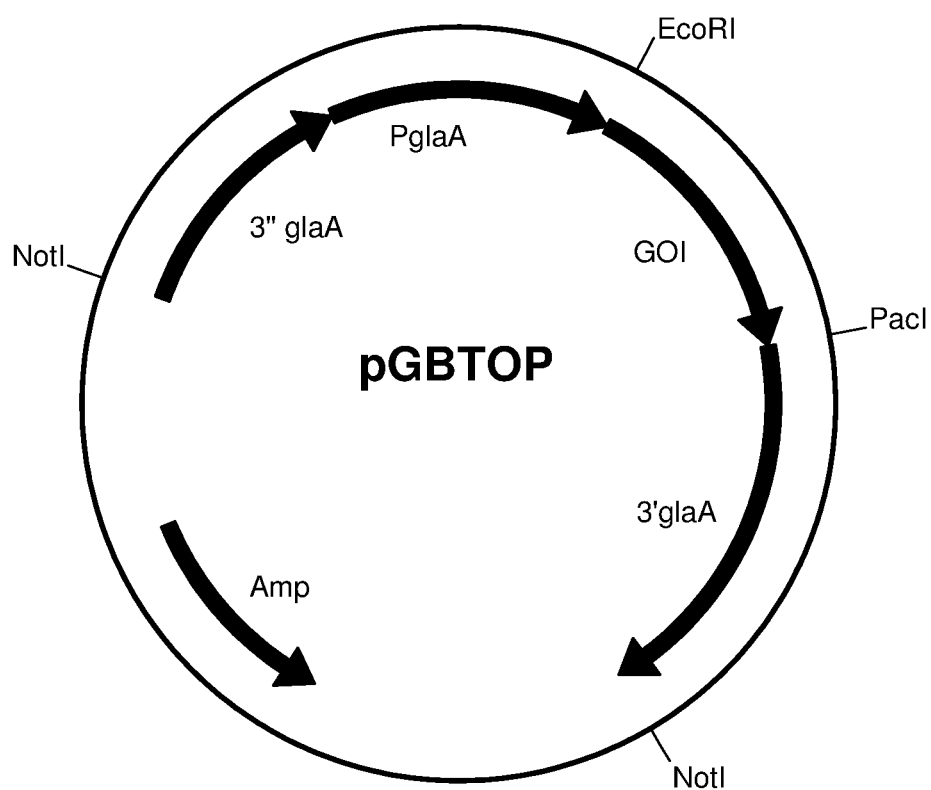

SEQUENCE LISTING

<160> NUMBER OF SEQ ID NOS: 4

<210> SEQ ID NO 1
<211> LENGTH: 2574
<212> TYPE: DNA
<213> ORGANISM: Talaromyces emersonii
<220> FEATURE:
<221> NAME/KEY: CDS
<222> LOCATION: (1)..(2574)

<400> SEQUENCE: 1

| | | | | | | | | | | | | | | | | |
|---|---|---|---|---|---|---|---|---|---|---|---|---|---|---|---|---|
| atg | cgc | aac | ggt | ctg | ctc | aag | gtt | gct | gct | ctt | gct | gct | gcc | tcc | gcc | 48 |
| Met | Arg | Asn | Gly | Leu | Leu | Lys | Val | Ala | Ala | Leu | Ala | Ala | Ala | Ser | Ala | |
| 1 | | | | 5 | | | | | 10 | | | | | 15 | | |

| gtc | aac | ggc | gag | aac | ctg | gcc | tac | tct | cct | ccc | ttc | tac | ccc | tcc | ccc | 96 |
|---|---|---|---|---|---|---|---|---|---|---|---|---|---|---|---|---|
| Val | Asn | Gly | Glu | Asn | Leu | Ala | Tyr | Ser | Pro | Pro | Phe | Tyr | Pro | Ser | Pro | |
| | | | 20 | | | | | 25 | | | | | 30 | | | |

| tgg | gcc | aac | ggc | cag | ggt | gac | tgg | gct | gag | gcc | tac | cag | aag | gcc | gtc | 144 |
|---|---|---|---|---|---|---|---|---|---|---|---|---|---|---|---|---|
| Trp | Ala | Asn | Gly | Gln | Gly | Asp | Trp | Ala | Glu | Ala | Tyr | Gln | Lys | Ala | Val | |
| | | 35 | | | | | 40 | | | | | 45 | | | | |

| cag | ttc | gtc | agc | cag | ctc | acc | ctg | gct | gag | aag | gtc | aac | ctg | acc | act | 192 |
|---|---|---|---|---|---|---|---|---|---|---|---|---|---|---|---|---|
| Gln | Phe | Val | Ser | Gln | Leu | Thr | Leu | Ala | Glu | Lys | Val | Asn | Leu | Thr | Thr | |
| 50 | | | | | 55 | | | | | 60 | | | | | | |

| ggt | act | ggc | tgg | gag | cag | gac | cgc | tgc | gtt | ggc | cag | gtc | ggc | tcc | atc | 240 |
|---|---|---|---|---|---|---|---|---|---|---|---|---|---|---|---|---|
| Gly | Thr | Gly | Trp | Glu | Gln | Asp | Arg | Cys | Val | Gly | Gln | Val | Gly | Ser | Ile | |
| 65 | | | | | 70 | | | | | 75 | | | | | 80 | |

| ccc | cgt | ctt | ggt | ttc | ccc | ggt | ctt | tgc | atg | cag | gac | tct | cct | ctt | ggt | 288 |
|---|---|---|---|---|---|---|---|---|---|---|---|---|---|---|---|---|
| Pro | Arg | Leu | Gly | Phe | Pro | Gly | Leu | Cys | Met | Gln | Asp | Ser | Pro | Leu | Gly | |
| | | | | 85 | | | | | 90 | | | | | 95 | | |

| gtc | cgt | gac | acc | gac | tac | aac | tct | gct | ttc | cct | gct | ggt | gtc | aac | gtc | 336 |
|---|---|---|---|---|---|---|---|---|---|---|---|---|---|---|---|---|
| Val | Arg | Asp | Thr | Asp | Tyr | Asn | Ser | Ala | Phe | Pro | Ala | Gly | Val | Asn | Val | |
| | | | 100 | | | | | 105 | | | | | 110 | | | |

| gct | gcc | acc | tgg | gac | cgc | aac | ctg | gcc | tac | cgc | cgt | ggt | gtt | gcc | atg | 384 |
|---|---|---|---|---|---|---|---|---|---|---|---|---|---|---|---|---|
| Ala | Ala | Thr | Trp | Asp | Arg | Asn | Leu | Ala | Tyr | Arg | Arg | Gly | Val | Ala | Met | |
| | | 115 | | | | | 120 | | | | | 125 | | | | |

| ggt | gag | gag | cac | cgt | ggc | aag | ggt | gtt | gat | gtc | cag | ctc | ggt | cct | gtt | 432 |
|---|---|---|---|---|---|---|---|---|---|---|---|---|---|---|---|---|
| Gly | Glu | Glu | His | Arg | Gly | Lys | Gly | Val | Asp | Val | Gln | Leu | Gly | Pro | Val | |
| 130 | | | | | 135 | | | | | 140 | | | | | | |

| gct | ggt | cct | ctg | ggc | cgc | tct | ccc | gat | gct | ggc | cgc | aac | tgg | gag | ggt | 480 |
|---|---|---|---|---|---|---|---|---|---|---|---|---|---|---|---|---|
| Ala | Gly | Pro | Leu | Gly | Arg | Ser | Pro | Asp | Ala | Gly | Arg | Asn | Trp | Glu | Gly | |
| 145 | | | | | 150 | | | | | 155 | | | | | 160 | |

| ttc | gct | cct | gac | ccc | gtc | ctc | act | ggt | aac | atg | atg | gcc | tcc | acc | atc | 528 |
|---|---|---|---|---|---|---|---|---|---|---|---|---|---|---|---|---|
| Phe | Ala | Pro | Asp | Pro | Val | Leu | Thr | Gly | Asn | Met | Met | Ala | Ser | Thr | Ile | |
| | | | | 165 | | | | | 170 | | | | | 175 | | |

| cag | ggt | atc | cag | gat | gct | ggt | gtc | att | gcc | tgc | gcc | aag | cac | ttc | atc | 576 |
|---|---|---|---|---|---|---|---|---|---|---|---|---|---|---|---|---|
| Gln | Gly | Ile | Gln | Asp | Ala | Gly | Val | Ile | Ala | Cys | Ala | Lys | His | Phe | Ile | |
| | | | 180 | | | | | 185 | | | | | 190 | | | |

| ctg | tac | gag | cag | gag | cac | ttc | cgc | cag | ggt | gct | cag | gat | ggc | tac | gat | 624 |
|---|---|---|---|---|---|---|---|---|---|---|---|---|---|---|---|---|
| Leu | Tyr | Glu | Gln | Glu | His | Phe | Arg | Gln | Gly | Ala | Gln | Asp | Gly | Tyr | Asp | |
| | | 195 | | | | | 200 | | | | | 205 | | | | |

| ata | tct | gac | tcc | atc | tcc | gcc | aac | gcc | gat | gac | aag | acc | atg | cac | gag | 672 |
|---|---|---|---|---|---|---|---|---|---|---|---|---|---|---|---|---|
| Ile | Ser | Asp | Ser | Ile | Ser | Ala | Asn | Ala | Asp | Asp | Lys | Thr | Met | His | Glu | |
| 210 | | | | | 215 | | | | | 220 | | | | | | |

| ctc | tac | ctc | tgg | ccc | ttc | gcc | gat | gcc | gtc | cgt | gct | ggt | gtt | ggc | tcc | 720 |
|---|---|---|---|---|---|---|---|---|---|---|---|---|---|---|---|---|
| Leu | Tyr | Leu | Trp | Pro | Phe | Ala | Asp | Ala | Val | Arg | Ala | Gly | Val | Gly | Ser | |
| 225 | | | | | 230 | | | | | 235 | | | | | 240 | |

| gtc | atg | tgc | tcc | tac | aac | cag | gtc | aac | aac | tcc | tac | gcc | tgc | tcc | aac | 768 |
|---|---|---|---|---|---|---|---|---|---|---|---|---|---|---|---|---|
| Val | Met | Cys | Ser | Tyr | Asn | Gln | Val | Asn | Asn | Ser | Tyr | Ala | Cys | Ser | Asn | |
| | | | | 245 | | | | | 250 | | | | | 255 | | |

| agc | tac | acc | atg | aac | aag | ctc | ttg | aaa | tca | gag | ctt | ggt | ttc | cag | ggt | 816 |
|---|---|---|---|---|---|---|---|---|---|---|---|---|---|---|---|---|
| Ser | Tyr | Thr | Met | Asn | Lys | Leu | Leu | Lys | Ser | Glu | Leu | Gly | Phe | Gln | Gly | |

-continued

| | | |
|---|---|---|
| ttc gtc atg act gac tgg ggt ggt cac cac tct ggt gtt ggt tcc gct<br>Phe Val Met Thr Asp Trp Gly Gly His His Ser Gly Val Gly Ser Ala<br>          275                    280                    285 | 864 |

Columns: 260, 265, 270

```
ttc gtc atg act gac tgg ggt ggt cac cac tct ggt gtt ggt tcc gct      864
Phe Val Met Thr Asp Trp Gly Gly His His Ser Gly Val Gly Ser Ala
            275                 280                 285 ctt gct ggt ctt gac atg agc atg ccc ggt gac att gct ttc gac tcc      912
Leu Ala Gly Leu Asp Met Ser Met Pro Gly Asp Ile Ala Phe Asp Ser
        290                 295                 300 ggt acc tcc ttc tgg ggt acc aac ctg acc gtt gcc gtc ctc aac ggc      960
Gly Thr Ser Phe Trp Gly Thr Asn Leu Thr Val Ala Val Leu Asn Gly
305                 310                 315                 320 agc atc ccc gaa tgg cgt gtc gat gac atg gcc gtc cgt atc atg tct     1008
Ser Ile Pro Glu Trp Arg Val Asp Asp Met Ala Val Arg Ile Met Ser
            325                 330                 335 gcc tac tac aag gtc ggt cgt gac cgc tac tcc gtc ccc atc aac ttc     1056
Ala Tyr Tyr Lys Val Gly Arg Asp Arg Tyr Ser Val Pro Ile Asn Phe
        340                 345                 350 gac agc tgg acc ctc gac acc tac ggc cct gag cac tac gcc gtc ggc     1104
Asp Ser Trp Thr Leu Asp Thr Tyr Gly Pro Glu His Tyr Ala Val Gly
            355                 360                 365 cag ggt cag acc aag atc aac gag cac gtt gat gtc cgt ggc aac cac     1152
Gln Gly Gln Thr Lys Ile Asn Glu His Val Asp Val Arg Gly Asn His
370                 375                 380 gct gag atc atc cac gag atc ggt gct gcc tcc gcc gtc ctc ctc aag     1200
Ala Glu Ile Ile His Glu Ile Gly Ala Ala Ser Ala Val Leu Leu Lys
385                 390                 395                 400 aac aag ggt ggt ctg ccc ttg act ggt act gag cgc ttc gtc ggt gtg     1248
Asn Lys Gly Gly Leu Pro Leu Thr Gly Thr Glu Arg Phe Val Gly Val
            405                 410                 415 ttc ggc aag gat gcc ggt tcc aac ccc tgg ggt gtc aac ggc tgc tcc     1296
Phe Gly Lys Asp Ala Gly Ser Asn Pro Trp Gly Val Asn Gly Cys Ser
        420                 425                 430 gac cgt ggc tgc gac aac ggc acc ctc gcc atg ggc tgg ggc agc ggt     1344
Asp Arg Gly Cys Asp Asn Gly Thr Leu Ala Met Gly Trp Gly Ser Gly
            435                 440                 445 act gcc aac ttc ccc tac ctg gtc acc ccc gag cag gcc atc cag cgt     1392
Thr Ala Asn Phe Pro Tyr Leu Val Thr Pro Glu Gln Ala Ile Gln Arg
450                 455                 460 gag gtc ctt tct cgc aac ggc acc ttc act ggt atc acc gac aac ggt     1440
Glu Val Leu Ser Arg Asn Gly Thr Phe Thr Gly Ile Thr Asp Asn Gly
465                 470                 475                 480 gct ctt gct gag atg gct gct gct gcc tcc cag gcc gac acc tgc ctg     1488
Ala Leu Ala Glu Met Ala Ala Ala Ala Ser Gln Ala Asp Thr Cys Leu
            485                 490                 495 gtc ttt gcc aac gcc gac agc ggt gag ggc tac atc acc gtt gac ggc     1536
Val Phe Ala Asn Ala Asp Ser Gly Glu Gly Tyr Ile Thr Val Asp Gly
        500                 505                 510 aac gag ggt gac cgc aag aac ctg acc ctc tgg cag ggt gcc gac cag     1584
Asn Glu Gly Asp Arg Lys Asn Leu Thr Leu Trp Gln Gly Ala Asp Gln
            515                 520                 525 gtc atc cac aac gtt tcc gcc aac tgc aac aac act gtt gtt gtc ctc     1632
Val Ile His Asn Val Ser Ala Asn Cys Asn Asn Thr Val Val Val Leu
530                 535                 540 cac acc gtc ggt cct gtc ctg att gat gac tgg tac gac cac ccc aac     1680
His Thr Val Gly Pro Val Leu Ile Asp Asp Trp Tyr Asp His Pro Asn
545                 550                 555                 560 gtc act gcc atc ctc tgg gct ggt ctg ccc ggt cag gag tcc ggc aac     1728
Val Thr Ala Ile Leu Trp Ala Gly Leu Pro Gly Gln Glu Ser Gly Asn
            565                 570                 575 tcg cta gtt gat gtc ctc tac ggc cgt gtc aac ccc ggc aag act ccc     1776
```

| | | | | | | | | | | | | | | | | |
|---|---|---|---|---|---|---|---|---|---|---|---|---|---|---|---|---|
| Ser | Leu | Val | Asp | Val | Leu | Tyr | Gly | Arg | Val | Asn | Pro | Gly | Lys | Thr | Pro | |
| | | | 580 | | | | 585 | | | | 590 | | | | | |

| ttc | acc | tgg | ggt | cgt | gct | cgt | gat | gac | tac | ggt | gct | cct | ctg | att | gtc | 1824 |
|---|---|---|---|---|---|---|---|---|---|---|---|---|---|---|---|---|
| Phe | Thr | Trp | Gly | Arg | Ala | Arg | Asp | Asp | Tyr | Gly | Ala | Pro | Leu | Ile | Val | |
| | | | 595 | | | | 600 | | | | 605 | | | | | |

| aag | ccc | aac | aac | ggc | aag | ggt | gct | cct | cag | cag | gac | ttc | acc | gag | ggt | 1872 |
|---|---|---|---|---|---|---|---|---|---|---|---|---|---|---|---|---|
| Lys | Pro | Asn | Asn | Gly | Lys | Gly | Ala | Pro | Gln | Gln | Asp | Phe | Thr | Glu | Gly | |
| | 610 | | | | | 615 | | | | | 620 | | | | | |

| atc | ttc | att | gac | tac | cgc | cgc | ttc | gac | aag | tac | aac | atc | acc | ccc | atc | 1920 |
|---|---|---|---|---|---|---|---|---|---|---|---|---|---|---|---|---|
| Ile | Phe | Ile | Asp | Tyr | Arg | Arg | Phe | Asp | Lys | Tyr | Asn | Ile | Thr | Pro | Ile | |
| 625 | | | | | 630 | | | | | 635 | | | | | 640 | |

| tac | gag | ttc | ggt | ttc | ggt | ctg | agc | tac | acc | acc | ttc | gag | ttc | tcc | cag | 1968 |
|---|---|---|---|---|---|---|---|---|---|---|---|---|---|---|---|---|
| Tyr | Glu | Phe | Gly | Phe | Gly | Leu | Ser | Tyr | Thr | Thr | Phe | Glu | Phe | Ser | Gln | |
| | | | 645 | | | | 650 | | | | | 655 | | | | |

| ctc | aac | gtc | cag | ccc | atc | aac | gct | cct | ccc | tac | act | ccc | gcc | tcc | ggt | 2016 |
|---|---|---|---|---|---|---|---|---|---|---|---|---|---|---|---|---|
| Leu | Asn | Val | Gln | Pro | Ile | Asn | Ala | Pro | Pro | Tyr | Thr | Pro | Ala | Ser | Gly | |
| | | 660 | | | | | 665 | | | | | 670 | | | | |

| ttc | acc | aag | gct | gct | cag | tcc | ttc | ggc | cag | ccc | tcc | aac | gcc | tcc | gac | 2064 |
|---|---|---|---|---|---|---|---|---|---|---|---|---|---|---|---|---|
| Phe | Thr | Lys | Ala | Ala | Gln | Ser | Phe | Gly | Gln | Pro | Ser | Asn | Ala | Ser | Asp | |
| | 675 | | | | | 680 | | | | | 685 | | | | | |

| aac | ctc | tac | ccc | tcc | gac | att | gag | cgt | gtt | cct | ctg | tac | atc | tac | ccc | 2112 |
|---|---|---|---|---|---|---|---|---|---|---|---|---|---|---|---|---|
| Asn | Leu | Tyr | Pro | Ser | Asp | Ile | Glu | Arg | Val | Pro | Leu | Tyr | Ile | Tyr | Pro | |
| 690 | | | | | 695 | | | | | 700 | | | | | | |

| tgg | ctc | aac | agc | act | gac | ctc | aag | gcc | tct | gcc | aac | gac | ccc | gac | tac | 2160 |
|---|---|---|---|---|---|---|---|---|---|---|---|---|---|---|---|---|
| Trp | Leu | Asn | Ser | Thr | Asp | Leu | Lys | Ala | Ser | Ala | Asn | Asp | Pro | Asp | Tyr | |
| 705 | | | | | 710 | | | | | 715 | | | | | 720 | |

| ggc | ctt | cct | act | gag | aag | tac | gtg | cct | ccc | aac | gcc | acc | aac | ggt | gac | 2208 |
|---|---|---|---|---|---|---|---|---|---|---|---|---|---|---|---|---|
| Gly | Leu | Pro | Thr | Glu | Lys | Tyr | Val | Pro | Pro | Asn | Ala | Thr | Asn | Gly | Asp | |
| | | | 725 | | | | | 730 | | | | | 735 | | | |

| ccc | cag | ccc | att | gac | cct | gct | ggt | ggt | gct | cct | ggt | ggc | aac | ccc | tcc | 2256 |
|---|---|---|---|---|---|---|---|---|---|---|---|---|---|---|---|---|
| Pro | Gln | Pro | Ile | Asp | Pro | Ala | Gly | Gly | Ala | Pro | Gly | Gly | Asn | Pro | Ser | |
| | | | 740 | | | | | 745 | | | | | 750 | | | |

| ctc | tac | gag | cct | gtt | gct | cgt | gtc | acc | acc | atc | atc | acc | aac | act | ggc | 2304 |
|---|---|---|---|---|---|---|---|---|---|---|---|---|---|---|---|---|
| Leu | Tyr | Glu | Pro | Val | Ala | Arg | Val | Thr | Thr | Ile | Ile | Thr | Asn | Thr | Gly | |
| | | | 755 | | | | | 760 | | | | | 765 | | | |

| aag | gtc | act | ggt | gat | gag | gtt | cct | cag | ctc | tac | gtc | agc | ctt | ggt | ggt | 2352 |
|---|---|---|---|---|---|---|---|---|---|---|---|---|---|---|---|---|
| Lys | Val | Thr | Gly | Asp | Glu | Val | Pro | Gln | Leu | Tyr | Val | Ser | Leu | Gly | Gly | |
| 770 | | | | | 775 | | | | | 780 | | | | | | |

| ccc | gat | gat | gct | ccc | aag | gtc | ctc | cgt | ggt | ttc | gac | cgt | atc | acc | ctg | 2400 |
|---|---|---|---|---|---|---|---|---|---|---|---|---|---|---|---|---|
| Pro | Asp | Asp | Ala | Pro | Lys | Val | Leu | Arg | Gly | Phe | Asp | Arg | Ile | Thr | Leu | |
| 785 | | | | | 790 | | | | | 795 | | | | | 800 | |

| gct | cct | ggc | cag | cag | tac | ctc | tgg | acc | acc | acc | ctc | acc | cgc | cgt | gac | 2448 |
|---|---|---|---|---|---|---|---|---|---|---|---|---|---|---|---|---|
| Ala | Pro | Gly | Gln | Gln | Tyr | Leu | Trp | Thr | Thr | Thr | Leu | Thr | Arg | Arg | Asp | |
| | | | 805 | | | | | 810 | | | | | 815 | | | |

| atc | tcc | aac | tgg | gac | ccc | gtc | acc | cag | aac | tgg | gtt | gtc | acc | aac | tac | 2496 |
|---|---|---|---|---|---|---|---|---|---|---|---|---|---|---|---|---|
| Ile | Ser | Asn | Trp | Asp | Pro | Val | Thr | Gln | Asn | Trp | Val | Val | Thr | Asn | Tyr | |
| | | 820 | | | | | 825 | | | | | 830 | | | | |

| acc | aag | acc | atc | tac | gtc | ggc | aac | agc | tct | cgc | aac | ctg | ccc | ctc | cag | 2544 |
|---|---|---|---|---|---|---|---|---|---|---|---|---|---|---|---|---|
| Thr | Lys | Thr | Ile | Tyr | Val | Gly | Asn | Ser | Ser | Arg | Asn | Leu | Pro | Leu | Gln | |
| | 835 | | | | | 840 | | | | | 845 | | | | | |

| gct | cct | ctc | aag | ccc | tac | ccc | ggc | ata | taa | | | | | | | 2574 |
|---|---|---|---|---|---|---|---|---|---|---|---|---|---|---|---|---|
| Ala | Pro | Leu | Lys | Pro | Tyr | Pro | Gly | Ile | | | | | | | | |
| 850 | | | | | 855 | | | | | | | | | | | |

<210> SEQ ID NO 2
<211> LENGTH: 857
<212> TYPE: PRT
<213> ORGANISM: Talaromyces emersonii

<400> SEQUENCE: 2

```
Met Arg Asn Gly Leu Leu Lys Val Ala Ala Leu Ala Ala Ala Ser Ala
1               5                   10                  15

Val Asn Gly Glu Asn Leu Ala Tyr Ser Pro Pro Phe Tyr Pro Ser Pro
                20                  25                  30

Trp Ala Asn Gly Gln Gly Asp Trp Ala Glu Ala Tyr Gln Lys Ala Val
            35                  40                  45

Gln Phe Val Ser Gln Leu Thr Leu Ala Glu Lys Val Asn Leu Thr Thr
    50                  55                  60

Gly Thr Gly Trp Glu Gln Asp Arg Cys Val Gly Gln Val Gly Ser Ile
65                  70                  75                  80

Pro Arg Leu Gly Phe Pro Gly Leu Cys Met Gln Asp Ser Pro Leu Gly
                85                  90                  95

Val Arg Asp Thr Asp Tyr Asn Ser Ala Phe Pro Ala Gly Val Asn Val
                100                 105                 110

Ala Ala Thr Trp Asp Arg Asn Leu Ala Tyr Arg Arg Gly Val Ala Met
            115                 120                 125

Gly Glu Glu His Arg Gly Lys Gly Val Asp Val Gln Leu Gly Pro Val
130                 135                 140

Ala Gly Pro Leu Gly Arg Ser Pro Asp Ala Gly Arg Asn Trp Glu Gly
145                 150                 155                 160

Phe Ala Pro Asp Pro Val Leu Thr Gly Asn Met Met Ala Ser Thr Ile
                165                 170                 175

Gln Gly Ile Gln Asp Ala Gly Val Ile Ala Cys Ala Lys His Phe Ile
                180                 185                 190

Leu Tyr Glu Gln Glu His Phe Arg Gln Gly Ala Gln Asp Gly Tyr Asp
            195                 200                 205

Ile Ser Asp Ser Ile Ser Ala Asn Ala Asp Asp Lys Thr Met His Glu
            210                 215                 220

Leu Tyr Leu Trp Pro Phe Ala Asp Ala Val Arg Ala Gly Val Gly Ser
225                 230                 235                 240

Val Met Cys Ser Tyr Asn Gln Val Asn Asn Ser Tyr Ala Cys Ser Asn
                245                 250                 255

Ser Tyr Thr Met Asn Lys Leu Leu Lys Ser Glu Leu Gly Phe Gln Gly
                260                 265                 270

Phe Val Met Thr Asp Trp Gly His His Ser Gly Val Gly Ser Ala
                275                 280                 285

Leu Ala Gly Leu Asp Met Ser Met Pro Gly Asp Ile Ala Phe Asp Ser
290                 295                 300

Gly Thr Ser Phe Trp Gly Thr Asn Leu Thr Val Ala Val Leu Asn Gly
305                 310                 315                 320

Ser Ile Pro Glu Trp Arg Val Asp Asp Met Ala Val Arg Ile Met Ser
                325                 330                 335

Ala Tyr Tyr Lys Val Gly Arg Asp Arg Tyr Ser Val Pro Ile Asn Phe
                340                 345                 350

Asp Ser Trp Thr Leu Asp Thr Tyr Gly Pro Glu His Tyr Ala Val Gly
            355                 360                 365

Gln Gly Gln Thr Lys Ile Asn Glu His Val Asp Val Arg Gly Asn His
370                 375                 380

Ala Glu Ile Ile His Glu Ile Gly Ala Ala Ser Ala Val Leu Leu Lys
385                 390                 395                 400

Asn Lys Gly Gly Leu Pro Leu Thr Gly Thr Glu Arg Phe Val Gly Val
                405                 410                 415

Phe Gly Lys Asp Ala Gly Ser Asn Pro Trp Gly Val Asn Gly Cys Ser
```

-continued

```
                420                 425                 430
Asp Arg Gly Cys Asp Asn Gly Thr Leu Ala Met Gly Trp Gly Ser Gly
            435                 440                 445
Thr Ala Asn Phe Pro Tyr Leu Val Thr Pro Glu Gln Ala Ile Gln Arg
        450                 455                 460
Glu Val Leu Ser Arg Asn Gly Thr Phe Thr Gly Ile Thr Asp Asn Gly
465                 470                 475                 480
Ala Leu Ala Glu Met Ala Ala Ala Ser Gln Ala Asp Thr Cys Leu
                485                 490                 495
Val Phe Ala Asn Ala Asp Ser Gly Glu Gly Tyr Ile Thr Val Asp Gly
            500                 505                 510
Asn Glu Gly Asp Arg Lys Asn Leu Thr Leu Trp Gln Gly Ala Asp Gln
        515                 520                 525
Val Ile His Asn Val Ser Ala Asn Cys Asn Asn Thr Val Val Val Leu
    530                 535                 540
His Thr Val Gly Pro Val Leu Ile Asp Asp Trp Tyr Asp His Pro Asn
545                 550                 555                 560
Val Thr Ala Ile Leu Trp Ala Gly Leu Pro Gly Gln Glu Ser Gly Asn
                565                 570                 575
Ser Leu Val Asp Val Leu Tyr Gly Arg Val Asn Pro Gly Lys Thr Pro
            580                 585                 590
Phe Thr Trp Gly Arg Ala Arg Asp Asp Tyr Gly Ala Pro Leu Ile Val
        595                 600                 605
Lys Pro Asn Asn Gly Lys Gly Ala Pro Gln Gln Asp Phe Thr Glu Gly
    610                 615                 620
Ile Phe Ile Asp Tyr Arg Arg Phe Asp Lys Tyr Asn Ile Thr Pro Ile
625                 630                 635                 640
Tyr Glu Phe Gly Phe Gly Leu Ser Tyr Thr Thr Phe Glu Phe Ser Gln
                645                 650                 655
Leu Asn Val Gln Pro Ile Asn Ala Pro Pro Tyr Thr Pro Ala Ser Gly
            660                 665                 670
Phe Thr Lys Ala Ala Gln Ser Phe Gly Gln Pro Ser Asn Ala Ser Asp
        675                 680                 685
Asn Leu Tyr Pro Ser Asp Ile Glu Arg Val Pro Leu Tyr Ile Tyr Pro
    690                 695                 700
Trp Leu Asn Ser Thr Asp Leu Lys Ala Ser Ala Asn Asp Pro Asp Tyr
705                 710                 715                 720
Gly Leu Pro Thr Glu Lys Tyr Val Pro Pro Asn Ala Thr Asn Gly Asp
                725                 730                 735
Pro Gln Pro Ile Asp Pro Ala Gly Gly Ala Pro Gly Gly Asn Pro Ser
            740                 745                 750
Leu Tyr Glu Pro Val Ala Arg Val Thr Thr Ile Ile Thr Asn Thr Gly
        755                 760                 765
Lys Val Thr Gly Asp Glu Val Pro Gln Leu Tyr Val Ser Leu Gly Gly
    770                 775                 780
Pro Asp Asp Ala Pro Lys Val Leu Arg Gly Phe Asp Arg Ile Thr Leu
785                 790                 795                 800
Ala Pro Gly Gln Gln Tyr Leu Trp Thr Thr Thr Leu Thr Arg Arg Asp
                805                 810                 815
Ile Ser Asn Trp Asp Pro Val Thr Gln Asn Trp Val Val Thr Asn Tyr
            820                 825                 830
Thr Lys Thr Ile Tyr Val Gly Asn Ser Ser Arg Asn Leu Pro Leu Gln
        835                 840                 845
```

```
Ala Pro Leu Lys Pro Tyr Pro Gly Ile
    850             855

<210> SEQ ID NO 3
<211> LENGTH: 2577
<212> TYPE: DNA
<213> ORGANISM: Talaromyces emersonii
<220> FEATURE:
<221> NAME/KEY: CDS
<222> LOCATION: (1)..(2577)

<400> SEQUENCE: 3 atg agg aac ggg ttg ctc aag gtc gcc gcc ctt gcg gcc gct tcg gtc      48
Met Arg Asn Gly Leu Leu Lys Val Ala Ala Leu Ala Ala Ala Ser Val
1               5                   10                  15 gtc aat ggc gag aac ctg gct tat tca cct ccc ttc tac cct tcg ccg      96
Val Asn Gly Glu Asn Leu Ala Tyr Ser Pro Pro Phe Tyr Pro Ser Pro
            20                  25                  30 tgg gcc aat gga cag ggc gac tgg gca gag gcc tac gag aag gcc gtc     144
Trp Ala Asn Gly Gln Gly Asp Trp Ala Glu Ala Tyr Glu Lys Ala Val
        35                  40                  45 aag ttt gtc tcc caa ctc acg ctg gcc gaa aag gtc aac ctg acc acc     192
Lys Phe Val Ser Gln Leu Thr Leu Ala Glu Lys Val Asn Leu Thr Thr
    50                  55                  60 gga act ggt tgg gag cag gac cga tgc gtc ggc caa gtg ggt agc atc     240
Gly Thr Gly Trp Glu Gln Asp Arg Cys Val Gly Gln Val Gly Ser Ile
65                  70                  75                  80 cca aga ttg ggc ttc cca gga ctt tgc atg cag gac tct ccg ctg ggt     288
Pro Arg Leu Gly Phe Pro Gly Leu Cys Met Gln Asp Ser Pro Leu Gly
                85                  90                  95 gtt cga gac act gac tac aac tcg gcc ttc ccg gcg ggt gtc aat gtc     336
Val Arg Asp Thr Asp Tyr Asn Ser Ala Phe Pro Ala Gly Val Asn Val
            100                 105                 110 gct gct acc tgg aac agg gac ctc gcc tac cgt cgc ggc caa gcg atg     384
Ala Ala Thr Trp Asn Arg Asp Leu Ala Tyr Arg Arg Gly Gln Ala Met
        115                 120                 125 ggc gag gag cat cgc gga aaa ggt gtc gac gtt cag ctg ggc cct gtg     432
Gly Glu Glu His Arg Gly Lys Gly Val Asp Val Gln Leu Gly Pro Val
    130                 135                 140 gcc ggc ccg ctg ggc agg tct ccc gat gct ggc aga aac tgg gaa ggt     480
Ala Gly Pro Leu Gly Arg Ser Pro Asp Ala Gly Arg Asn Trp Glu Gly
145                 150                 155                 160 ttc gcc ccg gat ccc gtg ctg acc gga aac atg atg gcg tcc acc atc     528
Phe Ala Pro Asp Pro Val Leu Thr Gly Asn Met Met Ala Ser Thr Ile
                165                 170                 175 cag ggt att caa gat gct ggt gtc att gct tgc gcc aag cat ttc atc     576
Gln Gly Ile Gln Asp Ala Gly Val Ile Ala Cys Ala Lys His Phe Ile
            180                 185                 190 ctc tac gag cag gag cat ttc cgt cag ggc gct caa gat ggc tac gat     624
Leu Tyr Glu Gln Glu His Phe Arg Gln Gly Ala Gln Asp Gly Tyr Asp
        195                 200                 205 atc tcc gac agt atc agt gcc aac gcc gat gac aag act atg cac gag     672
Ile Ser Asp Ser Ile Ser Ala Asn Ala Asp Asp Lys Thr Met His Glu
    210                 215                 220 ttg tac ttg tgg cct ttt gcc gat gct gtt cgc gct ggc gtt ggt tca     720
Leu Tyr Leu Trp Pro Phe Ala Asp Ala Val Arg Ala Gly Val Gly Ser
225                 230                 235                 240 atc atg tgc tcc tac aac cag gtg aac aac agc tac gcc tgt tcc aac     768
Ile Met Cys Ser Tyr Asn Gln Val Asn Asn Ser Tyr Ala Cys Ser Asn
                245                 250                 255
```

```
agc tac acc atg aac aag ctg ctc aag agc gaa ttg ggc ttc caa ggc       816
Ser Tyr Thr Met Asn Lys Leu Leu Lys Ser Glu Leu Gly Phe Gln Gly
            260                 265                 270 ttc gtc atg acc gac tgg ggt ggc cac cac agt ggt gtg ggt tcc gct       864
Phe Val Met Thr Asp Trp Gly Gly His His Ser Gly Val Gly Ser Ala
            275                 280                 285 ctc gct ggt ttg gac atg tcg atg ccc gga gac att gcc ttc gac agt       912
Leu Ala Gly Leu Asp Met Ser Met Pro Gly Asp Ile Ala Phe Asp Ser
            290                 295                 300 ggc acc tcc ttc tgg ggc act aac ctc acg gtt gcc gtg ctc aat gga       960
Gly Thr Ser Phe Trp Gly Thr Asn Leu Thr Val Ala Val Leu Asn Gly
305                 310                 315                 320 agt gtt cct gag tgg cgt gtt gat gac atg gct gtc cgt atc atg tcc      1008
Ser Val Pro Glu Trp Arg Val Asp Asp Met Ala Val Arg Ile Met Ser
                325                 330                 335 gct tat tac aag gtc ggc cgc gac cgc tac agc gtc ccc atc aac ttt      1056
Ala Tyr Tyr Lys Val Gly Arg Asp Arg Tyr Ser Val Pro Ile Asn Phe
            340                 345                 350 gac tcg tgg acc ctg gat acc tat ggt ccc gag cac tat gcg gtg ggc      1104
Asp Ser Trp Thr Leu Asp Thr Tyr Gly Pro Glu His Tyr Ala Val Gly
            355                 360                 365 cag ggc aac acc aag atc aac gag cac gtt gat gtt cgc ggc aac cat      1152
Gln Gly Asn Thr Lys Ile Asn Glu His Val Asp Val Arg Gly Asn His
370                 375                 380 gca gaa atc atc cat gaa atc ggt gct gcc agc gcc gtc ctt ctc aag      1200
Ala Glu Ile Ile His Glu Ile Gly Ala Ala Ser Ala Val Leu Leu Lys
385                 390                 395                 400 aac aag ggt ggg ctt cct ttg act ggc acc gaa cgg ttt gtc ggt gtt      1248
Asn Lys Gly Gly Leu Pro Leu Thr Gly Thr Glu Arg Phe Val Gly Val
                405                 410                 415 ttc gga gag gat gcc gga tcc aac cct tgg ggt gtg aac ggc tgc agt      1296
Phe Gly Glu Asp Ala Gly Ser Asn Pro Trp Gly Val Asn Gly Cys Ser
            420                 425                 430 gac cga ggc tgc gac aat ggt aca ttg gcc atg ggc tgg ggc agt ggt      1344
Asp Arg Gly Cys Asp Asn Gly Thr Leu Ala Met Gly Trp Gly Ser Gly
            435                 440                 445 act gct aac ttc ccc tac ttg gtg acg ccg gag cag gcg atc gag aga      1392
Thr Ala Asn Phe Pro Tyr Leu Val Thr Pro Glu Gln Ala Ile Glu Arg
450                 455                 460 gaa gtc gtg tcc cga aat gga acc ttc acc gcc atc acg gac aat ggc      1440
Glu Val Val Ser Arg Asn Gly Thr Phe Thr Ala Ile Thr Asp Asn Gly
465                 470                 475                 480 gct ctt gag cag atg gcg gct gtc gcc tct cag gct gat gtt tgc ctg      1488
Ala Leu Glu Gln Met Ala Ala Val Ala Ser Gln Ala Asp Val Cys Leu
                485                 490                 495 gtc ttc gcc aac gcc gac tcc gga gaa ggc tac atc aac gtc gac ggc      1536
Val Phe Ala Asn Ala Asp Ser Gly Glu Gly Tyr Ile Asn Val Asp Gly
            500                 505                 510 aat gag ggt gac cgg aag aat ctg acc ctg tgg caa ggg gcg gat caa      1584
Asn Glu Gly Asp Arg Lys Asn Leu Thr Leu Trp Gln Gly Ala Asp Gln
            515                 520                 525 gtc atc cac aac gtc act gcc aac tgc aac aac acc gtc gtg gtg ttg      1632
Val Ile His Asn Val Thr Ala Asn Cys Asn Asn Thr Val Val Val Leu
530                 535                 540 cac act gtc ggc ccc gtt ttg atc gat gat tgg tat gac cac ccc aac      1680
His Thr Val Gly Pro Val Leu Ile Asp Asp Trp Tyr Asp His Pro Asn
545                 550                 555                 560 gtc act gcc att ctc tgg gct ggt ctt ccg ggc cag gag agc ggt aac      1728
Val Thr Ala Ile Leu Trp Ala Gly Leu Pro Gly Gln Glu Ser Gly Asn
                565                 570                 575
```

```
tcg ctc gtc gat gtc ctc tac ggc cgt gtc aac cct ggc gga aag act    1776
Ser Leu Val Asp Val Leu Tyr Gly Arg Val Asn Pro Gly Gly Lys Thr
            580                 585                 590 ccg ttc acc tgg gga cgg acc cgg gag gat tac ggt gct cct ctg gtc    1824
Pro Phe Thr Trp Gly Arg Thr Arg Glu Asp Tyr Gly Ala Pro Leu Val
        595                 600                 605 ctg aag ccg aac aat ggc aag ggc gcc ccg cag cag gac ttc act gag    1872
Leu Lys Pro Asn Asn Gly Lys Gly Ala Pro Gln Gln Asp Phe Thr Glu
    610                 615                 620 ggt atc ttc atc gac tac cgt cgg ttt gac aag tac aac atc acc ccc    1920
Gly Ile Phe Ile Asp Tyr Arg Arg Phe Asp Lys Tyr Asn Ile Thr Pro
625                 630                 635                 640 atc tac gaa ttc gga ttc ggt ctg agc tac act acc ttt gag ttt tct    1968
Ile Tyr Glu Phe Gly Phe Gly Leu Ser Tyr Thr Thr Phe Glu Phe Ser
            645                 650                 655 gag ctc aat gtg cag cct atc aat acg ccg ccg tac act ccc gct tct    2016
Glu Leu Asn Val Gln Pro Ile Asn Thr Pro Pro Tyr Thr Pro Ala Ser
        660                 665                 670 ggc ttc acc aag gcg gcg cag tca ttc ggc ccg tcg tcc aat gct tct    2064
Gly Phe Thr Lys Ala Ala Gln Ser Phe Gly Pro Ser Ser Asn Ala Ser
    675                 680                 685 gac aac ctg tac ccc agc gac att gag cgg gtc ccg ttg tac atc tac    2112
Asp Asn Leu Tyr Pro Ser Asp Ile Glu Arg Val Pro Leu Tyr Ile Tyr
690                 695                 700 cca tgg ctc aac tcc acc gat ttg aag gcg tcc gcc aat gac cct gac    2160
Pro Trp Leu Asn Ser Thr Asp Leu Lys Ala Ser Ala Asn Asp Pro Asp
705                 710                 715                 720 tat ggg ttg cct aac gac aaa tac gtt cct ccc aac gcc acg aac ggt    2208
Tyr Gly Leu Pro Asn Asp Lys Tyr Val Pro Pro Asn Ala Thr Asn Gly
            725                 730                 735 aac ccg cag ccc att aac ccg gct ggc ggt gct cct ggt ggc aac cct    2256
Asn Pro Gln Pro Ile Asn Pro Ala Gly Gly Ala Pro Gly Gly Asn Pro
        740                 745                 750 agt ctc tat gag cct gtt gct cgg gtc tca gcc atc atc acc aac acc    2304
Ser Leu Tyr Glu Pro Val Ala Arg Val Ser Ala Ile Ile Thr Asn Thr
    755                 760                 765 ggt aag gtt acg ggt gac gag gtt cct caa ctg tat gtc tct ctt ggc    2352
Gly Lys Val Thr Gly Asp Glu Val Pro Gln Leu Tyr Val Ser Leu Gly
770                 775                 780 ggt ccc gat gat gcc ccc aag gtt ctt cgt ggc ttc gac cgt atc aca    2400
Gly Pro Asp Asp Ala Pro Lys Val Leu Arg Gly Phe Asp Arg Ile Thr
785                 790                 795                 800 ctt gcg cct ggt cag cag acc ttg tgg acg acc acc ctg acg agg cga    2448
Leu Ala Pro Gly Gln Gln Thr Leu Trp Thr Thr Thr Leu Thr Arg Arg
            805                 810                 815 gac atc tcg aac tgg gac cct gtc acc cag aac tgg gtt gtg acc aac    2496
Asp Ile Ser Asn Trp Asp Pro Val Thr Gln Asn Trp Val Val Thr Asn
        820                 825                 830 tac acc aag acg gtg tat gtt ggc aac tcc tcc cgc aac ctg cct ttg    2544
Tyr Thr Lys Thr Val Tyr Val Gly Asn Ser Ser Arg Asn Leu Pro Leu
    835                 840                 845 cag gca ccc ctt aag cca tat cct gga atc taa                         2577
Gln Ala Pro Leu Lys Pro Tyr Pro Gly Ile
        850                 855

<210> SEQ ID NO 4
<211> LENGTH: 858
<212> TYPE: PRT
<213> ORGANISM: Talaromyces emersonii
```

```
<400> SEQUENCE: 4

Met Arg Asn Gly Leu Leu Lys Val Ala Ala Leu Ala Ala Ala Ser Val
1               5                   10                  15

Val Asn Gly Glu Asn Leu Ala Tyr Ser Pro Pro Phe Tyr Pro Ser Pro
            20                  25                  30

Trp Ala Asn Gly Gln Gly Asp Trp Ala Glu Ala Tyr Glu Lys Ala Val
        35                  40                  45

Lys Phe Val Ser Gln Leu Thr Leu Ala Glu Lys Val Asn Leu Thr Thr
    50                  55                  60

Gly Thr Gly Trp Glu Gln Asp Arg Cys Val Gly Gln Val Gly Ser Ile
65              70                  75                  80

Pro Arg Leu Gly Phe Pro Gly Leu Cys Met Gln Asp Ser Pro Leu Gly
            85                  90                  95

Val Arg Asp Thr Asp Tyr Asn Ser Ala Phe Pro Ala Gly Val Asn Val
            100                 105                 110

Ala Ala Thr Trp Asn Arg Asp Leu Ala Tyr Arg Arg Gly Gln Ala Met
            115                 120                 125

Gly Glu Glu His Arg Gly Lys Gly Val Asp Val Gln Leu Gly Pro Val
130                 135                 140

Ala Gly Pro Leu Gly Arg Ser Pro Asp Ala Gly Arg Asn Trp Glu Gly
145                 150                 155                 160

Phe Ala Pro Asp Pro Val Leu Thr Gly Asn Met Met Ala Ser Thr Ile
            165                 170                 175

Gln Gly Ile Gln Asp Ala Gly Val Ile Ala Cys Ala Lys His Phe Ile
            180                 185                 190

Leu Tyr Glu Gln Glu His Phe Arg Gln Gly Ala Gln Asp Gly Tyr Asp
    195                 200                 205

Ile Ser Asp Ser Ile Ser Ala Asn Ala Asp Asp Lys Thr Met His Glu
    210                 215                 220

Leu Tyr Leu Trp Pro Phe Ala Asp Ala Val Arg Ala Gly Val Gly Ser
225                 230                 235                 240

Ile Met Cys Ser Tyr Asn Gln Val Asn Asn Ser Tyr Ala Cys Ser Asn
            245                 250                 255

Ser Tyr Thr Met Asn Lys Leu Leu Lys Ser Glu Leu Gly Phe Gln Gly
            260                 265                 270

Phe Val Met Thr Asp Trp Gly His His Ser Gly Val Gly Ser Ala
            275                 280                 285

Leu Ala Gly Leu Asp Met Ser Met Pro Gly Asp Ile Ala Phe Asp Ser
    290                 295                 300

Gly Thr Ser Phe Trp Gly Thr Asn Leu Thr Val Ala Val Leu Asn Gly
305                 310                 315                 320

Ser Val Pro Glu Trp Arg Val Asp Asp Met Ala Val Arg Ile Met Ser
            325                 330                 335

Ala Tyr Tyr Lys Val Gly Arg Asp Arg Tyr Ser Val Pro Ile Asn Phe
            340                 345                 350

Asp Ser Trp Thr Leu Asp Thr Tyr Gly Pro Glu His Tyr Ala Val Gly
    355                 360                 365

Gln Gly Asn Thr Lys Ile Asn Glu His Val Asp Val Arg Gly Asn His
    370                 375                 380

Ala Glu Ile Ile His Glu Ile Gly Ala Ala Ser Ala Val Leu Leu Lys
385                 390                 395                 400

Asn Lys Gly Gly Leu Pro Leu Thr Gly Thr Glu Arg Phe Val Gly Val
            405                 410                 415
```

```
Phe Gly Glu Asp Ala Gly Ser Asn Pro Trp Gly Val Asn Gly Cys Ser
                420                 425                 430

Asp Arg Gly Cys Asp Asn Gly Thr Leu Ala Met Gly Trp Gly Ser Gly
            435                 440                 445

Thr Ala Asn Phe Pro Tyr Leu Val Thr Pro Glu Gln Ala Ile Glu Arg
        450                 455                 460

Glu Val Val Ser Arg Asn Gly Thr Phe Thr Ala Ile Thr Asp Asn Gly
465                 470                 475                 480

Ala Leu Glu Gln Met Ala Val Ala Ser Gln Ala Asp Val Cys Leu
                485                 490                 495

Val Phe Ala Asn Ala Asp Ser Gly Glu Gly Tyr Ile Asn Val Asp Gly
                500                 505                 510

Asn Glu Gly Asp Arg Lys Asn Leu Thr Leu Trp Gln Gly Ala Asp Gln
            515                 520                 525

Val Ile His Asn Val Thr Ala Asn Cys Asn Asn Thr Val Val Leu
    530                 535                 540

His Thr Val Gly Pro Val Leu Ile Asp Asp Trp Tyr Asp His Pro Asn
545                 550                 555                 560

Val Thr Ala Ile Leu Trp Ala Gly Leu Pro Gly Gln Glu Ser Gly Asn
                565                 570                 575

Ser Leu Val Asp Val Leu Tyr Gly Arg Val Asn Pro Gly Gly Lys Thr
            580                 585                 590

Pro Phe Thr Trp Gly Arg Thr Arg Glu Asp Tyr Gly Ala Pro Leu Val
        595                 600                 605

Leu Lys Pro Asn Asn Gly Lys Gly Ala Pro Gln Gln Asp Phe Thr Glu
    610                 615                 620

Gly Ile Phe Ile Asp Tyr Arg Arg Phe Asp Lys Tyr Asn Ile Thr Pro
625                 630                 635                 640

Ile Tyr Glu Phe Gly Phe Gly Leu Ser Tyr Thr Thr Phe Glu Phe Ser
                645                 650                 655

Glu Leu Asn Val Gln Pro Ile Asn Thr Pro Tyr Thr Pro Ala Ser
            660                 665                 670

Gly Phe Thr Lys Ala Ala Gln Ser Phe Gly Pro Ser Ser Asn Ala Ser
        675                 680                 685

Asp Asn Leu Tyr Pro Ser Asp Ile Glu Arg Val Pro Leu Tyr Ile Tyr
    690                 695                 700

Pro Trp Leu Asn Ser Thr Asp Leu Lys Ala Ser Ala Asn Asp Pro Asp
705                 710                 715                 720

Tyr Gly Leu Pro Asn Asp Lys Tyr Val Pro Pro Asn Ala Thr Asn Gly
                725                 730                 735

Asn Pro Gln Pro Ile Asn Pro Ala Gly Gly Ala Pro Gly Gly Asn Pro
            740                 745                 750

Ser Leu Tyr Glu Pro Val Ala Arg Val Ser Ala Ile Ile Thr Asn Thr
        755                 760                 765

Gly Lys Val Thr Gly Asp Glu Val Pro Gln Leu Tyr Val Ser Leu Gly
    770                 775                 780

Gly Pro Asp Asp Ala Pro Lys Val Leu Arg Gly Phe Asp Arg Ile Thr
785                 790                 795                 800

Leu Ala Pro Gly Gln Gln Thr Leu Trp Thr Thr Leu Thr Arg Arg
                805                 810                 815

Asp Ile Ser Asn Trp Asp Pro Val Thr Gln Asn Trp Val Thr Asn
                820                 825                 830
```

```
Tyr Thr Lys Thr Val Tyr Val Gly Asn Ser Ser Arg Asn Leu Pro Leu
        835             840             845

Gln Ala Pro Leu Lys Pro Tyr Pro Gly Ile
    850             855
```

BETA-GLUCOSIDASE AND USES THEREOF

CROSS-REFERENCE TO RELATED APPLICATIONS

This application is a National Stage entry of International Application No. PCT/EP2016/080240, filed 8 Dec. 2016, which claims priority to European Patent Application No. 15198788.0, filed 10 Dec. 2015, European Patent Application No. 15198826.8, filed 10 Dec. 2015, European Patent Application No. 15198902.7, filed 10 Dec. 2015, and European Patent Application No. 15198893.8, filed 10 Dec. 2015.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2919208-475000_ST25.txt" created on 4 Jun. 2018, and 40,245 bytes in size) is submitted concurrently with the instant application, and the entire contents of the Sequence Listing are incorporated herein by reference.

FIELD

The application relates to polypeptides having beta-glucosidase activity and polynucleotides encoding the polypeptides. Also included in the application are nucleic acid contructs, vectors and host cells comprising the polynucleotides. The application also relates to methods of producing the polypeptides as well as methods of using the polypeptides.

BACKGROUND

Carbohydrates constitute the most abundant organic compounds on earth. However, much of this carbohydrate is sequestered in complex polymers including starch and a collection of carbohydrates and lignin known as lignocellulose. The main carbohydrate components of lignocellulose are cellulose, hemicellulose and pectins. These complex polymers are often referred to collectively as lignocellulose.

Bioconversion of lignocellulosic biomass to a sugar that is subsequently fermented to produce alcohol as an alternative to liquid fuels has attracted an intensive attention of researchers since 1970s, when the oil crisis broke out because of decreasing output of petroleum by the OPEC. Ethanol has been widely used as a 10% blend to gasoline in the USA or as a neat fuel for vehicles in Brazil in the last two decades. More recently, the use of E85, an 85% ethanol blend has been implemented especially for clean city applications.

The importance of biofuel will increase in parallel with increases in prices for oil and the gradual depletion of its sources. Additionally, fermentable sugars are being used to produce plastics, polymers and other bio-based products and this industry is expected to grow substantially therefore increasing the demand for abundant low cost fermentable sugars which can be used as a feedstock in lieu of petroleum-based feedstocks.

The sequestration of large amounts of carbohydrates provides a plentiful source of potential energy in the form of sugars, both five carbon and six carbon sugars, which could be utilized for numerous industrial methods. However, the enormous energy potential of these carbohydrates is currently under-utilized, because the sugars are locked in complex polymers and hence are not readily accessible for fermentation.

Regardless of the type of cellulosic feedstock, the cost and hydrolytic efficiency of enzymes are major factors that restrict the commercialization of biomass bioconversion methods. The production costs of microbially produced enzymes are tightly connected with a productivity of the enzyme-producing strain, the specific activity of the enzymes, the mode of action of the enzyme and the final activity yield in the fermentation broth.

In spite of the continued research of the last few decades to understand enzymatic lignocellulosic biomass degradation and cellulase production, it remains desirable to develop new highly active cellulases.

The present application fulfils this need in that it provides new polypeptides comprising beta-glucosidase activity and polynucleoitdes encoding the polypeptides.

SUMMARY

The present application relates to a variant polypeptide comprising a substitution at one or more positions corresponding to positions 90, 103, 142, 335, 485 and 606 of the polypeptide of SEQ ID NO: 2. In an embodiment the variant polypeptide has beta-glucosidase activity.

The present application relates to a variant polypeptide as described herein, which is a variant of a parent polypeptide which has beta-glucosidase activity and which comprises at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the polypeptide of SEQ ID NO: 2.

The present application relates to a variant polypeptide as described herein, which comprises at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the polypeptide of SEQ ID NO: 2.

The present application relates to a variant polypeptide as described herein, wherein the position corresponding to position 90 of the polypeptide of SEQ ID NO: 2 is substituted to L. The present application relates to a variant polypeptide as described herein, wherein the position corresponding to position 103 of the polypeptide of SEQ ID NO: 2 is substituted to A. The present application relates to a variant polypeptide as described herein, wherein the position corresponding to position 142 of the polypeptide of SEQ ID NO: 2 is substituted to S. The present application relates to a variant polypeptide as described herein, wherein the position corresponding to position 335 of the polypeptide of SEQ ID NO: 2 is substituted to V. The present application relates to a variant polypeptide as described herein, wherein the position corresponding to position 485 of the polypeptide of SEQ ID NO: 2 is substituted to I. The present application relates to a variant polypeptide as described herein, wherein the position corresponding to position 606 of the polypeptide of SEQ ID NO: 2 is substituted to A. The present application also relates to a variant polypeptide as described herein, which comprises one or more of these substitutions.

The present application relates to a variant polypeptide as described herein, which comprises substitution M90L. The present application relates to a variant polypeptide as described herein, which comprises substitution N103A. The present application relates to a variant polypeptide as described herein, which comprises substitution G142S. The present application relates to a variant polypeptide as described herein, which comprises substitution M335V. The present application relates to a variant polypeptide as described herein, which comprises substitution M485I. The present application relates to a variant polypeptide as described herein, which comprises substitution L606A.

The present application also relates to a polynucleotide which encodes a variant polypeptide as described herein.

The present application also relates to a nucleic acid construct or vector comprising a polynucleotide as described herein.

The present application also relates to a host cell comprising a polynucleotide as described herein or a nucleic acid construct or a vector as described herein. The host cell may be a fungal cell.

The present application also relates to a method of producing a variant polypeptide as described herein, which method comprises the steps of (a) cultivating a host cell as described herein under conditions conducive to the production of the variant polypeptide, and (b) optionally, recovering the variant polypeptide.

The present application also relates to a composition comprising (i) a variant polypeptide as described herein, and (ii) a cellulase and/or a hemicellulase and/or a pectinase. The cellulase may be selected from the group consisting of a lytic polysaccharide monooxygenase, a cellobiohydrolase I, a cellobiohydrolase II, an endo-beta-1,4-glucanase, a beta-glucosidase and a beta-(1,3)(1,4)-glucanase or any combination thereof and the hemicellulase may be selected from the group consisting of an endoxylanase, a beta-xylosidase, an alpha-L-arabinofuranosidase, an alpha-D-glucuronidase, an acetyl-xylan esterase, a feruloyl esterase, a coumaroyl esterase, an alpha-galactosidase, a beta-galactosidase, a beta-mannanase, a beta-mannosidase or any combination thereof. The composition may be a whole fermentation broth.

The present application also relates to a method for the treatment of a substrate comprising cellulose and/or hemicellulose which method comprises the step of contacting the substrate with a variant polypeptide as described herein and/or a composition as described herein.

The present application also relates to a method of producing a fermentation product, which method comprises the steps of (a) treating a substrate using the method for the treatment of a substrate comprising cellulose and/or hemicellulose as described herein, and (b) fermenting the resulting material to produce the fermentation product.

BRIEF DESCRIPTION OF THE DRAWINGS

FIG. 1: Map of pGBTOP for expression of genes in *A. niger*. Depicted are the gene of interest (GOI) expressed from the glucoamylase promoter (PglaA). In addition, the glucoamylase flank (3'-glaA) of the expression cassette is depicted. In this application a gene of interest is the coding sequence of a polypeptide as described herein.

DETAILED DESCRIPTION

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The term "derived from" also includes the terms "originated from", "obtained from", "obtainable from", "isolated from", and "created from", generally indicates that one specified material find its origin in another specified material or has features that can be described with reference to another specified material. As used herein, a substance (e.g., a polynucleotide or polypeptide) "derived from" a microorganism preferably means that the substance is native to that microorganism.

The present application relates to a variant polypeptide comprising a substitution at one or more positions corresponding to positions 90, 103, 142, 335, 485 and 606 of the polypeptide of SEQ ID NO: 2. In an embodiment the variant polypeptide has beta-glucosidase activity. The present application relates to a variant polypeptide comprising a substitution at one or more positions corresponding to positions 90+335+485, 103, 142, and 606 of the polypeptide of SEQ ID NO: 2. In an embodiment the variant polypeptide has beta-glucosidase activity.

The present application relates to a variant polypeptide as described herein, which is a variant of a parent polypeptide which has beta-glucosidase activity and which comprises at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the polypeptide of SEQ ID NO: 2.

The present application relates to a variant polypeptide as described herein, which comprises at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the polypeptide of SEQ ID NO: 2. In an embodiment the variant polypeptide as described herein comprises less than 100% sequence identity to to the polypeptide of SEQ ID NO: 2.

The present application relates to a variant polypeptide as described herein, wherein the position corresponding to position 90 of the polypeptide of SEQ ID NO: 2 is substituted to L. The present application relates to a variant polypeptide as described herein, wherein the position corresponding to position 103 of the polypeptide of SEQ ID NO: 2 is substituted to A. The present application relates to a variant polypeptide as described herein, wherein the position corresponding to position 142 of the polypeptide of SEQ ID NO: 2 is substituted to S. The present application relates to a variant polypeptide as described herein, wherein the position corresponding to position 335 of the polypeptide of SEQ ID NO: 2 is substituted to V. The present application relates to a variant polypeptide as described herein, wherein the position corresponding to position 485 of the polypeptide of SEQ ID NO: 2 is substituted to I. The present application relates to a variant polypeptide as described herein, wherein the position corresponding to position 606 of the polypeptide of SEQ ID NO: 2 is substituted to A. The present application also relates to a variant polypeptide as described herein, which comprises one or more of these substitutions. For example, the present application relates to a variant polypeptide as described herein, wherein the position corresponding to position 90 of the polypeptide of SEQ ID NO: 2 is substituted to L, the position corresponding to position 335 of the polypeptide of SEQ ID NO: 2 is substituted to V and the position corresponding to position 485 of the polypeptide of SEQ ID NO: 2 is substituted to I.

The present application relates to a variant polypeptide as described herein, which comprises substitution M90L. The present application relates to a variant polypeptide as described herein, which comprises substitution N103A. The present application relates to a variant polypeptide as described herein, which comprises substitution G142S. The present application relates to a variant polypeptide as described herein, which comprises substitution M335V. The present application relates to a variant polypeptide as described herein, which comprises substitution M485I. The present application relates to a variant polypeptide as described herein, which comprises substitution L606A. The present application also relates to a variant polypeptide as described herein, which comprises one or more of these substitutions. For example, the present application relates to a variant polypeptide as described herein, which comprises substitution M90L, M335V and M485I.

The present application relates to a variant polypeptide as described herein, which additionally differs in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65 amino acids from the amino acid sequence of its parent polypeptide. In an embodiment the parent polypeptide has beta-glucosidase activity and comprises at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the polypeptide of SEQ ID NO: 2.

In an embodiment the parent polypeptide is a fugal polypeptide. In an embodiment the parent polypeptide is a fungal beta-glucosidase. In an embodiment the parent polypeptide is a GH3 beta-glucosidase. In an embodiment the parent polypeptide is a *Rasamsonia* beta-glucosidase. In an embodiment the parent polypeptide is a *Rasamsonia emersonii* beta-glucosidase. In an embodiment the parent polypeptide comprises the amino acid sequence of SEQ ID NO: 2. In an embodiment the parent polypeptide consists of the amino acid sequence of SEQ ID NO: 2. The amino acid sequence of SEQ ID NO: 2 discloses the amino acid sequence of a wild-type (i.e. unmutated) *Rasamsonia emersonii* beta-glucosidase. *Rasamsonia emersonii* beta-glucosidase can also be called *Talaromyces emersonii* beta-glucosidase. The amino acid sequence of SEQ ID NO: 2 is identical to the amino acid sequence of SEQ ID NO: 5 as disclosed in WO 2011/098577. The variant polypeptide as described herein may be a variant of this beta-glucosidase.

Furthermore, the present application provides a polynucleotide encoding a variant polypeptide as described herein. The nucleotide sequence of SEQ ID NO: 1 encodes the amino acid sequence of SEQ ID NO: 2. The nucleotide sequence of SEQ ID NO: 1 is identical to the nucleotide sequence of SEQ ID NO: 6 as disclosed in WO 2011/098577. The nucleotide sequence of SEQ ID NO: 6 as disclosed in WO 2011/098577 encodes the amino acid sequence of SEQ ID NO: 5 as disclosed in WO 2011/098577.

The application also provides a nucleic acid construct or vector comprising a polynucleotide as described herein.

A host cell comprising the polynucleotide as described herein or the nucleic acid construct or vector as described herein is also part of the present application. In an embodiment the host cell as described herein is a fungal cell, preferably a fungal cell selected from the group consisting of the genera *Acremonium*, *Agaricus*, *Aspergillus*, *Aureobasidium*, *Chrysosporium*, *Coprinus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Piromyces*, *Panerochaete*, *Pleurotus*, *Schizophyllum*, *Talaromyces*, *Rasamsonia*, *Saccharomyces*, *Thermoascus*, *Thielavia*, *Tolypocladium*, and *Trichoderma*. In a host cell as described herein one or more genes can be deleted, knocked-out or disrupted in full or in part.

The application also provides a method of producing a variant polypeptide as described herein, which method comprises cultivating a host cell as described herein under conditions which allow for expression of the variant polypeptide and, optionally, recovering the expressed variant polypeptide. The application also relates to a method of producing a variant polypeptide as described herein, which method comprises the steps of (a) cultivating a host cell as described herein under conditions conducive to the production of the variant polypeptide, and (b) optionally, recovering the variant polypeptide.

Furthermore, the application provides a composition comprising (i) a variant polypeptide as described herein, and (ii) a cellulase and/or a hemicellulase and/or a pectinase. In an embodiment the cellulase is selected from the group consisting of a lytic polysaccharide monooxygenase, a cellobiohydrolase I, a cellobiohydrolase II, an endo-beta-1,4-glucanase, a beta-glucosidase and a beta-(1,3)(1,4)-glucanase or any combination thereof and the hemicellulase is selected from the group consisting of an endoxylanase, a beta-xylosidase, an alpha-L-arabinofuranosidase, an alpha-D-glucuronidase, a feruloyl esterase, a coumaroyl esterase, an alpha-galactosidase, a beta-galactosidase, a beta-mannanase, a beta-mannosidase or any combination thereof.

The variant polypeptides as described herein may be used in industrial methods as described in more detail herein.

Additionally, the application provides a method for the treatment of a substrate comprising cellulose and/or hemicellulose which method comprises the step of contacting the substrate with a variant polypeptide as described herein and/or a composition as described herein. In an embodiment the substrate is a cellulosic material. In another embodiment the substrate is a lignocellulosic material. In any event, the treatment results in the production of sugar.

Another aspect of the application relates to the use of a variant polypeptide as described herein and/or a composition as described herein to produce sugar from a lignocellulosic material.

The application also provides a method for producing sugar from cellulosic material which method comprises contacting the cellulosic material with a variant polypeptide as described herein and/or a composition as described herein and producing sugar from the cellulosic material.

The application also provides a method for producing sugar from lignocellulosic material which method comprises contacting the lignocellulosic material with a variant polypeptide as described herein and/or a composition as described herein and producing sugar from the lignocellulosic material.

The sugar produced may be used in a fermentation method as described herein. Accordingly, the application provides a method for producing a fermentation product, which method comprises the steps of treating a substrate using a method as described above, and fermenting the resulting material to produce a fermentation product. The resulting material may comprise sugar.

A polypeptide as described herein or a composition as described herein may also be used, for example, in the preparation of a food product, in the preparation of a detergent, in the preparation of an animal feed, in the treatment of pulp, in the manufacture of paper or in the preparation of a fabric or textile or in the cleaning thereof.

The application also provides a material obtainable by contacting a plant material or lignocellulosic material with a variant polypeptide as described herein and/or a composition as described herein; a food or feed comprising a variant polypeptide as described herein and/or a composition as described herein; and a plant or a part thereof which comprises a polynucleotide, a variant polypeptide, a nucleic acid construct, a vector or a host cell as described herein.

In case a variant polypeptide as described herein comprises a substitution at one or more positions corresponding to positions 90, 103, 142, 335, 485 and 606 of the polypeptide of SEQ ID NO: 2, this means that the variant polypeptide comprises a substitution at one of these positions, but also includes variant polypeptides that comprise a substitution at more than one of these positions. For example, a variant polypeptide as described herein may comprise a substitution at a position corresponding to positions 90, 142, and 485 of the polypeptide of SEQ ID NO: 2. Any combination of the listed positions is possible. Such combinations may have a synergistic effect.

As described above, when a variant polypeptide as described herein additionally differs in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65 amino acids from the amino acid sequence of its parent polypeptide, these additionally different amino acids are not chosen from the positions corresponding to positions 90, 103, 142, 335, 485 and 606 of the polypeptide of SEQ ID NO: 2.

In an embodiment the present application relates to a variant polypeptide comprising a substitution at a position corresponding to position 90 of SEQ ID NO: 2, wherein the polypeptide has beta-glucosidase activity and the polypeptide has at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the amino acid sequence of a parent beta-glucosidase. In an embodiment the polypeptide comprises a substitution at position 90 to L. In an embodiment the variant polypeptide comprises a substitution M90L.

In an embodiment the present application relates to a variant polypeptide comprising a substitution at a position corresponding to position 103 of SEQ ID NO: 2, wherein the polypeptide has beta-glucosidase activity and the polypeptide has at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the amino acid sequence of a parent beta-glucosidase. In an embodiment the polypeptide comprises a substitution at position 103 to A. In an embodiment the variant polypeptide comprises a substitution N103A.

In an embodiment the present application relates to a variant polypeptide comprising a substitution at a position corresponding to position 142 of SEQ ID NO: 2, wherein the polypeptide has beta-glucosidase activity and the polypeptide has at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the amino acid sequence of a parent beta-glucosidase. In an embodiment the polypeptide comprises a substitution at position 142 to S. In an embodiment the variant polypeptide comprises a substitution G142S.

In an embodiment the present application relates to a variant polypeptide comprising a substitution at a position corresponding to position 335 of SEQ ID NO: 2, wherein the polypeptide has beta-glucosidase activity and the polypeptide has at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the amino acid sequence of a parent beta-glucosidase. In an embodiment the polypeptide comprises a substitution at position 335 to V. In an embodiment the variant polypeptide comprises a substitution M335V.

In an embodiment the present application relates to a variant polypeptide comprising a substitution at a position corresponding to position 485 of SEQ ID NO: 2, wherein the polypeptide has beta-glucosidase activity and the polypeptide has at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the amino acid sequence of a parent beta-glucosidase. In an embodiment the polypeptide comprises a substitution at position 485 to I. In an embodiment the variant polypeptide comprises a substitution M485I.

In an embodiment the present application relates to a variant polypeptide comprising a substitution at a position corresponding to position 606 of SEQ ID NO: 2, wherein the polypeptide has beta-glucosidase activity and the polypeptide has at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the amino acid sequence of a parent beta-glucosidase. In an embodiment the polypeptide comprises a substitution at position 606 to A. In an embodiment the variant polypeptide comprises a substitution L606A.

In an embodiment the variant polypeptide comprises less than 100% sequence identity to the amino acid sequence of a parent beta-glucosidase. In an embodiment the amino acid sequence of the parent beta-glucosidase comprises SEQ ID NO: 2. In an embodiment the amino acid sequence of the parent beta-glucosidase consists of SEQ ID NO: 2.

The present application also relates to a variant polypeptide comprising a substitution at position 90 of SEQ ID NO: 4. In an embodiment the variant polypeptide comprises a substitution at position 90 of SEQ ID NO: 4 to L. In an embodiment the variant polypeptide comprises the substitution M90L in SEQ ID NO: 4. This variant polypeptide is an example of a variant polypeptide that comprises a substitution at a position corresponding to position 90 of SEQ ID NO: 2.

The present application also relates to a variant polypeptide comprising a substitution at position 103 of SEQ ID NO: 4. In an embodiment the variant polypeptide comprises a substitution at position 103 of SEQ ID NO: 4 to A. In an embodiment the variant polypeptide comprises the substitution N103A in SEQ ID NO: 4. This variant polypeptide is an example of a variant polypeptide that comprises a substitution at a position corresponding to position 103 of SEQ ID NO: 2.

The present application also relates to a variant polypeptide comprising a substitution at position 142 of SEQ ID NO: 4. In an embodiment the variant polypeptide comprises a substitution at position 142 of SEQ ID NO: 4 to S. In an embodiment the variant polypeptide comprises the substitution G142S in SEQ ID NO: 4. This variant polypeptide is an example of a variant polypeptide that comprises a substitution at a position corresponding to position 142 of SEQ ID NO: 2.

The present application also relates to a variant polypeptide comprising a substitution at position 335 of SEQ ID NO: 4. In an embodiment the variant polypeptide comprises a substitution at position 335 of SEQ ID NO: 4 to V. In an embodiment the variant polypeptide comprises the substitution M335V in SEQ ID NO: 4. This variant polypeptide is an example of a variant polypeptide that comprises a substitution at a position corresponding to position 335 of SEQ ID NO: 2.

The present application also relates to a variant polypeptide comprising a substitution at position 485 of SEQ ID NO: 4. In an embodiment the variant polypeptide comprises a substitution at position 485 of SEQ ID NO: 4 to I. In an embodiment the variant polypeptide comprises the substitution M485I in SEQ ID NO: 4. This variant polypeptide is an example of a variant polypeptide that comprises a substitution at a position corresponding to position 485 of SEQ ID NO: 2.

The present application also relates to a variant polypeptide comprising a substitution at position 607 of SEQ ID NO: 4. In an embodiment the variant polypeptide comprises a substitution at position 607 of SEQ ID NO: 4 to A. In an embodiment the variant polypeptide comprises the substitution L607A in SEQ ID NO: 4. This variant polypeptide is an example of a variant polypeptide that comprises a substitution at a position corresponding to position 606 of SEQ ID NO: 2.

The present application also relates to a variant polypeptide comprising a substitution at one or more positions corresponding to positions 90, 103, 142, 335, 485 and 607 of the polypeptide of SEQ ID NO: 4. In an embodiment the variant polypeptide has beta-glucosidase activity.

The present application relates to a variant polypeptide as described herein, which is a variant of a parent polypeptide which has beta-glucosidase activity and which comprises at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the polypeptide of SEQ ID NO: 4.

The present application relates to a variant polypeptide as described herein, which comprises at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the polypeptide of SEQ ID NO: 4.

The present application relates to a variant polypeptide as described herein, wherein the position corresponding to position 90 of the polypeptide of SEQ ID NO: 4 is substituted to L. The present application relates to a variant polypeptide as described herein, wherein the position corresponding to position 103 of the polypeptide of SEQ ID NO: 4 is substituted to A. The present application relates to a variant polypeptide as described herein, wherein the position corresponding to position 142 of the polypeptide of SEQ ID NO: 4 is substituted to S. The present application relates to a variant polypeptide as described herein, wherein the position corresponding to position 335 of the polypeptide of SEQ ID NO: 4 is substituted to V. The present application relates to a variant polypeptide as described herein, wherein the position corresponding to position 485 of the polypeptide of SEQ ID NO: 4 is substituted to I. The present application relates to a variant polypeptide as described herein, wherein the position corresponding to position 607 of the polypeptide of SEQ ID NO: 4 is substituted to A. The present application also relates to a variant polypeptide as described herein, which comprises one or more of these substitutions. For example, the present application relates to a variant polypeptide as described herein, wherein the position corresponding to position 90 of the polypeptide of SEQ ID NO: 4 is substituted to L, the position corresponding to position 335 of the polypeptide of SEQ ID NO: 4 is substituted to V and the position corresponding to position 485 of the polypeptide of SEQ ID NO: 4 is substituted to I.

The present application relates to a variant polypeptide as described herein, which comprises substitution M90L. The present application relates to a variant polypeptide as described herein, which comprises substitution N103A. The present application relates to a variant polypeptide as described herein, which comprises substitution G142S. The present application relates to a variant polypeptide as described herein, which comprises substitution M335V. The present application relates to a variant polypeptide as described herein, which comprises substitution M485I. The present application relates to a variant polypeptide as described herein, which comprises substitution L607A. The present application also relates to a variant polypeptide as described herein, which comprises one or more of these substitutions. For example, the present application relates to a variant polypeptide as described herein, which comprises substitution M90L, M335V and M485I. The present application relates to a variant polypeptide as described herein, which additionally differs in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65 amino acids from the amino acid sequence of its parent polypeptide. In an embodiment the parent polypeptide has beta-glucosidase activity and comprises at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to the polypeptide of SEQ ID NO: 4.

In an embodiment the parent beta-glucosidase is selected from the group consisting of the polypeptide comprising the amino acid sequence of SEQ ID NO: 2; the polypeptide comprising the amino acid sequence of SEQ ID NO: 4; a beta-glucosidase from *Aspergillus*, such as *Aspergillus oryzae*, such as the one disclosed in WO 02/095014; the fusion protein having beta-glucosidase activity disclosed in WO 2008/057637; a beta-glucosidase from *Aspergillus*, such as *Aspergillus fumigatus*, such as the one disclosed as SEQ ID NO:2 in WO 2005/047499 or SEQ ID NO:5 in WO 2014/130812; an *Aspergillus fumigatus* beta-glucosidase variant, such as one disclosed in WO 2012/044915; a beta-glucosidase with the following substitutions: F100D, S283G, N456E, F512Y (using SEQ ID NO: 5 in WO 2014/130812 for numbering); a beta-glucosidase from *Aspergillus* such as *Aspergillus aculeatus, Aspergillus niger* or *Aspergillus* kawachi; a beta-glucosidase from *Penicillium*, such as *Penicillium brasilianum* disclosed as SEQ ID NO:2 in WO 2007/019442; a beta-glucosidase from *Trichoderma*, such as *Trichoderma reesei*, such as ones described in U.S. Pat. Nos. 6,022,725, 6,982,159, 7,045,332, 7,005,289, US 2006/0258554, US 2004/0102619; a beta-glucosidase from *Thielavia terrestris* (see WO 2011/035029); and a beta-glucosidase from *Trichophaea saccata* (see WO 2007/019442). In an embodiment the parent beta-glucosidase may even be a bacterial beta-glucosidase. In an embodiment a variant polypeptide as described herein is less sensitive to glucose inhibition than the parent polypeptide (e.g. wild-type polypeptide) and thus has a higher glucose tolerance than the parent polypeptide (e.g. wild-type polypeptide). With "having a higher glucose tolerance" is meant that a variant polypeptide as described herein has a higher catalytic activity in the presence of glucose compared to the parent polypeptide (e.g. wild-type polypeptide). A wild-type polypeptide is for example the polypeptide comprising the amino acid sequence of SEQ ID NO: 2 or the polypeptide comprising the amino acid sequence of SEQ ID NO: 4.

In an embodiment a variant polypeptide as described herein has a higher ratio of remaining activity than the parent polypeptide (e.g. wild-type polypeptide). Ratio of remaining activity as used herein is defined as: (hydrolyzed cellobiose in presence of 20 g/l glucose)/(hydrolyzed cellobiose without added glucose). The hydrolysis of cellobiose can be measured as described in the examples section. In an embodiment the variant polypeptide as described herein has a ratio of remaining activity that is at least 5% higher than the ratio of remaining activity of the parent polypeptide (e.g. wild-type polypeptide). In an embodiment the variant polypeptide as described herein has a ratio of remaining activity that is at least 10% higher, at least 15% higher, at least 20% higher, at least 25% higher, at least 30% higher, at least 35% higher, at least 40% higher, at least 45% higher, at least 50% higher, at least 55% higher, at least 60% higher, at least 65% higher, at least 70% higher, at least 75% higher, at least 80% higher, at least 85% higher, at least 90% higher, at least 95% higher, at least 100% higher, at least 125% higher, at least 150% higher, at least 175% higher, at least 200% higher, at least 225% higher, at least 250% higher, at least 275% higher, at least 300% higher, at least 350% higher, at least 400% higher, at least 450% higher, at least 500% higher than the ratio of remaining activity of the parent polypeptide (e.g. wild-type polypeptide). In an embodiment the variant polypeptide as described herein has a ratio of remaining activity that is between 5% and 500% higher than the ratio of remaining activity of the parent polypeptide (e.g. wild-type polypeptide). Preferably, the variant polypeptide as described herein has a ratio of remaining activity that is between 5% and 400% higher than the ratio of remaining activity of the parent polypeptide (e.g. wild-type polypeptide). Preferably, the variant polypeptide as described herein has a ratio of remaining activity that is between 5% and 300% higher than the ratio of remaining activity of the parent polypeptide (e.g. wild-type polypeptide). A wild-type polypeptide is for example the polypeptide comprising the amino acid sequence of SEQ ID NO: 2 or the polypeptide comprising the amino acid sequence of SEQ ID NO: 4.

The present application provides novel polypeptides, e.g. enzymes, which have the ability to modify, for example degrade, a carbohydrate material. A carbohydrate material is a material which comprises, consists of, or substantially consists of one or more carbohydrates. The present application also provides polynucleotides encoding the polypeptides. In an embodiment a variant polypeptide as described herein is isolated. In an embodiment the variant polypeptide as described herein is an enzyme. In an embodiment the variant polypeptide as described herein is a carbohydrate degrading enzyme. In an embodiment the variant polypeptide as described herein is a carbohydrate hydrolysing enzyme. In an embodiment the variant polypeptide as described herein comprises beta-glucosidase activity.

In an embodiment the variant polypeptide as described herein comprises advantageously one or more additional substitutions, wherein the one or more additional substotutions are preferably giving an additional effect which may even further improve the advantageous property of the variant polypeptide as described herein or may give another advantageous property to the variant polypeptide as described herein.

In an embodiment the variant polypeptide as described herein has beta-glucosidase activity. In an embodiment the variant polypeptide as described herein is a beta-glucosidase. In an embodiment the variant polypeptide as described herein is a GH3 beta-glucosidase.

A beta-glucosidase (EC 3.2.1.21) is any polypeptide which is capable of catalysing the hydrolysis of terminal, non-reducing beta-D-glucose residues with release of beta-D-glucose. Such a polypeptide may have a wide specificity for beta-D-glucosides and may also hydrolyze one or more of the following: a beta-D-galactoside, an alpha-L-arabinoside, a beta-D-xyloside or a beta-D-fucoside. This enzyme may also be referred to as amygdalase, beta-D-glucoside glucohydrolase, cellobiase or gentobiase.

By "variant polypeptide comprising a substitution at a position corresponding to position X of the polypeptide of SEQ ID NO: Y" is meant the position X determined from an amino acid sequence alignment of the amino acid sequence of the variant polypeptide with the polypeptide of SEQ ID NO: Y. This means that the specific substitution claimed with regard to the position X in the amino acid sequence of SEQ ID NO: Y, may be found on a different position in the amino acid sequence of the variant polypeptide. For example, the substitution to A on position 606 of the amino acid sequence of SEQ ID NO: 2, may have a different position in the amino acid sequence of a variant polypeptide. For example, the substitution L606A in the amino acid sequence of SEQ ID NO: 2 corresponds with the mutation L607A in the amino acid sequence of SEQ ID NO: 4. In addition, the original amino acid in the parent of the variant polypeptide may differ from the original amino acid in the amino acid sequence of SEQ ID NO: 2. The amino acid at a position in the parent of the variant polypeptide that corresponds to position 90 in the amino acid sequence of SEQ ID NO: 2 can differ from the M as found on position 90 in the amino acid sequence of SEQ ID NO: 2. It could be any amino acid (except L). The position and type of amino acid to be substituted in parent polypeptides can be found through alignment of the amino acid sequences of the parent polypeptides with SEQ ID NO: 2. The alignment can be made using the Clustal Omega computer program (Clustal Omega computer program is a multiple sequence alignment program that uses seeded guide trees and HMM profile-profile techniques to generate alignments www.ebi.ac.uk/Tools/msa/clustalo).

In an embodiment the one or more substitutions as described herein increase thermostability of a variant polypeptide as compared to its parent polypeptide. In an embodiment the one or more substitutions as described herein increase glucose tolerance of a variant polypeptide as compared to its parent polypeptide. In an embodiment the one or more substitutions as described herein increase thermostability and increase glucose tolerance of a variant polypeptide as compared to its parent polypeptide.

As described above, the variant polypeptide as described herein is preferably a polypeptide such as an enzyme, more preferably is a carbohydrate degrading enzyme and/or carbohydrate hydrolysing enzyme and most preferably comprises beta-glucosidase activity. A variant polypeptide as described herein may have one or more alternative and/or additional activities, for example, one of the other oxidoreductase, transferase, hydrolase, lyase, isomerase or ligase activities mentioned herein.

The application provides the use of a variant polypeptide as described herein and compositions comprising the variant polypeptide as described herein in industrial methods as described in more detail herein.

According to a preferred embodiment the variant polypeptide as described herein is a "thermostable" polypeptide. In another preferred embodiment the polynucleotide as described herein encodes a variant polypeptide as described herein with a high thermostability that is more stable under lignocellulosic feedstock hydrolysis conditions. Herein, a "thermostable" polypeptide means that the polypeptide has a higher residual catalytic activity after a heat-shock temperature treatment as compared to a polypeptide with lower thermostability (e.g. a polypeptide not having the respective substitution(s), i.e. its parent polypeptide). A higher stability under process conditions can be identified by determining the residual catalytic activity of the polypeptide after the hydrolysis reaction time, for example 72 hours.

According to a preferred embodiment the variant polypeptide as described herein has a pH optimum between pH 2 and pH 8. Preferably, the polypeptide has a pH optimum of 6 or lower, 5 or lower, 4.5 or lower, 4 or lower, or even 3.5 or lower. Preferably, the polypeptide has a pH optimum of 2 or higher, preferably 2.5 or higher. Preferably, the polypeptide has a pH optimum of 3 to 5. The pH optimum is the pH during hydrolysis at which the polypeptide has optimum activity when measured during a certain period of time.

Polynucleotide Sequence

The application also relates to a polynucleotide which encodes a variant polypeptide as described herein. In an embodiment the polynucleotide as described herein is isolated.

In an embodiment the polynculeotide as described herein has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleotide sequence of SEQ ID NO: 1.

In an embodiment the polynculeotide as described herein has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleotide sequence of SEQ ID NO: 3.

In an embodiment the polynculeotide as described herein has less than 100% sequence identity to the nucleotide sequence of SEQ ID NO: 1. In an embodiment the polynculeotide as described herein has less than 100% sequence identity to the nucleotide sequence of SEQ ID NO: 3.

A polynucleotide as described herein can be isolated using standard molecular biology techniques and the sequence information provided herein. For example, by using standard hybridization and cloning techniques as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

Moreover, a polynucleotide may be isolated by the polymerase chain reaction (PCR) using synthetic oligonucleotide primers designed based upon the sequence information contained in the sequence of the polynucleotide.

A polynucleotide as described herein can be amplified using cDNA, mRNA or alternatively, genomic DNA, as a template and appropriate oligonucleotide primers according to standard PCR amplification techniques. The polynucleotide so amplified can be cloned into an appropriate vector and characterized by DNA sequence analysis.

Furthermore, oligonucleotides corresponding to or hybridizing to a nucleotide sequence as described herein can be prepared by standard synthetic techniques, e.g. using an automated DNA synthesizer.

A polynucleotide which is complementary to a nucleotide sequence is one which is sufficiently complementary to the other nucleotide sequence such that it can hybridize to the other nucleotide sequence thereby forming a stable duplex. The term "cDNA" (complementary DNA) is defined herein as a DNA molecule which can be prepared by reverse transcription from a mRNA molecule. cDNA derived from mRNA only contains coding sequences and can be directly translated into the corresponding polypeptide product. The term "complementary strand" can be used interchangeably with the term "complement". The complement of a nucleotide strand can be the complement of a coding strand or the complement of a non-coding strand. When referring to double-stranded polynucleotides, the complement of a polynucleotide encoding a polypeptide refers to the complementary strand of the strand encoding the amino acid sequence or to any polynucleotide containing the same.

As used herein, the term "hybridization" means the pairing of substantially complementary strands of oligomeric compounds. One mechanism of pairing involves hydrogen bonding, which may be Watson-Crick, Hoogsteen or reversed Hoogsteen hydrogen bonding, between complementary nucleotide bases (nucleotides) of the strands of oligomeric compounds. For example, adenine and thymine are complementary nucleic acids which pair through the formation of hydrogen bonds. Hybridization can occur under varying circumstances. "Stringency hybridization" or "hybridizes under low stringency, medium stringency, high stringency, or very high stringency conditions" is used herein to describe conditions for hybridization and washing, more specifically conditions under which an oligomeric compound will hybridize to its target sequence, but to a minimal number of other sequences. So, the oligomeric compound will hybridize to the target sequence to a detectably greater degree than to other sequences. Guidance for performing hybridization reactions can be found in Current Protocols in Molecular Biology, John Wiley & Sons, N.Y. (1989), 6.3.1-6:3.6. Aqueous and non-aqueous methods are described in that reference and either can be used. Stringency conditions are sequence-dependent and will be different in different circumstances. Generally, stringency conditions are selected to be about 5° C. lower than the thermal melting point (Tm) for the oligomeric compound at a defined ionic strength and pH. The Tm is the temperature (under defined ionic strength and pH) at which 50% of an oligomeric compound hybridizes to a perfectly matched probe. Stringency conditions may also be achieved with the addition of destabilizing agents such as formamide.

Examples of specific hybridization conditions are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5M sodium phosphate, 7% SDS at 65° C., followed by one or more washes at 0.2×SSC, 1% SDS at 65° C.

In general, high stringency conditions, such as high hybridization temperature and optionally low salt concentrations, permit only hybridization between sequences that are highly similar, whereas low stringency conditions, such as low hybridization temperature and optionally high salt concentrations, allow hybridization when the sequences are less similar.

One aspect of the application pertains to isolated polynucleotides that encode a variant polypeptide as described herein as well as polynucleotides sufficient for use as hybridization probes to identify polynucleotides encoding a variant polypeptide as described herein.

The term "naturally-occurring" as used herein refers to methods, events, or things that occur in their relevant form in nature. By contrast, "not naturally-occurring" refers to methods, events, or things whose existence or form involves the hand of man. Generally, the term "naturally-occurring" with regard to polypeptides or polynucleotides can be used interchangeable with the term "wild-type" or "native". It refers to polypeptide or polynucleotides encoding a polypeptide, having an amino acid sequence or nucleotide sequence, respectively, identical to that found in nature. Naturally-occurring polypeptides include native polypeptides, such as those polypeptides naturally expressed or found in a particular host. Naturally-occurring polynucleotides include native polynucleotides such as those polynucleotides naturally found in the genome of a particular host. Additionally, a sequence that is wild-type or naturally-occurring may refer to a sequence from which a variant or a synthetic sequence is derived.

In an embodiment the variant polypeptides as described herein and the polynucleotides as described herein are not naturally-occurring.

As used herein, a "synthetic" molecule is produced by in vitro chemical or enzymatic synthesis. It includes, but is not limited to, polynucleotides made with optimal codon usage for host organisms of choice.

The term "recombinant" when used in reference to a host cell, polynucleotide, polypeptide, nucleic acid construct or vector, indicates that the host cell, polynucleotide, polypeptide or vector, has been modified by the introduction of a heterologous polynucleotide or polypeptide or the alteration of a native polynucleotide or polypeptide, or that the host cell is derived from a host cell so modified. Thus, for example, recombinant host cells express polynucleotides that are not found within the native (non-recombinant) form of the host cell or express native genes that are otherwise abnormally expressed, under expressed or not expressed at all. The term "recombinant" is synonymous with "genetically-modified".

The term "isolated polypeptide" as used herein means a polypeptide that is removed from at least one component, e.g. other polypeptide material, with which it is naturally associated. Thus, an isolated polypeptide may contain at most 10%, at most 8%, more preferably at most 6%, more preferably at most 5%, more preferably at most 4%, more preferably at most 3%, even more preferably at most 2%, even more preferably at most 1% and most preferably at most 0.5% as determined by SDS-PAGE of other polypeptide material with which it is natively associated. The isolated polypeptide may be free of any other impurities. The isolated polypeptide may be at least 50% pure, at least 60% pure, at least 70% pure, at least 75% pure, at least 80% pure, at least 85% pure, at least 90% pure, at least 95% pure, at least 96% pure, at least 97% pure, at least 98% pure, at least 99% pure, at least 99.5% pure, at least 99.9% pure as determined by SDS-PAGE or any other analytical method suitable for this purpose and known to the person skilled in the art.

An "isolated polynucleotide" or "isolated nucleic acid" is a polynucleotide removed from other polynucleotides with which it is naturally associated. Thus, an isolated polynucleotide may contain at most 10%, at most 8%, more preferably at most 6%, more preferably at most 5%, more preferably at most 4%, more preferably at most 3%, even more preferably at most 2%, even more preferably at most 1% and most preferably at most 0.5% by weight of other polynucleotide material with which it is naturally associated. The isolated polynucleotide may be free of any other impurities. The isolated polynucleotide may be at least 50% pure, at least 60% pure, at least 70% pure, at least 75% pure, at least 80% pure, at least 85% pure, at least 90% pure, or at least 95% pure, at least 96% pure, at least 97% pure, at least 98% pure, at least 99% pure, at least 99.5% pure, at least 99.9% pure by weight.

The term "substantially pure" with regard to polypeptides refers to a polypeptide preparation which contains at the most 50% by weight of other polypeptide material. The polypeptides disclosed herein are preferably in a substantially pure form. In particular, it is preferred that the polypeptides disclosed herein are in "essentially pure form", i.e. that the polypeptide preparation is essentially free of other polypeptide material. Optionally, the polypeptide may also be essentially free of non-polypeptide material such as nucleic acids, lipids, media components, and the like. Herein, the term "substantially pure polypeptide" is synonymous with the terms "isolated polypeptide" and "polypeptide in isolated form". The term "substantially pure" with regard to polynucleotide refers to a polynucleotide preparation which contains at the most 50% by weight of other polynucleotide material. The polynucleotides disclosed herein are preferably in a substantially pure form. In particular, it is preferred that the polynucleotide disclosed herein are in "essentially pure form", i.e. that the polynucleotide preparation is essentially free of other polynucleotide material. Optionally, the polynucleotide may also be essentially free of non-polynucleotide material such as polypeptides, lipids, media components, and the like. Herein, the term "substantially pure polynucleotide" is synonymous with the terms "isolated polynucleotide" and "polynucleotide in isolated form".

The term "nucleic acid" as used in the present application refers to a nucleotide polymer including at least 5 nucleotide units. A nucleic acid refers to a ribonucleotide polymer (RNA), deoxynucleotide polymer (DNA) or a modified form of either type of nucleic acid or synthetic form thereof or mixed polymers of any of the above. Nucleic acids may include either or both naturally-occurring and modified nucleic acids linked together by naturally-occurring and/or non-naturally occurring nucleic acid linkages. The nucleic acid molecules may be modified chemically or biochemically or may contain non-natural or derivatized nucleic acid bases, as will be readily appreciated by those of skill in the art. Such modifications include, for example, labels, methylation, substitution of one or more of the naturally occurring nucleic acids with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) The term nucleic acid is also intended to include any topological conformation, including single-stranded (sense strand and antisense strand), double-stranded, partially duplexed, triplex, hairpinned, circular and padlocked conformations. Also included are synthetic molecules that mimic nucleic acids in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for antisense therapy, hybridization probes and PCR primers. The term "nucleic acid", "nucleic acid molecule" and "polynucleotide" can be used interchangeably herein. The term "nucleic acid sequence" and "nucleotide sequence" can also be used interchangeably herein.

A "substitution", as used herein in relation to polypeptides or polynucleotides, denotes the replacement of one or more amino acids in a polypeptide sequence or of one or more nucleotides in a nucleotide sequence, respectively, by different amino acids or nucleotides, respectively.

Another embodiment of the application provides an isolated polynucleotide which is antisense to a polynucleotide as described herein, e.g. the coding strand of a polynucleotide as described herein. Also included within the scope of the application are the complementary strands of the polynucleotides described herein.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule.

The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The term "deletion" as used herein denotes a change in either amino acid or nucleotide sequence in which one or more amino acids or nucleotides, respectively, are absent as compared to the parent, often the naturally-occurring, amino acid or nucleotide sequence.

The term "insertion", also known as the term "addition", denotes a change in an amino acid or nucleotide sequence resulting in the addition of one or more amino acids or nucleotides, respectively, as compared to the parent, often the naturally-occurring, amino acid or nucleotide sequence.

A person skilled in the art is capable of identifying such erroneously identified bases and knows how to correct for such errors.

A polynucleotide as described herein may encoding only a portion of a variant polypeptide as described herein.

The probe/primer typically comprises a substantially purified oligonucleotide which typically comprises a nucleotide sequence that hybridizes preferably under highly stringent conditions to at least from about 12 to about 15, preferably from about 18 to about 20, preferably from about 22 to about 25, more preferably about 30, about 35, about 40, about 45, about 50, about 55, about 60, about 65, or about 75 or more consecutive nucleotides of a nucleotide sequence.

Probes can be used to detect nucleotide sequences encoding the same or homologous polypeptides, for instance in other organisms. In preferred embodiments, the probe further comprises a label group attached thereto, e.g. the label group can be a radioisotope, a fluorescent compound, an enzyme, or an enzyme cofactor. Such probes can also be used as part of a diagnostic test kit for identifying cells which express a variant polypeptide as described herein.

The polynucleotides as described herein may be synthetic polynucleotides. The synthetic polynucleotides may be optimized in codon use, preferably according to the methods described in WO 2006/077258 and/or PCT/EP2007/055943, which are herein incorporated by reference. PCT/EP2007/055943 addresses codon-pair optimization. Codon-pair optimization is a method wherein the nucleotide sequences encoding a polypeptide have been modified with respect to their codon usage, in particular the codon pairs that are used, to obtain improved expression of the nucleotide sequence encoding the polypeptide and/or improved production of the encoded polypeptide. Codon pairs are defined as a set of two subsequent triplets (codons) in a coding sequence. Those skilled in the art will know that the codon usage needs to be adapted depending on the host species, possibly resulting in variants with significant homology deviation from a given nucleotide sequence, but still encoding a variant polypeptide as described herein.

The term "expression" includes any step involved in the production of the polypeptide including, but not limited to, transcription, post-transcriptional modification, translation, post-translational modification, and secretion.

Nucleic Acid Construct

The application further relates to a nucleic acid construct or vector comprising a polynucleotide as described herein. The term "nucleic acid construct" is herein referred to as a nucleic acid molecule, either single- or double-stranded, which is isolated from a naturally-occurring gene or which has been modified to contain segments of nucleic acids which are combined and juxtaposed in a manner which would not otherwise exist in nature. The term nucleic acid construct is synonymous with the term "expression cassette" when the nucleic acid construct contains all the control sequences required for expression of a coding sequence, wherein said control sequences are operably linked to said coding sequence.

The term "coding sequence" as defined herein is a sequence, which is transcribed into mRNA and translated into a polypeptide. The boundaries of the coding sequence are generally determined by the ATG start codon at the 5'-end of the mRNA and a translation stop codon sequence terminating the open reading frame at the 3'-end of the mRNA. A coding sequence can include, but is not limited to, DNA, cDNA, and recombinant nucleotide sequences. Preferably, the nucleic acid has high GC content. The GC content herein indicates the number of G and C nucleotides in the construct, divided by the total number of nucleotides, expressed in %. The GC content is preferably 56% or more, 57% or more, 58% or more, 59% or more, 60% or more, or in the range of 56-70% or the range of 58-65%. Preferably, the nucleic acid construct comprises a promoter sequence, a coding sequence in operative association with said promoter sequence and control sequences, such as (a) a translational termination sequence orientated in 5' towards 3' direction, and/or (b) a translational initiator coding sequence orientated in 5' towards 3' direction, and/or (c) a translational initiator sequence In the context of this application, the term "translational initiator coding sequence" is defined as the nucleotides immediately downstream of the initiator or start codon of the open reading frame of a coding sequence. The initiator or start codon encodes for the AA methionine. The initiator codon is typically ATG, but may also be any functional start codon such as GTG.

In the context of this application, the term "translational termination sequence" is defined as the nucleotides starting from the translational stop codon at the 3' end of the open reading frame or nucleotide coding sequence and oriented in 5' towards 3' direction.

In the context of this application, the term "translational initiator sequence" is defined as the nucleotides immediately upstream of the initiator or start codon of the open reading frame of a sequence coding for a polypeptide.

In an embodiment the nucleic acid construct is a vector, such as an expression vector, wherein the polynucleotide as described herein is operably linked to at least one control sequence for the expression of the polynucleotide in a host cell.

An expression vector comprises a polynucleotide coding for a polypeptide, operably linked to the appropriate control sequences (such as a promoter, and transcriptional and translational stop signals) for expression and/or translation in vitro or in a host cell. Certain vectors are capable of directing the expression of genes to which they are operatively linked. Such vectors are referred to herein as "expression vectors". In general, expression vectors of utility in recombinant DNA techniques are often in the form of plasmids.

The expression vector may be any vector (e.g. a plasmid or virus), which can be conveniently subjected to recombinant DNA procedures and can bring about the expression of the polynucleotide. The choice of the vector will typically depend on the compatibility of the vector with the cell into which the vector is to be introduced. The vectors may be linear or closed circular plasmids. The vector may be an autonomously replicating vector, i.e. a vector which exists as an extra-chromosomal entity, the replication of which is independent of chromosomal replication, e.g. a plasmid, an extra-chromosomal element, a mini-chromosome, or an artificial chromosome. Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell.

The vector system may be a single vector or plasmid or two or more vectors or plasmids, which together contain the total DNA to be introduced into the genome of the host cell, or a transposon.

The vectors preferably contain one or more selectable markers which permit easy selection of transformed cells.

Another aspect of the application pertains to vectors, including cloning and expression vectors, comprising a polynucleotide as described herein encoding and methods of growing, transforming or transfecting such vectors in a suitable host cell, for example under conditions in which expression of a variant polypeptide as described herein occurs.

As used herein, the term "vector" refers to a nucleic acid molecule capable of transporting another nucleic acid to which it has been linked. Thus, in a further embodiment the application provides a method of making polynucleotides as described herein by introducing a polynucleotide as described herein into a replicable vector, introducing the vector into a compatible host cell, and growing the host cell under conditions which bring about replication of the vector. The vector may be recovered from the host cell. Suitable host cells are described below.

One type of vector is a "plasmid", which refers to a circular double stranded DNA loop into which additional DNA segments can be ligated. Another type of vector is a viral vector, wherein additional DNA segments can be ligated into the viral genome. The terms "plasmid" and "vector" can be used interchangeably herein as the plasmid is the most commonly used form of vector. However, the application is intended to include such other forms of expression vectors, such as cosmids, viral vectors (e.g. replication defective retroviruses, adenoviruses and adeno-associated viruses) and phage vectors which serve equivalent functions.

Vectors as described herein may be used in vitro, for example for the production of RNA or used to transfect or transform a host cell.

A vector as described herein may comprise two or more, for example three, four or five polynucleotides as described herein, for example for overexpression.

The recombinant expression vectors as described herein comprise a polynucleotide as described herein in a form suitable for expression of the polynucleotide in a host cell, which means that the recombinant expression vector includes one or more regulatory sequences selected on the basis of the host cells to be used for expression, which is operably linked to the nucleotide sequence to be expressed.

The term "operably linked", "operatively linked" or "in operative association" as used herein refers to two or more nucleotide sequence elements that are physically linked and are in a functional relationship with each other. For instance, a promoter is operably linked to a coding sequence, if the promoter is able to initiate or regulate the transcription or expression of a coding sequence, in which case the coding sequence should be understood as being "under the control of" the promoter. Generally, when two nucleotide sequences are operably linked, they will be in the same orientation and usually also in the same reading frame. They usually will be essentially contiguous, although this may not be required.

A vector or nucleic construct for a given host cell may thus comprise the following elements operably linked to each other in a consecutive order from the 5'-end to the 3'-end relative to the coding strand of the sequence encoding a variant polypeptide as described herein: (1) a promoter sequence capable of directing transcription of the nucleotide sequence encoding the variant polypeptide as described herein in the given host cell, (2) optionally, a signal sequence capable of directing secretion of the polypeptide from the given host cell into a culture medium, (3) a nucleotide sequence as described herein encoding a mature and preferably active form of the variant polypeptide as described herein, and preferably also (4) a transcription termination region (terminator) capable of terminating transcription downstream of the nucleotide sequence encoding the variant polypeptide as described herein.

Downstream of the nucleotide sequence as described herein there may be a 3'-untranslated region containing one or more transcription termination sites (e.g. a terminator). The terminator can, for example, be native to the nucleotide sequence encoding the polypeptide. However, preferably a yeast terminator is used in yeast host cells and a filamentous fungal terminator is used in filamentous fungal host cells. More preferably, the terminator is endogenous to the host cell (in which the nucleotide sequence encoding the polypeptide is to be expressed). In the transcribed region, a ribosome binding site for translation may be present. The coding portion of the mature transcripts expressed by the constructs will include a translation initiating AUG at the beginning and a termination codon appropriately positioned at the end of the polypeptide to be translated.

Enhanced expression of the polynucleotide as described herein may also be achieved by the selection of heterologous regulatory regions, e.g. promoter, secretion leader and/or terminator regions, which may serve to increase expression and, if desired, secretion levels of the variant polypeptide as described herein from the expression host and/or to provide for the inducible control of the expression of the variant polypeptide as described herein.

It will be appreciated by those skilled in the art that the design of the expression vector can depend on such factors as the choice of the host cell to be transformed, the level of expression of the polypeptide, etc.

The vectors, such as expression vectors, as described herein can be introduced into host cells to produce a variant polypeptide as described herein. The vectors, such as recombinant expression vectors, as described herein can be designed for expression of the polypeptides in prokaryotic or eukaryotic cells.

The recombinant expression vector can also be transcribed and translated in vitro, for example using T7 promoter regulatory sequences and T7 polymerase.

For most filamentous fungi and yeast, the vector or nucleic acid construct is preferably integrated in the genome of the host cell in order to obtain stable transformants. However, for certain yeasts also suitable episomal vectors are available into which the expression construct can be incorporated for stable and high level expression. Examples thereof include vectors derived from the 2p and pKD1 plasmids of *Saccharomyces* and *Kluyveromyces*, respectively, or vectors containing an AMA sequence (e.g. AMA1 from *Aspergillus*). In case the expression constructs are integrated in the host cells genome, the constructs are either integrated at random loci in the genome or at predetermined target loci using homologous recombination, in which case the target loci preferably comprise a highly expressed gene.

Accordingly, expression vectors useful in the present application include chromosomal-, episomal- and virus-derived vectors, e.g. vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The term "control sequence" or "regulatory sequence" can be used interchangeably with the term "expression-regulating nucleic acid sequence". The term as used herein refers to nucleotide sequences necessary for and/or affecting the expression of an operably linked coding sequence in a particular host organism or in vitro. When two nucleic acid sequences are operably linked, they usually will be in the same orientation and also in the same reading frame. They usually will be essentially contiguous, although this may not be required. The expression-regulating nucleic acid sequences, such as inter alia appropriate transcription initiation, termination, promoter, leader, signal peptide, propeptide, prepro-peptide, or enhancer sequences; Shine-Delgarno sequence, repressor or activator sequences; efficient RNA methoding signals such as splicing and polyadenylation signals; sequences that stabilize cytoplasmic mRNA; sequences that enhance translation efficiency (e.g. ribosome binding sites); sequences that enhance protein stability; and when desired, sequences that enhance protein secretion, can be any nucleotide sequence showing activity in the host organism of choice and can be derived from genes encoding proteins, which are either homologous or heterologous to the host organism. Each control sequence may be native or foreign to the nucleotide sequence encoding the polypeptide. When desired, the control sequence may be provided with linkers for the purpose of introducing specific restriction sites facilitating ligation of the control sequences with the coding region of the nucleic acid sequence encoding a polypeptide. Control sequences may be optimized to their specific purpose.

The control sequence may be an appropriate promoter sequence, a nucleotide sequence, which is recognized by a host cell for expression of the nucleotide sequence. The promoter sequence contains transcriptional control sequences, which mediate the expression of the polypeptide. The promoter may be any nucleotide sequence, which shows transcriptional activity in the cell including mutant, truncated, and hybrid promoters, and may be obtained from genes encoding extracellular or intracellular polypeptides, either homologous or heterologous to the cell.

The term "promoter" is defined herein as a nucleotide sequence that binds RNA polymerase and directs the polymerase to the correct downstream transcriptional start site of a nucleotide sequence encoding a biological compound to initiate transcription. RNA polymerase effectively catalyses the assembly of messenger RNA complementary to the appropriate DNA strand of a coding region. The term "promoter" will also be understood to include the 5'-non-coding region (between promoter and translation start) for translation after transcription into mRNA, cis-acting transcription control elements such as enhancers, and other nucleotide sequences capable of interacting with transcription factors. The promoter may be any appropriate promoter sequence suitable for a eukaryotic or prokaryotic host cell, which shows transcriptional activity, including mutant, truncated, and hybrid promoters, and may be obtained from polynucleotides encoding extracellular or intracellular polypeptides either homologous (native) or heterologous (foreign) to the cell.

The promoter may be a constitutive or inducible promoter. Preferably, the promoter is an inducible promoter. More preferably the promoter is a carbohydrate inducible promoter. Carbohydrate inducible promoters are known in the art. In a preferred embodiment the promoter is suitable in filamentous fungi. Such promoters are known in the art. In a preferred embodiment the promoter is a *Rasamsonia* promoter. Preferably, the promoter sequence is from a highly expressed gene. Highly expressed genes are known in the art.

The promoters used in the host cells as described herein may be modified, if desired, to affect their control characteristics. Suitable promoters in this context include both constitutive and inducible natural promoters as well as engineered promoters, which are well-known to the person skilled in the art.

Transcription of the nucleotide sequence encoding the variant polypeptides as described herein by higher eukaryotes may be increased by inserting an enhancer sequence into the vector. Enhancers are cis-acting elements of DNA, usually about from 10 to 300 base pairs, that act to increase transcriptional activity of a promoter in a given host cell type. Examples of suitable enhancers are well-known to the person skilled in the art.

The control sequence may also be a suitable transcription terminator sequence, a sequence recognized by a host cell to terminate transcription. The terminator sequence is operably linked to the 3'-terminus of the nucleotide sequence encoding the polypeptide. Any terminator, which is functional in the cell, may be used in the present application. Examples of suitable transcription terminator sequences are well-known to the person skilled in the art.

The control sequence may also include a suitable leader sequence, a non-translated region of a mRNA which is important for translation by the host cell. The leader sequence is operably linked to the 5'-terminus of the nucleotide sequence encoding the polypeptide. Any leader sequence, which is functional in the cell, may be used in the present application. Examples of suitable leader sequences are well known to the person skilled in the art.

The control sequence may also be a polyadenylation sequence, a sequence which is operably linked to the 3'-terminus of the nucleotide sequence and which, when transcribed, is recognized by the host cell as a signal to add polyadenosine residues to transcribed mRNA. Any polyadenylation sequence, which is functional in the cell, may be used in the present application. Examples of suitable polyadenylation sequences are well-known to the person skilled in the art.

When the variant polypeptide as described herein is to be secreted from the host cell into the cultivation medium, an appropriate signal sequence can be added to the polypeptide in order to direct the de novo synthesized polypeptide to the secretion route of the host cell. The person skilled in the art knows to select an appropriate signal sequence for a specific host. The signal sequence may be native to the host cell, or may be foreign to the host cell. As an example, a signal sequence from a protein native to the host cell can be used. Preferably, said native protein is a highly secreted protein. Examples of suitable signal sequences are well-known to the person skilled in the art.

As an alternative for a signal sequence, the variant polypeptide as described herein can be fused to a secreted carrier protein, or part thereof. Such chimeric construct is directed to the secretion route by means of the signal sequence of the carrier protein or part thereof. In addition, the carrier protein will provide a stabilizing effect to the polypeptide as described herein and or may enhance solubility. Such carrier protein may be any protein. Preferably, a highly secreted protein is used as a carrier protein. The carrier protein may be native or foreign to the variant polypeptide as described herein. The carrier protein may be native of may be foreign to the host cell. The carrier protein and variant polypeptide as described herein may contain a specific amino acid motif to facilitate isolation of the polypeptide. The variant polypeptide as described herein may be released by a special releasing agent. The releasing agent may be a proteolytic enzyme or a chemical agent. Examples of suitable carrier proteins are well-known to the person skilled in the art.

As an alternative for secretion of the variant polypeptide as described herein into the medium, the variant polypeptide as described herein can be fused to a localisation sequence to target the variant polypeptide as described herein to a desired cellular compartment, organelle of a cell, or membrane. Such sequences are known to the person skilled in the art and include organelle targeting sequences.

Alternatively, the variant polypeptide as described herein is fused to another protein that has carbohydrate degrading activity. Optionally, the variant polypeptide as described herein is flanked on the C-terminal and/or the N-terminal side by an amino acid motif that facilitates identification, isolation and/or purification.

Homology and Identity

The terms "sequence homology" or "sequence identity" are used interchangeably herein. For the purpose of this application, it is defined here that in order to determine the percentage of sequence homology or sequence identity of two amino acid sequences or of two nucleotide sequences, the sequences are aligned for optimal comparison purposes. In order to optimize the alignment between the two sequences, gaps may be introduced in any of the two sequences that are compared. Such alignment can be carried out over the full-length of the sequences being compared. Alternatively, the alignment may be carried out over a shorter length, for example over about 20, about 50, about 100 or more nucleotides or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison. In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this application, the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinformatics.nl). For amino acid sequences, EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above, the percentage of sequence identity between a query sequence and a sequence as described herein is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleotide and amino acid sequences as described herein can further be used as a "query sequence" to perform a search against sequence databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to polynucleotides as described herein. BLAST protein searches can be performed with the XBLAST program, score=50, word length=3 to obtain amino acid sequences homologous to polypeptides as described herein. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used.

Host Cells

In an embodiment the host cell comprises a variant polypeptide as described herein, a polynucleotide as described herein or a nucleic acid construct or vector as described herein.

The term "host cell" as used herein means any type of cell that is susceptible to transformation, transfection, transduction or the like with a polynucleotide as described herein or a nucleic acid construct or vector as described herein. It encompasses any progeny of a parent cell that is not identical to the parent cell due to mutations that occur during replication. In an embodiment the host cell is a recombinant host cell.

The variant polypeptides as described herein can be expressed in both prokaryotic and eukaryotic cells.

A prokaryotic host cell includes, but is not limited to, a bacterial host cell. The term "bacterial cell" includes both Gram-negative and Gram-positive microorganisms. Examples of bacteria include, but are not limited to, bacteria belonging to the genus *Bacillus* (e.g. *B. subtilis, B. amyloliquefaciens, B. licheniformis, B. puntis, B. megaterium, B. halodurans, B. pumilus*), *Acinetobacter, Nocardia, Xanthobacter, Escherichia* (e.g. *E. coli*), *Streptomyces, Erwinia, Klebsiella, Serratia* (e.g. S. marcessans), *Pseudomonas* (e.g. *P. aeruginosa*), *Salmonella* (e.g. *S. typhimurium, S. typhi*). Bacteria also include, but are not limited to, photosynthetic bacteria (e.g. green non-sulfur bacteria (e.g. Choroflexus, Chloronema), green sulfur bacteria (e.g. *Chlorobium*, Pelodictyon), purple sulfur bacteria (e.g. *Chromatium*), and purple non-sulfur bacteria (e.g. *Rhodospirillum, Rhodobacter*, and Rhodomicrobium).

An eukaryotic host cell includes, but is not limited to, a yeast host cell, a nematode host cell, a fungal host cell, an amoeba host cell, an avian host cell, an amphibian host cell, a reptilian host cell, an algal host cell, a mammalian host cell and an insect host cell.

Suitable host cells are discussed further in Goeddel, Gene Expression Technology: Methods in Enzymology 185, Academic Press, San Diego, Calif. (1990).

Representative examples of appropriate host cells are described below. Appropriate culture mediums and conditions for the below-described host cells are known in the art.

In a preferred embodiment the host cells are fungal cells, preferably filamentous fungal cells, more preferably *Rasamsonia* cells, most preferred *Rasamsonia emersonii* cells.

"Filamentous fungi" are herein defined as eukaryotic microorganisms that include all filamentous forms of the subdivision Eumycotina and Oomycota (as defined by Hawksworth et al., 1995). Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocallimastix, Neurospora, Paecilomyces, Penicillium, Piromyces, Phanerochaete* Podospora, Pycnoporus, *Rhizopus, Schizophyllum, Sordaria, Talaromyces, Rasamsonia, Thermoascus, Thielavia, Tolypocladium, Trametes* and *Trichoderma*. Preferred filamentous fungal strains that may serve as host cells belong to the species *Aspergillus* niger, *Aspergillus* oryzae, *Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora* thermophyla.

Preferred yeast host cells may be selected from the genera: *Saccharomyces* (e.g. *S. cerevisiae, S. bayanus, S. pastorianus, S. carlsbergensis*), *Kluyveromyces, Candida* (e.g. *C. revkaufi, C. pulcherrima, C. tropicalis, C. utilis*), *Pichia* (e.g. *P. pastoris*), *Schizosaccharomyces, Hansenula, Kloeckera, Schwanniomyces*, and *Yarrowia* (e.g. *Y. lipolytica* (formerly classified as *Candida lipolytica*)).

Examples of insect cells, include, but are not limited to, *Drosophila, Spodoptera* and Trichoplusa. Examples of nematode cells, include, but are not limited to, *C. elegans* cells. Examples of amphibian cells, include, but are not limited to, *Xenopus laevis* cells). Examples of mammalian cells, include, but are not limited to, NIH3T3, 293, CHO, COS, VERO, C127, BHK, Per-C6, Bowes melanoma and HeLa cells.

In the context of the present application, the "parent host cell" and the "mutant host cell" may be any type of host cell. The specific embodiments of the mutant host cell are described below. It will be clear to those skilled in the art that embodiments applicable to the mutant host cell are as well applicable to the parent host cell, unless otherwise indicated.

The polynucleotide may be heterologous to the genome of the host cell. The term "heterologous" as used herein refers to nucleotide or amino acid sequences not naturally occurring in a host cell. In other words, the nucleotide or amino acid sequence is not identical to that naturally found in the host cell. As used herein, the term "endogenous" or "homologous" refers to a nucleotide or amino acid sequence naturally-occurring in a host. In another embodiment, the application features host cells, e.g. transformed host cells or recombinant host cells that contain a nucleic acid encompassed by the application. A "transformed cell" or "recombinant cell" is a cell into which (or into an ancestor of which) has been introduced, by means of recombinant DNA techniques, a polynucleotide as described herein, a nucleic acid construct as described herein and/or a vector as described herein.

As used herein, the terms "transformed" or "transgenic" with reference to a cell mean that the cell has a non-native (heterologous) nucleotide sequence integrated into its genome or has an episomal plasmid that is maintained through multiple generations. The term is synonymous with the term "recombinant" or "genetically modified". A host cell can be chosen that modulates the expression of the inserted sequences or modifies and methods the gene product in a specific, desired fashion. Such modifications (e.g. glycosylation) and methoding (e.g. cleavage) of polypeptide products may facilitate optimal functioning of the polypeptides.

Various host cells have characteristic and specific mechanisms for post-translational methoding and modification of polypeptides and gene products. Appropriate cell lines or host systems familiar to those of skill in the art of molecular biology and/or microbiology can be chosen to ensure the desired and correct modification and methoding of the foreign polypeptide expressed. To this end, eukaryotic host cells that possess the cellular machinery for proper methoding of the primary transcript, glycosylation, and phosphorylation of the gene product can be used. Such host cells are well-known in the art.

A host cell as defined herein is an organism suitable for genetic manipulation and one which may be cultured at cell densities useful for industrial production of a target product. A suitable organism may be a microorganism, for example one which may be maintained in a fermentation device. A host cell may be a host cell found in nature or a host cell derived from a parent host cell after genetic manipulation or classical mutagenesis.

According to an embodiment, when the mutant host cell as described herein is a filamentous fungal host cell, the mutant host cell may comprise one or more modifications in its genome such that the mutant host cell is deficient in the production of at least one product selected from glucoamylase (glaA), acid stable alpha-amylase (amyA), neutral alpha-amylase (amyBI and amyBII), oxalic acid hydrolase (oahA), a toxin, preferably ochratoxin and/or fumonisin, a protease transcriptional regulator prtT, PepA, a product encoded by the gene hdfA and/or hdfB, a non-ribosomal peptide synthase npsE if compared to a parent host cell and measured under the same conditions.

Therefore, when the mutant microbial host cell as described herein is a filamentous fungal host cell, the host cell may comprise one or more modifications in its genome to result in a deficiency in the production of the major extracellular aspartic protease PepA. For example, the host cell as described herein may further comprise a disruption of the pepA gene encoding the major extracellular aspartic protease PepA.

When the mutant microbial host cell as described herein is a filamentous fungal host cell, the host cell as described herein may additionally comprises one or more modifications in its genome to result in a deficiency in the production of the product encoded by the hdfA (Ku70) and/or hdfB (Ku80) gene. For example, the host cell as described herein may further comprise a disruption of the hdfA and/or hdfB gene.

When the mutant host cell as described herein is a filamentous fungal host cell, the host cell as described herein may additionally comprise a modification in its genome which results in the deficiency in the production of the non-ribosomal peptide synthase npsE.

Host cells as described herein include plant cells and the application therefore extends to transgenic organisms, such as plants and parts thereof, which contain one or more cells as described herein. The cells may heterologous express the variant polypeptide as described herein or may heterologous contain one or more of the polynucleotides as described herein. The transgenic (or genetically modified) plant may therefore have inserted (e.g. stably) into its genome a sequence encoding one or more of the variant polypeptides as described herein. The transformation of plant cells can be performed using known techniques.

In an embodiment the gene encoding for the endogenous and/or parent beta-glucosidase is deleted or modified in such a way that the endogenous and/or parent beta-glucosidase polypeptide is no longer produced by the host cells as described herein. Consequently, instead of the endogenous and/or parent beta-glucosidase the variant polypeptide as described herein may be produced by the host cells. In other words, the present application also provides a host cell wherein the gene encoding the beta-glucosidase comprising the amino acid sequence of SEQ ID NO: 2 has been deleted or modified in such a way that the beta-glucosidase polypeptide is no longer produced by the host cells. Such host cells may comprise the polynucleotide that encodes a variant polypeptide as described herein instead and produce said variant beta-glucosidase.

The present application also provides a host cell wherein the gene encoding the beta-glucosidase comprising the amino acid sequence of SEQ ID NO: 4 has been deleted or modified in such a way that the beta-glucosidase polypeptide is no longer produced by the host cells. Such host cells may comprise the polynucleotide that encodes a variant polypeptide as described herein instead and produce said variant beta-glucosidase.

Polypeptide Production

The application also relates to a method for producing a variant polypeptide as described herein, which method comprises the steps of (a) cultivating a host cell as described herein under conditions conducive to the production of the variant polypeptide as described herein, and (b) optionally, recovering the variant polypeptide as described herein.

The host cells as described herein may be cultured using procedures known in the art. For each combination of a promoter and a host cell, culture conditions are available which are conducive to the expression of the polynucleotide sequence encoding the variant polypeptide as described herein. After reaching the desired cell density or titer of the polypeptide, the culture is stopped and the polypeptide is recovered using known procedures. Alternatively, the polypeptide may not be recovered by used in the form of a whole fermentation broth, either killed of or not killed of. The broth may comprise other constituents next to the variant polypeptide as described herein such as cells or parts thereof, culture medium components, to name just a few.

The fermentation medium can comprise a known culture medium containing a carbon source, a nitrogen source, and an inorganic nutrient sources. Optionally, an inducer may be included.

The selection of the appropriate medium may be based on the choice of expression host and/or based on the regulatory requirements of the nucleic acid construct. Such media are known to those skilled in the art. The medium may, if desired, contain additional components favoring the transformed host cell over other potentially contaminating microorganisms.

The fermentation can be performed over a period of from about 0.5 to about 30 days. It may be a batch, continuous or fed-batch method, suitably at a temperature in the range of 0 to 100° C. or 0 to 80° C., for example from 0 to 50° C. and/or at a pH from 2 to 10. Preferred fermentation conditions are a temperature in the range of from 20° C. to 45° C. and/or at a pH of from 3 to 9. The appropriate conditions are usually selected based on the choice of the host cell and the polypeptide to be expressed.

After fermentation, if necessary, the cells can be removed from the fermentation broth by means of centrifugation or filtration. After fermentation has stopped or after removal of the cells, the avariant polypeptide as described herein may then be recovered and, if desired, purified and isolated by conventional means.

The variant polypeptide as described herein can be recovered and purified from recombinant host cell cultures by methods known in the art. Most preferably, high performance liquid chromatography ("HPLC") is employed for purification.

If desired, a host cell as described above may be used to in the preparation of a variant polypeptide as described herein. Such a method typically comprises cultivating a host cell (e.g. transformed or transfected with an nucleic acid construct as described above) under conditions to provide for expression of a coding sequence encoding the polypeptide, and optionally recovering the expressed polypeptide. Polynucleotides as descreibed herein can be incorporated into a recombinant replicable vector, e.g. an expression vector. The vector may be used to replicate the nucleic acid in a compatible host cell. Thus in a further embodiment, the application provides a method of making a polynucleotide as described herein by introducing a polynucleotide as described herein into a replicable vector, introducing the vector into a compatible host cell, and growing the host cell under conditions which bring about the replication of the vector. The vector may be recovered from the host cell.

Preferably, the polypeptide is produced as a secreted protein in which case the nucleotide sequence encoding the polypeptide in the expression construct is operably linked to a nucleotide sequence encoding a signal sequence. Preferably, the signal sequence is native (homologous) to the nucleotide sequence encoding the polypeptide. Alternatively, the signal sequence is foreign (heterologous) to the nucleotide sequence encoding the polypeptide, in which case the signal sequence is preferably endogenous to the host cell in which the nucleotide sequence as described herein is expressed.

In an embodiment the variant polypeptides as described herein may be overexpressed in a host cell compared to the parent host cell in which the polypeptide is not overexpressed. Overexpression of a polypeptide is defined herein as the expression of the polypeptide which results in an activity of the polypeptide in the host cell being at least 1.1-, at least 1.25- or at least 1.5-fold the activity of the polypeptide in the parent host cell wherein the polypeptide is not overexpressed.

Preferably, the activity of the polypeptide is at least 2-fold, more preferably at least 3-fold, more preferably at least 4-fold, more preferably at least 5-fold, even more preferably at least 10-fold and most preferably at least 20-fold the activity of the polypeptide in the parent host cell.

Transformation of the host cell may be conducted by any suitable known methods, including electroporation methods, particle bombardment or micro projectile bombardment, protoplast methods and *Agrobacterium* mediated transformation (AMT).

In order to enhance the amount of copies of the polynucleotide coding for the polypeptide or coding for a compound involved in the production by the cell of the polypeptide in the mutated host cell, multiple transformations of the host cell may be required. In this way, the ratios of the different polypeptides produced by the host cell may be influenced. Also, an expression vector may comprise multiple expression cassettes to increase the amount of copies of the polynucleotide(s) to be transformed.

Another way could be to choose different control sequences for the different polynucleotides, which—depending on the choice—may cause a higher or a lower production of the desired polypeptide(s).

The host cells transformed with the selectable marker can be selected based on the presence of the selectable marker.

For stable transfection of mammalian cells, it is known that, depending upon the expression vector and transfection technique used, only a small fraction of cells may integrate the foreign polynucleotide into their genome. In order to identify and select these integrants, a gene that encodes a selectable marker (e.g. resistance to antibiotics) is generally introduced into the host cells along with the polynucleotide of interest. Preferred selectable markers include, but are not limited to, those which confer resistance to drugs or which complement a defect in the host cell. The selectable marker may be introduced into the cell on the expression vector as the expression cassette or may be introduced on a separate expression vector.

Preferred selectable markers include, but are not limited to, those which confer resistance to drugs or which complement a defect in the host cell. Alternatively, specific selection markers can be used such as auxotrophic markers which require corresponding mutant host cells. In a preferred embodiment the selection marker is deleted from the transformed host cell after introduction of the expression construct, so as to obtain transformed host cells which are free of selection marker genes. As indicated, the expression vectors will preferably contain selectable markers. Vectors preferred for use in bacteria are for example disclosed in WO 2004/074468. Other suitable vectors will be readily apparent to the skilled artisan.

Compositions

The variant polypeptide as described herein may be comprised in a composition. Preferably, the composition is enriched in the polypeptide. By "enriched" is meant that the polypeptide in the composition is increased, for example with at least a factor of 1.1, preferably 1.5, more preferably 2 on protein level compared to the composition without the overexpressed variant polypeptide as described herein. The composition may comprise a variant polypeptide as described herein as the major enzymatic component, e.g. a mono-component composition. Alternatively, the composition may comprise multiple enzymatic activities. The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art. The dosage of the composition as described herein and other conditions under which the composition is used depend on the ultimate use of the composition.

The application is concerned with a composition comprising (a) a variant polypeptide as described herein, and (b) a cellulase and/or a hemicellulase and/or a pectinase.

In an embodiment the cellulase is selected from the group consisting of lytic polysaccharide monooxygenase, a cellobiohydrolase I, a cellobiohydrolase II, an endo-beta-1,4-glucanase, a beta-glucosidase, a beta-(1,3)(1,4)-glucanase and any combination thereof. In an embodiment the hemicellulase is selected from the group consisting of an endoxylanase, a beta-xylosidase, an alpha-L-arabinofuranosidase, an alpha-D-glucuronidase, an acetyl-xylan esterase, a feruloyl esterase, a coumaroyl esterase, an alpha-galactosidase, a beta-galactosidase, a beta-mannanase, a beta-mannosidase and any combination thereof. Of course, the composition may also comprise more than one cellulase and/or more than one hemicellulase and/or more than one pectinase. For example, two cellulases, two hemicellulases and one pectinase or five cellulases, one hemicellulose and three pectinases. Any combination is possible. Suitable cellulases and/or hemicellulases and/or pectinases are described herein.

Polypeptides can be produced by different methods and mixed into an optimal composition or the compositions can be made directly as a mixture by one fermentation.

A composition as described herein may comprise one, two or three or more classes of cellulase, for example a polypeptide as described herein, an endo-1,4-β-glucanase (EG), an exo-cellobiohydrolase (CBH) and a lytic polysaccharide monooxygenase (LPMO).

A composition as described herein may comprise a polypeptide which has the same enzymatic activity, for example the same type of cellulose and/or hemicellulase and/or pectinase activity as that provided by the variant polypeptide as described herein.

A composition as described herein may comprise a polypeptide which has a different type of cellulase activity and/or hemicellulase activity and/or pectinase activity than that provided by the variant polypeptide as described herein. For example, a composition as described herein may comprise one type of cellulase and/or hemicellulase activity and/or pectinase activity provided by a variant polypeptide as described herein and a second type of cellulase and/or hemicellulase activity and/or pectinase activity provided by an additional cellulose/hemicellulase/pectinase.

Herein, a cellulase is any polypeptide which is capable of degrading and/or hydrolysing cellulose or enhancing the degradation and/or hydrolysis of cellulose. A polypeptide which is capable of degrading cellulose is a polypeptide which is capable of catalysing the method of breaking down cellulose into smaller units, either partially, for example into cellodextrins, or completely into glucose monomers. Degradation will typically take place by a hydrolysis reaction.

Herein, a hemicellulase is any polypeptide which is capable of degrading and/or hydrolysing hemicellulose or enhancing the degradation and/or hydrolysis of hemicellulose. That is to say, a hemicellulase may be capable of degrading one or more of xylan, glucuronoxylan, arabinoxylan, glucomannan and xyloglucan. A polypeptide which is capable of degrading a hemicellulose is a polypeptide which is capable of catalysing the method of breaking down the hemicellulose into smaller polysaccharides, either partially, for example into oligosaccharides, or completely into sugar monomers, for example hexose or pentose sugar monomers. A hemicellulase may give rise to a mixed population of oligosaccharides and sugar monomers. Degradation will typically take place by a hydrolysis reaction.

Herein, a pectinase is any polypeptide which is capable of degrading pectin. A polypeptide which is capable of degrading pectin is a polypeptide which is capable of catalysing the method of breaking down pectin into smaller units, either partially, for example into oligosaccharides, or completely into sugar monomers. A pectinase as described herein may give rise to a mixed population of oligosaccharides and sugar monomers. Degradation will typically take place by a hydrolysis reaction.

The composition may comprise a cellulase and/or a hemicellulase and/or a pectinase from *Rasamsonia* or a source other than *Rasamsonia*. They may be used together with one or more *Rasamsonia* enzymes or they may be used without additional *Rasamsonia* enzymes being present.

The composition as described herein may comprise a beta-glucosidase. For example, the composition as described herein may comprise a beta-glucosidase (BG) from *Aspergillus*, such as *Aspergillus oryzae*, such as the one disclosed in WO 02/095014 or the fusion protein having beta-glucosidase activity disclosed in WO 2008/057637, or *Aspergillus fumigatus*, such as the one disclosed as SEQ ID NO:2 in WO 2005/047499 or SEQ ID NO:5 in WO 2014/130812 or an *Aspergillus fumigatus* beta-glucosidase variant, such as one disclosed in WO 2012/044915, such as one with the following substitutions: F100D, S283G, N456E, F512Y (using SEQ ID NO: 5 in WO 2014/130812 for numbering), or *Aspergillus* aculeatus, *Aspergillus niger* or *Aspergillus kawachi*. In another embodiment the beta-glucosidase is derived from *Penicillium*, such as *Penicillium brasilianum* disclosed as SEQ ID NO:2 in WO 2007/019442, or from *Trichoderma*, such as *Trichoderma reesei*, such as ones described in U.S. Pat. Nos. 6,022,725, 6,982,159, 7,045,332, 7,005,289, US 2006/0258554 US 2004/0102619. In an embodiment even a bacterial beta-glucosidase can be used. In another embodiment the beta-glucosidase is derived from *Thielavia terrestris* (WO 2011/035029) or *Trichophaea saccata* (WO 2007/019442). In a preferred embodiment the enzyme composition comprises a beta-glucosidase from *Rasamsonia*, such as *Rasamsonia emersonii* (see WO 2012/000886).

The composition as described herein may comprise an endoglucanase. For example, the composition as described herein may comprise an endoglucanase (EG) from *Trichoderma*, such as *Trichoderma reesei*; from *Humicola*, such as a strain of *Humicola insolens*; from *Aspergillus*, such as *Aspergillus aculeatus* or *Aspergillus kawachii*; from *Erwinia*, such as *Erwinia* carotovara; from *Fusarium*, such as *Fusarium oxysporum*; from *Thielavia*, such as *Thielavia terrestris*; from *Humicola*, such as *Humicola grisea* var. *thermoidea* or *Humicola insolens*; from *Melanocarpus*, such as *Melanocarpus albomyces*; from *Neurospora*, such as *Neurospora crassa*; from *Myceliophthora*, such as *Myceliophthora thermophila*; from *Cladorrhinum*, such as *Cladorrhinum foecundissimum* and/or from *Chrysosporium*, such as a strain of *Chrysosporium lucknowense*. In an embodiment even a bacterial endoglucanase can be used including, but are not limited to, *Acidothermus cellulolyticus* endoglucanase (see WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (see WO 05/093050); and *Thermobifida fusca* endoglucanase V (see WO 05/093050). In a preferred embodiment the endoglucanase is from *Rasamsonia*, such as *Rasamsonia emersonii* (see WO 01/70998).

The composition as described herein may comprise a cellobiohydrolase I. For example, the composition as described herein may comprise a cellobiohydrolase I from *Aspergillus*, such as *Aspergillus fumigatus*, such as the Cel7A CBH I disclosed in SEQ ID NO:6 in WO 2011/057140 or SEQ ID NO:6 in WO 2014/130812, or from *Trichoderma*, such as *Trichoderma reesei*. In a preferred embodiment the enzyme composition comprises a cellobiohydrolase I from *Rasamsonia*, such as *Rasamsonia emersonii* (see WO 2010/122141).

The composition as described herein may comprise a cellobiohydrolase II. For example, the composition as described herein may comprise a cellobiohydrolase II from *Aspergillus*, such as *Aspergillus fumigatus*, such as the one in SEQ ID NO:7 in WO 2014/130812 or from *Trichoderma*, such as *Trichoderma reesei*, or from *Thielavia*, such as *Thielavia terrestris*, such as cellobiohydrolase II CEL6A from *Thielavia terrestris*. In a preferred embodiment the enzyme composition comprises a cellobiohydrolase II from *Rasamsonia*, such as *Rasamsonia emersonii* (see WO 2011/098580).

For example, the composition as described herein may comprise a polypeptide having cellulolytic enhancing activity such as a lytic polysaccharide monooxygenase from *Thermoascus*, such as *Thermoascus aurantiacus*, such as the one described in WO 2005/074656 as SEQ ID NO:2 and SEQ ID NO:1 in WO2014/130812 and in WO 2010/065830; or from *Thielavia*, such as *Thielavia terrestris*, such as the one described in WO 2005/074647 as SEQ ID NO: 8 or SEQ ID NO:4 in WO2014/130812 and in WO 2008/148131, and WO 2011/035027; or from *Aspergillus*, such as *Aspergillus fumigatus*, such as the one described in WO 2010/138754 as SEQ ID NO:2 or SEQ ID NO: 3 in WO2014/130812; or from *Penicillium*, such as *Penicillium emersonii*, such as the one disclosed as SEQ ID NO:2 in WO 2011/041397 or SEQ ID NO:2 in WO2014/130812.

Other suitable polypeptides having cellulolytic enhancing activity such as a lytic polysaccharide monooxygenases include, but are not limited to, *Trichoderma reesei* (see WO 2007/089290), *Myceliophthora thermophila* (see WO 2009/085935, WO 2009/085859, WO 2009/085864, WO 2009/085868), *Penicillium pinophilum* (see WO 2011/005867), *Thermoascus* sp. (see WO 2011/039319), and *Thermoascus crustaceous* (see WO 2011/041504). In a preferred embodiment, the lytic polysaccharide monooxygenase is from *Rasamsonia*, e.g. *Rasamsonia emersonii* (see WO 2012/000892). In one aspect, the polypeptide having cellulolytic enhancing activity such as a lytic polysaccharide monooxygenase is used in the presence of a soluble activating divalent metal cation according to WO 2008/151043, e.g. manganese sulfate. In one aspect, the polypeptide having cellulolytic enhancing activity such as a lytic polysaccharide monooxygenase is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover.

Other cellulolytic enzymes that may be comprised in the composition as described herein are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648, 263, and 5,686,593, to name just a few.

In addition, the composition as described herein may comprise an endoxylanase. Examples of endoxylanases that may be comprised in the composition as described herein include, but are not limited to, endoxylanases from *Aspergillus aculeatus* (see WO 94/21785), *Aspergillus fumigatus* (see WO 2006/078256), *Penicillium pinophilum* (see WO 2011/041405), *Penicillium* sp. (see WO 2010/126772), *Thielavia terrestris* NRRL 8126 (see WO 2009/079210), and *Trichophaea saccata* GH10 (see WO 2011/057083). In a preferred embodiment the enzyme composition comprises an endoxylanase from *Rasamsonia*, such as *Rasamsonia emersonii* (see WO 02/24926).

In addition, the composition as described herein may comprise a beta-xylosidase. Examples of beta-xylosidases that may be comprised in the composition as described herein include, but are not limited to, beta-xylosidases from *Neurospora crassa* and *Trichoderma reesei*. In a preferred embodiment the enzyme composition comprises a beta-xylosidase from *Rasamsonia*, such as *Rasamsonia emersonii* (see WO 2014/118360).

In addition, the composition as described herein may comprise an acetylxylan esterase. Examples of acetylxylan esterases that may be comprised in the enzyme composition include, but are not limited to, acetylxylan esterases from *Aspergillus aculeatus* (see WO 2010/108918), *Chaetomium globosum*, *Chaetomium gracile*, *Humicola insolens* DSM 1800 (see WO 2009/073709), *Hypocrea jecorina* (see WO 2005/001036), *Myceliophtera thermophila* (see WO 2010/014880), *Neurospora crassa*, *Phaeosphaeria nodorum* and *Thielavia terrestris* NRRL 8126 (see WO 2009/042846). Examples of feruloyl esterases (ferulic acid esterases) that may be comprised in the enzyme composition include, but are not limited to, feruloyl esterases form *Humicola insolens* DSM 1800 (see WO 2009/076122), *Neosartorya fischeri*, *Neurospora crassa*, *Penicillium* aurantiogriseum (see WO 2009/127729), and *Thielavia terrestris* (see WO 2010/053838 and WO 2010/065448). Examples of arabinofuranosidases that may be comprised in the enzyme composition include, but are not limited to, arabinofuranosidases from *Aspergillus niger*, *Humicola insolens* DSM 1800 (see WO 2006/114094 and WO 2009/073383) and *M. giganteus* (see WO 2006/114094). Examples of alpha-glucuronidases that may be comprised in the enzyme composition include, but are not limited to, alpha-glucuronidases from *Aspergillus clavatus*, *Aspergillus fumigatus*, *Aspergillus niger*, *Aspergillus terreus*, *Humicola insolens* (see WO 2010/014706), *Penicillium* aurantiogriseum (see WO 2009/068565) and *Trichoderma reesei*.

A composition as described herein may comprise one, two, three, four classes or more of cellulase, for example one, two, three or four or all of a lytic polysaccharide monooxygenase (LPMO), an endoglucanase (EG), one or two exo-cellobiohydrolases (CBH) and a beta-glucosidase (BG). An enzyme composition as described herein may comprise two or more of any of these classes of cellulase.

A composition as described herein may comprise one type of cellulase activity and/or hemicellulase activity and/or pectinase activity provided by a composition as described herein and a second type of cellulase activity and/or hemicellulase activity and/or pectinase activity provided by an additional cellulase/hemicellulase/pectinase. Accordingly, a composition as described herein may comprise any cellulase, for example, a lytic polysaccharide monooxygenase, a cellobiohydrolase, an endo-beta-1,4-glucanase, a beta-glucosidase or a beta-(1,3)(1,4)-glucanase.

In an embodiment a composition as described herein comprises a variant polypeptide as described herein, an endoglucanase, a beta-glucosidase, a cellobiohydrolase I, a cellobiohydrolase II, an endoxylanase, a beta-xylosidase, and a lytic polysaccharide monooxygenase.

As used herein, a cellobiohydrolase (EC 3.2.1.91) is any polypeptide which is capable of catalyzing the hydrolysis of 1,4-beta-D-glucosidic linkages in cellulose or cellotetraose, releasing cellobiose from the ends of the chains. This enzyme may also be referred to as cellulase 1,4-beta-cellobiosidase, 1,4-beta-cellobiohydrolase, 1,4-beta-D-glucan cellobiohydrolase, avicelase, exo-1,4-beta-D-glucanase, exocellobiohydrolase or exoglucanase.

As used herein, an endo-beta-1,4-glucanase (EC 3.2.1.4) is any polypeptide which is capable of catalyzing the endohydrolysis of 1,4-beta-D-glucosidic linkages in cellulose, lichenin or cereal beta-D-glucans. Such a polypeptide may also be capable of hydrolyzing 1,4-linkages in beta-D-glucans also containing 1,3-linkages. This enzyme may also be referred to as cellulase, avicelase, beta-1,4-endoglucan hydrolase, beta-1,4-glucanase, carboxymethyl cellulase, celludextrinase, endo-1,4-beta-D-glucanase, endo-1,4-beta-D-glucanohydrolase, endo-1,4-beta-glucanase or endoglucanase.

As used herein, a beta-glucosidase (EC 3.2.1.21) is any polypeptide which is capable of catalysing the hydrolysis of terminal, non-reducing beta-D-glucose residues with release of beta-D-glucose. Such a polypeptide may have a wide specificity for beta-D-glucosides and may also hydrolyze one or more of the following: a beta-D-galactoside, an alpha-L-arabinoside, a beta-D-xyloside or a beta-D-fucoside. This enzyme may also be referred to as amygdalase, beta-D-glucoside glucohydrolase, cellobiase or gentobiase.

As used herein, a beta-(1,3)(1,4)-glucanase (EC 3.2.1.73) is any polypeptide which is capable of catalysing the hydrolysis of 1,4-beta-D-glucosidic linkages in beta-D-glucans containing 1,3- and 1,4-bonds. Such a polypeptide may act on lichenin and cereal beta-D-glucans, but not on beta-D-glucans containing only 1,3- or 1,4-bonds. This enzyme may also be referred to as licheninase, 1,3-1,4-beta-D-glucan 4-glucanohydrolase, beta-glucanase, endo-beta-1,3-1,4 glucanase, lichenase or mixed linkage beta-glucanase. An alternative for this type of enzyme is EC 3.2.1.6, which is described as endo-1,3(4)-beta-glucanase. This type of enzyme hydrolyses 1,3- or 1,4-linkages in beta-D-glucanse when the glucose residue whose reducing group is involved in the linkage to be hydrolysed is itself substituted at C-3. Alternative names include endo-1,3-beta-glucanase, laminarinase, 1,3-(1,3;1,4)-beta-D-glucan 3 (4) glucanohydrolase. Substrates include laminarin, lichenin and cereal beta-D-glucans.

A composition as described herein may comprise any hemicellulase, for example, an endoxylanase, a beta-xylosidase, a alpha-L-arabionofuranosidase, an alpha-D-glucuronidase, an acetyl xylan esterase, a feruloyl esterase, a coumaroyl esterase, an alpha-galactosidase, a beta-galactosidase, a beta-mannanase or a beta-mannosidase.

As used herein, an endoxylanase (EC 3.2.1.8) is any polypeptide which is capable of catalysing the endohydrolysis of 1,4-beta-D-xylosidic linkages in xylans. This enzyme may also be referred to as endo-1,4-beta-xylanase or 1,4-beta-D-xylan xylanohydrolase. An alternative is EC 3.2.1.136, a glucuronoarabinoxylan endoxylanase, an enzyme that is able to hydrolyze 1,4-xylosidic linkages in glucuronoarabinoxylans.

As used herein, a beta-xylosidase (EC 3.2.1.37) is any polypeptide which is capable of catalysing the hydrolysis of 1,4-beta-D-xylans, to remove successive D-xylose residues from the non-reducing termini. Such enzymes may also hydrolyze xylobiose. This enzyme may also be referred to as xylan 1,4-beta-xylosidase, 1,4-beta-D-xylan xylohydrolase, exo-1,4-beta-xylosidase or xylobiase.

As used herein, an alpha-L-arabinofuranosidase (EC 3.2.1.55) is any polypeptide which is capable of acting on alpha-L-arabinofuranosides, alpha-L-arabinans containing (1,2)- and/or (1,3)- and/or (1,5)-linkages, arabinoxylans and arabinogalactans. This enzyme may also be referred to as alpha-N-arabinofuranosidase, arabinofuranosidase or arabinosidase.

As used herein, an alpha-D-glucuronidase (EC 3.2.1.139) is any polypeptide which is capable of catalysing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyse 4-O-methylated glucoronic acid, which can also be present as a substituent in xylans. An alternative is EC 3.2.1.131: xylan alpha-1,2-glucuronosidase, which catalyses the hydrolysis of alpha-1,2-(4-O-methyl)glucuronosyl links.

As used herein, an acetyl xylan esterase (EC 3.1.1.72) is any polypeptide which is capable of catalysing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacetylglycerol. Such a polypeptide typically does not act on acetylated mannan or pectin.

As used herein, a feruloyl esterase (EC 3.1.1.73) is any polypeptide which is capable of catalysing a reaction of the form: feruloyl-saccharide+H$_2$O=ferulate+saccharide. The saccharide may be, for example, an oligosaccharide or a polysaccharide. It may typically catalyse the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin.

As used herein, a coumaroyl esterase (EC 3.1.1.73) is any polypeptide which is capable of catalysing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

As used herein, an alpha-galactosidase (EC 3.2.1.22) is any polypeptide which is capable of catalysing the hydrolysis of terminal, non-reducing alpha-D-galactose residues in alpha-D-galactosides, including galactose oligosaccharides, galactomannans, galactans and arabinogalactans. Such a polypeptide may also be capable of hydrolyzing alpha-D-fucosides. This enzyme may also be referred to as melibiase.

As used herein, a beta-galactosidase (EC 3.2.1.23) is any polypeptide which is capable of catalysing the hydrolysis of terminal non-reducing beta-D-galactose residues in beta-D-galactosides. Such a polypeptide may also be capable of hydrolyzing alpha-L-arabinosides. This enzyme may also be referred to as exo-(1→4)-beta-D-galactanase or lactase.

As used herein, a beta-mannanase (EC 3.2.1.78) is any polypeptide which is capable of catalysing the random hydrolysis of 1,4-beta-D-mannosidic linkages in mannans, galactomannans and glucomannans. This enzyme may also be referred to as mannan endo-1,4-beta-mannosidase or endo-1,4-mannanase.

As used herein, a beta-mannosidase (EC 3.2.1.25) is any polypeptide which is capable of catalysing the hydrolysis of terminal, non-reducing beta-D-mannose residues in beta-D-mannosides. This enzyme may also be referred to as mannanase or mannase.

A composition as described herein may comprise any pectinase, for example an endo-polygalacturonase, a pectin methyl esterase, an endo-galactanase, a beta-galactosidase, a pectin acetyl esterase, an endo-pectin lyase, pectate lyase, alpha-rham nosidase, an exo-galacturonase, an expolygalacturonate lyase, a rhamnogalacturonan hydrolase, a rhamnogalacturonan lyase, a rhamnogalacturonan acetyl esterase, a rhamnogalacturonan galacturonohydrolase, a xylogalacturonase.

As used herein, an endo-polygalacturonase (EC 3.2.1.15) is any polypeptide which is capable of catalysing the random hydrolysis of 1,4-alpha-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-alpha-1,4-galacturonide glycanohydrolase, endogalacturonase; endo-D-galacturonase or poly(1,4-alpha-D-galacturonide) glycanohydrolase.

As used herein, a pectin methyl esterase (EC 3.1.1.11) is any enzyme which is capable of catalysing the reaction: pectin+n H$_2$O=n methanol+pectate. The enzyme may also been known as pectinesterase, pectin demethoxylase, pectin methoxylase, pectin methylesterase, pectase, pectinoesterase or pectin pectylhydrolase.

As used herein, an endo-galactanase (EC 3.2.1.89) is any enzyme capable of catalysing the endohydrolysis of 1,4-beta-D-galactosidic linkages in arabinogalactans. The enzyme may also be known as arabinogalactan endo-1,4-beta-galactosidase, endo-1,4-beta-galactanase, galactanase, arabinogalactanase or arabinogalactan 4-beta-D-galactanohydrolase.

As used herein, a pectin acetyl esterase is defined herein as any enzyme which has an acetyl esterase activity which catalyses the deacetylation of the acetyl groups at the hydroxyl groups of GalUA residues of pectin.

As used herein, an endo-pectin lyase (EC 4.2.2.10) is any enzyme capable of catalysing the eliminative cleavage of (1→4)-α-D-galacturonan methyl ester to give oligosaccharides with 4-deoxy-6-O-methyl-alpha-D-galact-4-enuronosyl groups at their non-reducing ends. The enzyme may also be known as pectin lyase, pectin trans-eliminase; endopectin lyase, polymethylgalacturonic transeliminase, pectin methyltranseliminase, pectolyase, PL, PNL or PMGL or (1→4)-6-O-methyl-alpha-D-galacturonan lyase.

As used herein, a pectate lyase (EC 4.2.2.2) is any enzyme capable of catalysing the eliminative cleavage of (1→4)-alpha-D-galacturonan to give oligosaccharides with 4-deoxy-alpha-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, alpha-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-alpha-D-galacturonan lyase.

As used herein, an alpha-rhamnosidase (EC 3.2.1.40) is any polypeptide which is capable of catalysing the hydrolysis of terminal non-reducing alpha-L-rhamnose residues in alpha-L-rhamnosides or alternatively in rhamnogalacturonan. This enzyme may also be known as alpha-L-rhamnosidase T, alpha-L-rhamnosidase N or alpha-L-rhamnoside rhamnohydrolase.

As used herein, exo-galacturonase (EC 3.2.1.82) is any polypeptide capable of hydrolysis of pectic acid from the non-reducing end, releasing digalacturonate. The enzyme may also be known as exo-poly-alpha-galacturonosidase, exo-polygalacturonosidase or exo-polygalacturanosidase.

As used herein, exo-galacturonase (EC 3.2.1.67) is any polypeptide capable of catalysing: (1,4-alpha-D-galacturonide)$_n$+H$_2$O=(1,4-alpha-D-galacturonide)$_{n-1}$+D-galacturonate. The enzyme may also be known as galacturan 1,4-alpha-galacturonidase, exopolygalacturonase, poly (galacturonate) hydrolase, exo-D-galacturonase, exo-D-galacturonanase, exo-poly-D-galacturonase or poly(1,4-alpha-D-galacturonide) galacturonohydrolase.

As used herein, exopolygalacturonate lyase (EC 4.2.2.9) is any polypeptide capable of catalysing eliminative cleavage of 4-(4-deoxy-alpha-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-alpha-D-galacturonan reducing-end-disaccharide-lyase.

As used herein, rhamnogalacturonan hydrolase is any polypeptide which is capable of hydrolyzing the linkage between galactosyluronic acid and rhamnopyranosyl in an endo-fashion in strictly alternating rhamnogalacturonan structures, consisting of the disaccharide [(1,2)-alpha-L-rhamnoyl-(1,4)-alpha-galactosyluronic acid].

As used herein, rhamnogalacturonan lyase is any polypeptide which is any polypeptide which is capable of cleaving alpha-L-Rhap-(1→4)-alpha-D-GalpA linkages in an endo-fashion in rhamnogalacturonan by beta-elimination.

As used herein, rhamnogalacturonan acetyl esterase is any polypeptide which catalyzes the deacetylation of the backbone of alternating rhamnose and galacturonic acid residues in rhamnogalacturonan.

As used herein, rhamnogalacturonan galacturonohydrolase is any polypeptide which is capable of hydrolyzing galacturonic acid from the non-reducing end of strictly alternating rhamnogalacturonan structures in an exo-fashion.

As used herein, xylogalacturonase is any polypeptide which acts on xylogalacturonan by cleaving the beta-xylose substituted galacturonic acid backbone in an endo-manner. This enzyme may also be known as xylogalacturonan hydrolase.

As used herein, endo-arabinanase (EC 3.2.1.99) is any polypeptide which is capable of catalysing endohydrolysis of 1,5-alpha-arabinofuranosidic linkages in 1,5-arabinans. The enzyme may also be known as endo-arabinase, arabinan endo-1,5-alpha-L-arabinosidase, endo-1,5-alpha-L-arabinanase, endo-alpha-1,5-arabanase; endo-arabanase or 1,5-alpha-L-arabinan 1,5-alpha-L-arabinanohydrolase.

In addition, one or more (for example two, three, four or all) of an amylase, a protease, a lipase, a ligninase, a hexosyltransferase, a glucuronidase, an expansin, a cellulose induced protein or a cellulose integrating protein or like protein may be present in a composition as described herein.

"Protease" includes enzymes that hydrolyze peptide bonds (peptidases), as well as enzymes that hydrolyze bonds between peptides and other moieties, such as sugars (glycopeptidases). Many proteases are characterized under EC 3.4 and are suitable for use in the methods as described herein. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phospoglycerides, lipoproteins, diacylglycerols, and the like. In plants, lipids are used as structural components to limit water loss and pathogen infection. These lipids include waxes derived from fatty acids, as well as cutin and suberin.

"Ligninase" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.1.14), manganese peroxidases (EC 1.11.1.13), laccases (EC 1.10.3.2) and feruloyl esterases (EC 3.1.1.73).

"Hexosyltransferase" (2.4.1-) includes enzymes which are capable of catalysing a transferase reaction, but which can also catalyze a hydrolysis reaction, for example of cellulose and/or cellulose degradation products. An example of a hexosyltransferase which may be used in the application is a beta-glucanosyltransferase. Such an enzyme may be able to catalyze degradation of (1,3)(1,4)glucan and/or cellulose and/or a cellulose degradation product.

"Glucuronidase" includes enzymes that catalyze the hydrolysis of a glucoronoside, for example β-glucuronoside to yield an alcohol. Many glucuronidases have been characterized and may be suitable for use in the application, for example beta-glucuronidase (EC 3.2.1.31), hyalurono-glucuronidase (EC 3.2.1.36), glucuronosyl-disulfoglucosamine glucuronidase (3.2.1.56), glycyrrhizinate beta-glucuronidase (3.2.1.128) or alpha-D-glucuronidase (EC 3.2.1.139).

A composition as described herein may comprise an expansin or expansin-like protein, such as a swollenin (see Salheimo et al., Eur. J. Biochem. 269, 4202-4211, 2002) or a swollenin-like protein.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. For the purposes of this application, an expansin-like protein or swollenin-like protein may comprise one or both of such domains and/or may disrupt the structure of cell walls (such as disrupting cellulose structure), optionally without producing detectable amounts of reducing sugars.

A composition as described herein may comprise a cellulose induced protein, for example the polypeptide product of the cip1 or cip2 gene or similar genes (see Foreman et al., J. Biol. Chem. 278(34), 31988-31997, 2003), a cellulose/cellulosome integrating protein, for example the polypeptide product of the cipA or cipC gene, or a scaffoldin or a scaffoldin-like protein. Scaffoldins and cellulose integrating proteins are multi-functional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM) that mediates attachment of the cellulosome to its substrate. A scaffoldin or cellulose integrating protein for the purposes of this application may comprise one or both of such domains.

A composition as described herein may also comprise a catalase. The term "catalase" means a hydrogen-peroxide:hydrogen-peroxide oxidoreductase (EC 1.11.1.6 or EC 1.11.1.21) that catalyzes the conversion of two hydrogen peroxides to oxygen and two waters. Catalase activity can be determined by monitoring the degradation of hydrogen peroxide at 240 nm based on the following reaction: $2H_2O_2 \rightarrow 2H_2O+O_2$. The reaction is conducted in 50 mM phosphate pH 7.0 at 25° C. with 10.3 mM substrate ($H_2O_2$) and approximately 100 units of enzyme per ml. Absorbance is monitored spectrophotometrically within 16-24 seconds, which should correspond to an absorbance reduction from 0.45 to 0.4. One catalase activity unit can be expressed as one micromole of $H_2O_2$ degraded per minute at pH 7.0 and 25° C.

The term "amylase" as used herein means enzymes that hydrolyze alpha-1,4-glucosidic linkages in starch, both in amylose and amylopectin, such as alpha-amylase (EC 3.2.1.1), beta-amylase (EC 3.2.1.2), glucan 1,4-alpha-glucosidase (EC 3.2.1.3), glucan 1,4-alpha-maltotetraohydrolase (EC 3.2.1.60), glucan 1,4-alpha-maltohexaosidase (EC 3.2.1.98), glucan 1,4-alpha-maltotriohydrolase (EC 3.2.1.116) and glucan 1,4-alpha-maltohydrolase (EC 3.2.1.133), and enzymes that hydrolyze alpha-1,6-glucosidic linkages, being the branch-points in amylopectin, such as pullulanase (EC 3.2.1.41) and limit dextinase (EC 3.2.1.142).

A composition as described herein may be composed of a member of each of the classes of enzymes mentioned above, several members of one enzyme class, or any combination of these enzymes classes or helper proteins (i.e. those proteins mentioned herein which do not have enzymatic activity per se, but do nevertheless assist in lignocellulosic degradation).

A composition as described herein may be composed of enzymes from (1) commercial suppliers; (2) cloned genes expressing enzymes; (3) broth (such as that resulting from growth of a microbial strain in media, wherein the strains secrete proteins and enzymes into the media; (4) cell lysates of strains grown as in (3); and/or (5) plant material expressing enzymes. Different enzymes in a composition as described herein may be obtained from different sources.

In the uses and methods described herein, the components of the compositions described above may be provided concomitantly (i.e. as a single composition per se) or separately or sequentially.

The enzymes can be produced either exogenously in microorganisms, yeasts, fungi, bacteria or plants, then isolated and added, for example, to cellulosic or lignocellulosic material. Alternatively, the enzyme may be produced in a fermentation that uses (pretreated) lignocellulosic material (such as corn stover or wheat straw) to provide nutrition to an organism that produces an enzyme(s). In this manner, plants that produce the enzymes may themselves serve as a lignocellulosic material and be added into lignocellulosic material.

In an embodiment the composition is a whole fermentation broth. In an embodiment the composition is in the form of a whole fermentation broth of a fungus, preferably *Rasamsonia*. The whole fermentation broth can be prepared from fermentation of non-recombinant and/or recombinant filamentous fungi. In an embodiment the filamentous fungus is a recombinant filamentous fungus comprising one or more genes which can be homologous or heterologous to the filamentous fungus. In an embodiment, the filamentous fungus is a recombinant filamentous fungus comprising one or more genes which can be homologous or heterologous to the filamentous fungus wherein the one or more genes encode enzymes that can degrade a cellulosic substrate. The whole fermentation broth may comprise any of the polypeptides described above or any combination thereof.

Preferably, the composition is a whole fermentation broth wherein the cells are killed. The whole fermentation broth may contain organic acid(s) (used for killing the cells), killed cells and/or cell debris, and culture medium.

Generally, the filamentous fungi is cultivated in a cell culture medium suitable for production of enzymes capable of hydrolyzing a cellulosic substrate. The cultivation takes place in a suitable nutrient medium comprising carbon and nitrogen sources and inorganic salts, using procedures known in the art. Suitable culture media, temperature ranges and other conditions suitable for growth and cellulase and/or hemicellulase and/or pectinase production are known in the art. The whole fermentation broth can be prepared by growing the filamentous fungi to stationary phase and maintaining the filamentous fungi under limiting carbon conditions for a period of time sufficient to express a variant polypeptide as described herein and/or one or more cellulases and/or hemicellulases and/or pectinases. Once enzymes, such as the variant polypeptide as described herein and/or cellulases and/or hemicellulases and/or pectinases, are secreted by the filamentous fungi into the fermentation medium, the whole fermentation broth can be used. The whole fermentation broth as described herein may comprise filamentous fungi. In some embodiments, the whole fermentation broth comprises the unfractionated contents of the fermentation materials derived at the end of the fermentation. Typically, the whole fermentation broth comprises the spent culture medium and cell debris present after the filamentous fungi is grown to saturation, incubated under carbon-limiting conditions to allow protein synthesis (particularly, expression of cellulases and/or hemicellulases and/or pectinases). In some embodiments, the whole fermentation broth comprises the spent cell culture medium, extracellular enzymes and filamentous fungi. In some embodiments, the filamentous fungi present in whole fermentation broth can be lysed, permeabilized, or killed using methods known in the art to produce a cell-killed whole fermentation broth. In an embodiment, the whole fermentation broth is a cell-killed whole fermentation broth, wherein the whole fermentation broth containing the filamentous fungi cells are lysed or killed. In some embodiments, the cells are killed by lysing the filamentous fungi by chemical and/or pH treatment to generate the cell-killed whole broth of a fermentation of the filamentous fungi. In some embodiments, the cells are killed by lysing the filamentous fungi by chemical and/or pH treatment and adjusting the pH of the cell-killed fermentation mix to a suitable pH. In an embodiment, the whole fermentation broth comprises a first organic acid component comprising at least one 1-5 carbon organic acid and/or a salt thereof and a second organic acid component comprising at least 6 or more carbon organic acid and/or a salt thereof. In an embodiment, the first organic acid component is acetic acid, formic acid, propionic acid, a salt thereof, or any combination thereof and the second organic acid component is benzoic acid, cyclohexanecarboxylic acid, 4-methylvaleric acid, phenylacetic acid, a salt thereof, or any combination thereof.

The term "whole fermentation broth" as used herein refers to a preparation produced by cellular fermentation that undergoes no or minimal recovery and/or purification. For example, whole fermentation broths are produced when microbial cultures are grown to saturation, incubated under carbon-limiting conditions to allow protein synthesis (e.g., expression of enzymes by host cells) and secretion into cell culture medium. Typically, the whole fermentation broth is unfractionated and comprises spent cell culture medium, extracellular enzymes, and microbial, preferably non-viable, cells. If needed, the whole fermentation broth can be fractionated and the one or more of the fractionated contents can be used. For instance, the killed cells and/or cell debris can be removed from a whole fermentation broth to provide a composition that is free of these components.

The whole fermentation broth may further comprise a preservative and/or antimicrobial agent. Such preservatives and/or agents are known in the art.

The whole fermentation broth as described herein is typically a liquid, but may contain insoluble components, such as killed cells, cell debris, culture media components, and/or insoluble enzyme(s). In some embodiments, insoluble components may be removed to provide a clarified whole fermentation broth.

In an embodiment, the whole fermentation broth may be supplemented with one or more enzyme activities that are not expressed endogenously, or expressed at relatively low level by the filamentous fungi, to improve the degradation of the cellulosic substrate, for example, to fermentable sugars such as glucose or xylose. The supplemental enzyme(s) can be added as a supplement to the whole fermentation broth and the enzymes may be a component of a separate whole fermentation broth, or may be purified, or minimally recovered and/or purified.

In an embodiment, the whole fermentation broth comprises a whole fermentation broth of a fermentation of a recombinant filamentous fungi overexpressing one or more enzymes to improve the degradation of the cellulosic substrate. Alternatively, the whole fermentation broth can comprise a mixture of a whole fermentation broth of a fermentation of a non-recombinant filamentous fungus and a recombinant filamentous fungus overexpressing one or more enzymes to improve the degradation of the cellulosic substrate. In an embodiment, the whole fermentation broth comprises a whole fermentation broth of a fermentation of a filamentous fungi overexpressing a variant polypeptide as described herein. In an embodiment, the whole fermentation broth comprises a whole fermentation broth of a fermentation of a filamentous fungi overexpressing another beta-glucosidase. Alternatively, the whole fermentation broth for use in the present methods and compositions can comprise a mixture of a whole fermentation broth of a fermentation of a non-recombinant filamentous fungus expressing a beta-glucosidase and a whole fermentation broth of a fermentation of a recombinant filamentous fungi overexpressing a variant polypeptide as described herein. Alternatively, the whole fermentation broth for use in the present methods and compositions can comprise a mixture of a whole fermentation broth of a fermentation of a recombinant filamentous fungus not expressing any beta-glucosidase and a whole fermentation broth of a fermentation of a recombinant filamentous fungi overexpressing a variant polypeptide as described herein.

Use of the Polypeptides and Compositions

The polypeptides and compositions as described herein may be used in many different applications. For instance, they may be used to produce fermentable sugars. The fermentable sugars can then, as part of a biofuel method, be converted into biogas or ethanol, butanol, isobutanol, 2-butanol or other suitable substances. So, by fermentable sugars is meant sugars which can be consumed by a microorganism or converted by a microorganism in another product. Alternatively, the variant polypeptide as described herein may be used as enzyme, for instance in production of food products, in detergent compositions, in the paper and pulp industry and in antibacterial formulations, in pharmaceutical products such as throat lozenges, toothpastes, and mouthwash. Some of the uses will be illustrated in more detail below.

In the uses and methods described below, the components of the compositions described above may be provided concomitantly (i.e. as a single composition per se) or separately or sequentially.

The application also relates to the use of the variant polypeptide as described herein and compositions in industrial methods.

In principle, a polypeptide or composition as described herein may be used in any method which requires the treatment of a material which comprises polysaccharide. Thus, a polypeptide and/or composition as described herein may be used in the treatment of polysaccharide material. Herein, polysaccharide material is a material which comprises or consists essential of one or, more typically, more than one polysaccharide.

Typically, plants and material derived therefrom comprise significant quantities of non-starch polysaccharide material. Accordingly, a variant polypeptide as described herein may be used in the treatment of a plant or fungal material or a material derived therefrom.

Cellulosic material "Substrate" is used to refer to a substance that comprises carbohydrate material, which may be treated with polypeptides as described herein, so that the carbohydrate material is modified. The substrate may be pretreated or non-pretreated substrate. In addition to the carbohydrate material, the substrate may contain any other component including, but not limited to, non-carbohydrate material and starch. Substrate may be cellulosic material. Substrate may also be lignocellulosic material.

Cellulosic and lignocellulosic materials are abundant in nature and have great value as alternative energy source. Second generation biofuels, also known as advanced biofuels, are fuels that can be manufactured from various types of these materials. The materials can be derived from plants, but can also include animal materials. The composition of the materials varies. The major component is cellulose (in general 35-50%), followed by xylan (a type of hemicellulose, in general 20-35%). Some materials also comprise lignin (in general 10-25%). The materials also may comprise minor components such as proteins, oils and ash (or inorganic compounds).

The materials contain a variety of carbohydrates. The term carbohydrate is most common in biochemistry, where it is a synonym of saccharide. Carbohydrates are divided into four chemical groupings: monosaccharides, disaccharides, oligosaccharides, and polysaccharides. In general, monosaccharides and disaccharides, which are smaller (lower molecular weight) carbohydrates, are commonly referred to as sugars. The enzymatic conversion (such as hydrolysis) of polysaccharides to soluble sugars, for example glucose, gluconic acid, xylose, arabinose, galactose, fructose, mannose, rhamnose, ribose, D-galacturonic acid and other hexoses and pentoses occurs under the action of different enzymes acting in concert.

A composition as described herein may be tailored in view of the particular substrate which is to be used. That is to say, the spectrum of activities in a composition as described herein may vary depending on the substrate in question.

The enzymes used to hydrolyze the substrate can be produced either exogenously in microorganisms such as yeasts, fungi, bacteria or plants, then isolated and added to the substrate. Alternatively, the enzymes can be produced, but not isolated, and a whole fermentation broth can be added to the substrate. Alternatively, the whole fermentation broth may be treated to prevent further microbial growth (for example, by heating or addition of antimicrobial agents), then added to the substrate. The whole fermentation broth may include the organism producing the enzyme(s). Alternatively, the enzyme may be produced in a fermentation that uses substrate to provide nutrition to an organism that produces the enzymes. In this manner, plants that produce the enzymes may serve as the substrate and be added to substrate.

Example of suitable cellulosic and/or lignocellulosic materials include, but are not limited to, virgin biomass and/or non-virgin biomass such as agricultural biomass, herbaceous material, agricultural residues, forestry residues, commercial organics, construction and demolition debris, municipal solid waste, waste paper, yard waste, and pulp and paper mill residues. Common forms of biomass include trees, shrubs and grasses, wheat, wheat straw, sugar cane bagasse, corn, corn husks, corn cobs, corn kernel including fiber from kernels, products and by-products from milling of grains such as corn, wheat and barley (including wet milling and dry milling) often called "bran or fiber" as well as municipal solid waste, waste paper and yard waste. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat middlings, oat hulls, and hard and soft woods (not including woods with deleterious materials). In addition, agricultural biomass includes organic waste materials generated from agricultural methods including farming and forestry activities, specifically including forestry wood waste. Agricultural biomass may be any of the aforestated singularly or in any combination or mixture thereof. Further examples of suitable biomass are orchard primings, chaparral, mill waste, urban wood waste, municipal waste, logging waste, forest thinnings, short-rotation woody crops, industrial waste, wheat straw, oat straw, rice straw, cane straw, barley straw, rye straw, flax straw, soy hulls, rice hulls, rice straw, corn gluten feed, oat hulls, sugar cane, corn stover, corn stalks, corn cobs, corn fiber, corn husks, prairie grass, gamagrass, foxtail; sugar beet pulp, citrus fruit pulp, seed hulls, cellulosic animal wastes, lawn clippings, cotton, seaweed, trees, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat middlings, oat hulls, hard or soft wood, organic waste material generated from an agricultural method, forestry wood waste, or a combination of any two or more thereof.

Apart from virgin biomass or feedstocks already methoded in food and feed or paper and pulping industries, the biomass/feedstock may additionally be pretreated with heat, mechanical and/or chemical modification or any combination of such methods in order to enhance enzymatic degradation.

Pretreatment

Before enzymatic treatment, the feedstock may optionally be pretreated with heat, mechanical and/or chemical modification or any combination of such methods in order to to enhance the accessibility of the substrate to enzymatic hydrolysis and/or hydrolyse the hemicellulose and/or solubilize the hemicellulose and/or cellulose and/or lignin, in any way known in the art. The pretreatment may comprise exposing the lignocellulosic material to (hot) water, steam (steam explosion), an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150 and 220° C. for 1 to 30 minutes.

In an embodiment the lignocellulosic material is pretreated before and/or during the enzymatic hydrolysis. Pretreatment methods are known in the art and include, but are not limited to, heat, mechanical, chemical modification, biological modification and any combination thereof. Pretreatment is typically performed in order to enhance the accessibility of the lignocellulosic material to enzymatic hydrolysis and/or hydrolyse the hemicellulose and/or solubilize the hemicellulose and/or cellulose and/or lignin, in the lignocellulosic material. In an embodiment, the pretreatment comprises treating the lignocellulosic material with steam explosion, hot water treatment or treatment with dilute acid or dilute base. Examples of pretreatment methods include, but are not limited to, steam treatment (e.g. treatment at 100-260° C., at a pressure of 7-45 bar, at neutral pH, for 1-10 minutes), dilute acid treatment (e.g. treatment with 0.1-5% $H_2SO_4$ and/or $SO_2$ and/or $HNO_3$ and/or HCl, in presence or absence of steam, at 120-200° C., at a pressure of 2-15 bar, at acidic pH, for 2-30 minutes), organosolv treatment (e.g. treatment with 1-1.5% $H_2SO_4$ in presence of organic solvent and steam, at 160-200° C., at a pressure of 7-30 bar, at acidic pH, for 30-60 minutes), lime treatment (e.g. treatment with 0.1-2% $NaOH/Ca(OH)_2$ in the presence of water/steam at 60-160° C., at a pressure of 1-10 bar, at alkaline pH, for 60-4800 minutes), ARP treatment (e.g. treatment with 5-15% $NH_3$, at 150-180° C., at a pressure of 9-17 bar, at alkaline pH, for 10-90 minutes), AFEX treatment (e.g. treatment with >15% $NH_3$, at 60-140° C., at a pressure of 8-20 bar, at alkaline pH, for 5-30 minutes).

Hydrolysis

The application also relates to a method for degrading a substrate, the method comprising the step of contacting the substrate with a variant polypeptide as described herein and/or a composition as described herein. The degradation may result in the production of a sugar.

The application also relates to a method for the treatment of a substrate which method comprises the step of contacting the substrate with a variant polypeptide as described herein and/or a composition as described herein. The treatment may result in the production of a sugar.

The application also relates to a method of producing a sugar from a substrate, comprising the steps of (a) enzymatic hydrolysis of the substrate using a variant polypeptide as described herein and/or a composition as described herein to obtain enzymatically hydrolysed substrate, and (b), optionally, recovery of the enzymatically hydrolysed substrate. The enzymatically hydrolysed substrate may comprise a sugar.

The application also relates to a process for the preparation of sugar from lignocellulosic material comprising the steps of (a) hydrolysing the lignocellulosic material with a variant polypeptide as described herein and/or an enzyme composition as described herein to obtain the sugar, and optionally, recovering the sugar.

In an embodiment the substrate comprises a carbohydrate material. In an embodiment the substrate comprises cellulose and/or hemicellulose. In an embodiment the substrate comprises a cellulosic material. In an embodiment the substrate comprises a lignocellulosic material.

In an embodiment the pH of the above methods is between 3.0 and 6.5, preferably between 3.5 and 5.5, more preferably between 4.0 and 5.0.

After the methods have been performed, the resulting material may be subjected to at least one solid/liquid separation. The methods and conditions of solid/liquid separation will depend on the type of substrate used and are well within the scope of the skilled artisan. Examples include, but are not limited to, centrifugation, cyclonic separation, filtration, decantation, sieving and sedimentation. In a preferred embodiment the solid/liquid separation is performed by centrifugation or sedimentation. During solid/liquid separation, means and/or aids for improving the separation may be used.

In an embodiment the substrate is subjected to a pretreatment step before the above methods. In an embodiment the substrate is subjected to a washing step before the above methods. In an embodiment the substrate is subjected to at least one solid/liquid separation before the above methods. So, before subjecting the substrate to any of the above methods, it can be subjected to at least one solid/liquid separation. The solid/liquid separation may be done before and/or after the pretreatment step. Suitable methods and conditions for a solid/liquid separation have been described above.

In an embodiment the application relates to methods wherein the enzymatically hydrolysed substrate is subjected to a solid/liquid separation step followed by a detoxification step and/or a concentration step.

In the methods as described herein substrate may be added to the one or more containers. In an embodiment the variant polypeptide as described herein and/or composition as described herein is already present in the one or more containers before the substrate is added. In another embodiment the variant polypeptide as described herein and/or composition as described herein may be added to the one or more containers. In an embodiment the substrate is already present in the one or more containers before the variant polypeptide as described herein and/or the composition as described herein is added. In an embodiment both the substrate and the variant polypeptide as described herein and/or the composition as described herein are added simultaneously to the one or more containers. The composition present in the one or more containers may be an aqueous composition.

The above methods may comprise a liquefaction step wherein the substrate is liquefied, and a saccharification step wherein the liquefied substrate is saccharified. The liquefaction step is sometimes called presaccharification step. In an embodiment the methods comprise at least a liquefaction step wherein the substrate is liquefied in at least a first container, and a saccharification step wherein the liquefied substrate is saccharified in the at least first container and/or in at least a second container. Saccharification can be done in the same container as the liquefaction (i.e. the at least first container), it can also be done in a separate container (i.e. the at least second container). So, in the methods as described herein liquefaction and saccharification may be combined. Alternatively, the liquefaction and saccharification may be separate steps. Liquefaction and saccharification may be performed at different temperatures, but may also be performed at a single temperature. In an embodiment the temperature of the liquefaction is higher than the temperature of the saccharification. Liquefaction is preferably carried out at a temperature of 60-75° C. and saccharification is preferably carried out at a temperature of 50-65° C.

The methods can be performed in one or more containers, but can also be performed in one or more tubes or any other continuous system. This also holds true when the above methods comprises a liquefaction step and a saccharification step. The liquefaction step can be performed in one or more containers, but can also be performed in one or more tubes or any other continuous system and/or the saccharification step can be performed in one or more containers, but can also be performed in one or more tubes or any other continuous system. Examples of containers to be used in the present application include, but are not limited to, fed-batch stirred containers, batch stirred containers, continuous flow stirred containers with ultrafiltration, and continuous plug-flow column reactors. Stirring can be done by one or more impellers, pumps and/or static mixers.

The polypeptides and/or compositions used in the above methods may be added before and/or during the methods. As indicated above, when the substrate is subjected to a solid/liquid separation before the above methods, the polypeptides and/or compositions used in the above methods may be added before the solid/liquid separation. Alternatively, they may also be added after solid/liquid separation or before and after solid/liquid separation. The polypeptides and/or compositions may also be added during the above methods. In case the above methods comprise a liquefaction step and saccharification step, additional polypeptides and/or compositions may be added during and/or after the liquefaction step. The additional polypeptides and/or compositions may be added before and/or during the saccharification step. Additional polypeptides and/or compositions may also be added after the saccharification step.

In an embodiment the total method time is 10 hours or more, 12 hours or more, 14 hours or more, 16 hours or more, 18 hours or more, 20 hours or more, 30 hours or more, 40 hours or more, 50 hours or more, 60 hours or more, 70 hours or more, 80 hours or more, 90 hours or more, 100 hours or more, 110 hours or more, 120 hours or more, 130 hours or more, 140 hours or more, 150 hours or more, 160 hours or more, 170 hours or more, 180 hours or more, 190 hours or more, 200 hours or more.

In an embodiment, the total method time is 10 to 300 hours, 16 to 275 hours, preferably 20 to 250 hours, more preferably 30 to 200 hours, most preferably 40 to 150 hours.

The viscosity of the substrate in the one or more containers used for the above methods is kept between 10 and 4000 cP, between 10 and 2000 cP, preferably between 10 and 1000 cP.

Incubation of substrate under the above conditions results in release or liberation of a substantial amount of sugars from the substrate. By substantial amount is meant at least 20%, 30%, 40%, 50%, 60%, 70%, 80%, 90%, 95% or more of the available sugars.

In case the methods comprises a liquefaction step and a saccharification step, the viscosity of the substrate in the liquefaction step is kept between 10 and 4000 cP, between 10 and 2000 cP, preferably between 10 and 1000 cP and/or the viscosity of the substrate in the saccharification step is kept between 10 and 1000 cP, between 10 and 900 cP, preferably between 10 and 800 cP.

The viscosity can be determined with a Brookfield DV III Rheometer at the temperature used for the above methods.

Significantly, the above methods may be carried out using high levels of dry matter (of the substrate). In an embodiment the dry matter content at the end of the above methods is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher or 39 wt % or higher. In an embodiment the dry matter content at the end of the above methods is between 5 wt %-40 wt %, 6 wt %-40 wt %, 7 wt %-40 wt %, 8 wt %-40 wt %, 9 wt %-40 wt %, 10 wt %-40 wt %, 11 wt %-40 wt %, 12 wt %-40 wt %, 13 wt %-40 wt %, 14 wt %-40 wt %, 15 wt %-40 wt %, 16 wt %-40 wt %, 17 wt %-40 wt %, 18 wt %-40 wt %, 19 wt %-40 wt %, 20 wt %-40 wt %, 21 wt %-40 wt %, 22 wt %-40 wt %, 23 wt %-40 wt %, 24 wt %-40 wt %, 25 wt %-40 wt %, 26 wt %-40 wt %, 27 wt %-40 wt %, 28 wt %-40 wt %, 29 wt %-40 wt %, 30 wt %-40 wt %, 31 wt %-40 wt %, 32 wt %-40 wt %, 33 wt %-40 wt %, 34 wt %-40 wt %, 35 wt %-40 wt %, 36 wt %-40 wt %, 37 wt %-40 wt %, 38 wt %-40 wt %, 39 wt %-40 wt %.

In an embodiment the dry matter content at the end of the liquefaction step of the above methods is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher or 39 wt % or higher. In an embodiment the dry matter content at the end of the liquefaction step of the the above methods is between 5 wt %-40 wt %, 6 wt %-40 wt %, 7 wt %-40 wt %, 8 wt %-40 wt %, 9 wt %-40 wt %, 10 wt %-40 wt %, 11 wt %-40 wt %, 12 wt %-40 wt %, 13 wt %-40 wt %, 14 wt %-40 wt %, 15 wt %-40 wt %, 16 wt %-40 wt %, 17 wt %-40 wt %, 18 wt %-40 wt %, 19 wt %-40 wt %, 20 wt %-40 wt %, 21 wt %-40 wt %, 22 wt %-40 wt %, 23 wt %-40 wt %, 24 wt %-40 wt %, 25 wt %-40 wt %, 26 wt %-40 wt %, 27 wt %-40 wt %, 28 wt %-40 wt %, 29 wt %-40 wt %, 30 wt %-40 wt %, 31 wt %-40 wt %, 32 wt %-40 wt %, 33 wt %-40 wt %, 34 wt %-40 wt %, 35 wt %-40 wt %, 36 wt %-40 wt %, 37 wt %-40 wt %, 38 wt %-40 wt %, 39 wt %-40 wt %.

In an embodiment the dry matter content at the end of the saccharification step of the above methods is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher or 39 wt % or higher. In an embodiment the dry matter content at the end of the saccharification step of the above methods is between 5 wt %-40 wt %, 6 wt %-40 wt %, 7 wt %-40 wt %, 8 wt %-40 wt %, 9 wt %-40 wt %, 10 wt %-40 wt %, 11 wt %-40 wt %, 12 wt %-40 wt %, 13 wt %-40 wt %, 14 wt %-40 wt %, 15 wt %-40 wt %, 16 wt %-40 wt %, 17 wt %-40 wt %, 18 wt %-40 wt %, 19 wt %-40 wt %, 20 wt %-40 wt %, 21 wt %-40 wt %, 22 wt %-40 wt %, 23 wt %-40 wt %, 24 wt %-40 wt %, 25 wt %-40 wt %, 26 wt %-40 wt %, 27 wt %-40 wt %, 28 wt %-40 wt %, 29 wt %-40 wt %, 30 wt %-40 wt %, 31 wt %-40 wt %, 32 wt %-40 wt %, 33 wt %-40 wt %, 34 wt %-40 wt %, 35 wt %-40 wt %, 36 wt %-40 wt %, 37 wt %-40 wt %, 38 wt %-40 wt %, 39 wt %-40 wt %.

In an embodiment oxygen is added during the above methods. In an embodiment oxygen is added during at least a part of the above methods. Oxygen can be added continuously or discontinuously during the above methods. In an embodiment oxygen is added one or more times during the above methods. In an embodiment oxygen may be added before the above methods, during the addition of cellulosic material to a container used for the above methods, during the addition of enzyme to a container used for the above methods, during a part of the above methods, during the whole methods or any combination thereof. Oxygen is added to the one or more containers used in the above methods.

Oxygen can be added in several forms. For example, oxygen can be added as oxygen gas, oxygen-enriched gas, such as oxygen-enriched air, or air. Oxygen may also be added by means of in situ oxygen generation. For example, oxygen may be generated by electrolysis, oxygen may be produced enzymatically, e.g. by the addition of peroxide, or oxygen may be produced chemically, e.g. by an oxygen generating system such as $KHSO_5$. For example, oxygen is produced from peroxide by catalase. The peroxide can be added in the form of dissolved peroxide or generated by an enzymatic or chemical reaction. In case catalase is used as enzyme to produce oxygen, catalase present in the enzyme composition for the hydrolysis can be used or catalase can be added for this purpose.

Examples how to add oxygen include, but are not limited to, addition of oxygen by means of sparging, electrolysis, chemical addition of oxygen, filling the one or more containers used in the the above methods from the top (plunging the hydrolysate into the tank and consequently introducing oxygen into the hydrolysate) and addition of oxygen to the headspace of said one or more containers. When oxygen is added to the headspace of the container(s), sufficient oxygen necessary for the hydrolysis reaction may be supplied. In general, the amount of oxygen added to the container(s) can be controlled and/or varied. Restriction of the oxygen supplied is possible by adding only oxygen during part of the hydrolysis time in said container(s). Another option is adding oxygen at a low concentration, for example by using a mixture of air and recycled air (air leaving the container) or by "diluting" air with an inert gas. Increasing the amount of oxygen added can be achieved by addition of oxygen during longer periods of the hydrolysis time, by adding the oxygen at a higher concentration or by adding more air. Another way to control the oxygen concentration is to add an oxygen consumer and/or an oxygen generator. Oxygen can be introduced, for example blown, into the liquid hydrolysis container contents of substrate. It can also be blown into the headspace of the container.

In an embodiment oxygen is added to the one or more containers used in the above methods before and/or during and/or after the addition of the substrate to said one or more containers. The oxygen may be introduced together with the substrate that enters the hydrolysis container(s). The oxygen may be introduced into the material stream that will enter the container(s) or with part of the container(s) contents that passes an external loop of the container(s).

In an embodiment the container(s) used in the the above methods and/or the polypeptide production methods have a volume of at least 1 $m^3$. Preferably, the containers have a volume of at least 1 $m^3$, at least 2 $m^3$, at least 3 $m^3$, at least 4 $m^3$, at least 5 $m^3$, at least 6 $m^3$, at least 7 $m^3$, at least 8 $m^3$, at least 9 $m^3$, at least 10 $m^3$, at least 15 $m^3$, at least 20 $m^3$, at least 25 $m^3$, at least 30 $m^3$, at least 35 $m^3$, at least 40 $m^3$, at least 45 $m^3$, at least 50 $m^3$, at least 60 $m^3$, at least 70 $m^3$, at least 75 $m^3$, at least 80 $m^3$, at least 90 $m^3$, at least 100 $m^3$, at least 200 $m^3$, at least 300 $m^3$, at least 400 $m^3$, at least 500 $m^3$, at least 600 $m^3$, at least 700 $m^3$, at least 800 $m^3$, at least 900 $m^3$, at least 1000 $m^3$, at least 1500 $m^3$, at least 2000 $m^3$, at least 2500 $m^3$. In general, the container(s) will be smaller than 3000 $m^3$ or 5000 $m^3$. In case several containers are used in the above methods, they may have the same volume, but also may have a different volume. In case the above methods comprises a separate liquefaction step and saccharification step the container(s) used for the liquefaction step and the container(s) used for the saccharification step may have the same volume, but also may have a different volume.

Hydrolysis and fermentation (see below), separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated biomethoding (CBP).

Fermentation

The present application also relates to a method of producing a fermentation product, the method comprising the steps of (a) treating a substrate by contacting the substrate with a variant polypeptide as described herein and/or a composition as described herein, and (b) fermenting the resulting material to produce the fermentation product. The resulting material may comprise a sugar.

The present application also relates to a method of producing a fermentation product, the method comprising the steps of (a) enzymatically hydrolysing a substrate with a variant polypeptide as described herein and/or a composition as described herein, (b) fermenting the enzymatically hydrolysed cellulosic substrate to produce a fermentation product, and (c) optionally, recovering the fermentation product.

The present application also relates to a process for producing a fermentation product from a lignocellulosic material, which process comprises the steps of (a) hydrolysing the lignocellulosic material with a variant polypeptide as described herein and/or a composition as described herein to obtain a sugar, (b) fermenting the obtained sugar by contacting the obtained sugar with a fermenting microorganism to produce the fermentation product, and (c) optionally, recovering the fermentation product.

For instance, in the method as described herein a variant polypeptide as described herein and/or a composition as described herein acts on a substrate, so as to convert this substrate to sugars and oligosaccharides for the production of fermentation products.

The application thus also provides a method of producing a fermentation product, which method comprises (a) degrading a substrate using a method as described herein, and (b) fermentation of the resulting material, thereby to prepare a fermentation product. The above methods of producing a fermentation product may optionally comprise recovery of the fermentation product.

In an embodiment the fermentation (i.e. step b) is performed in one or more containers. In an embodiment the fermentation is done by an alcohol producing microorganism to produce alcohol. In an embodiment the fermentation is done by an organic acid producing microorganism to produce an organic acid. The fermentation by an alcohol producing microorganism to produce alcohol can be done in the same container(s) wherein the step (a) is performed. Alternatively, the fermentation by an alcohol producing microorganism to produce alcohol and the fermentation by an organic acid producing microorganism to produce an organic acid can be performed in one or more separate containers, but may also be done in one or more of the same containers.

In an embodiment the fermentation is done by a yeast. In an embodiment the alcohol producing microorganism and/or the organic acid producing microorganism is a yeast. In an embodiment the alcohol producing microorganism is able to ferment at least a C5 sugar and at least a C6 sugar. In an embodiment the organic acid producing microorganism is able to ferment at least a C6 sugar. In an embodiment the alcohol producing microorganism and the organic acid producing microorganism are different microorganisms. In another embodiment the alcohol producing microorganism and the organic acid producing microorganism are the same microorganism, i.e. the alcohol producing microorganism is also able to produce organic acid such as succinic acid.

In a further aspect, the application thus includes fermentation methods in which a microorganism is used for the fermentation of a carbon source comprising sugar(s), e.g. glucose, L-arabinose and/or xylose. The carbon source may include any carbohydrate oligomer or polymer comprising L-arabinose, xylose or glucose units, such as e.g. lignocellulose, xylans, cellulose, starch, arabinan and the like. For release of xylose or glucose units from such carbohydrates, appropriate carbohydrases (such as xylanases, glucanases, amylases and the like) may be added to the fermentation medium or may be produced by the modified host cell. In the latter case, the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose. In a preferred method the modified host cell ferments both the L-arabinose (optionally xylose) and glucose, preferably simultaneously in which case preferably a modified host cell is used which is insensitive to glucose repression to prevent diauxic growth. In addition to a source of L-arabinose, optionally xylose (and glucose) as carbon source, the fermentation medium will further comprise the appropriate ingredient required for growth of the modified host cell. Compositions of fermentation media for growth of microorganisms such as yeasts or filamentous fungi are well known in the art.

The fermentation time may be shorter than in conventional fermentation at the same conditions, wherein part of the enzymatic hydrolysis still has to take part during fermentation. In one embodiment, the fermentation time is 100 hours or less, 90 hours or less, 80 hours or less, 70 hours or less, or 60 hours or less, for a sugar composition of 50 g/l glucose and corresponding other sugars from the cellulosic material (e.g. 50 g/l xylose, 35 g/l L-arabinose and 10 g/l galactose). For more dilute sugar compositions, the fermentation time may correspondingly be reduced. In an embodiment the fermentation time of the ethanol production step is between 10 and 50 hours for ethanol made out of C6 sugars and between 20 and 100 hours for ethanol made out of C5 sugars. In an embodiment the fermentation time of the succinic acid production step is between 20 and 70 hours.

The fermentation method may be an aerobic or an anaerobic fermentation method. An anaerobic fermentation method is herein defined as a fermentation method run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$. Thus, in a preferred anaerobic fermentation method pyruvate is used as an electron (and hydrogen acceptor) and is reduced to fermentation products such as ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotics and a cephalosporin. In a preferred embodiment, the fermentation method is anaerobic. An anaerobic method is advantageous, since it is cheaper than aerobic methods: less special equipment is needed. Furthermore, anaerobic methods are expected to give a higher product yield than aerobic methods. Under aerobic conditions, usually the biomass yield is higher than under anaerobic conditions. As a consequence, usually under aerobic conditions, the expected product yield is lower than under anaerobic conditions.

In another embodiment, the fermentation method is under oxygen-limited conditions. More preferably, the fermentation method is aerobic and under oxygen-limited conditions. An oxygen-limited fermentation method is a method in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used. Preferably, in a method under oxygen-limited conditions, the rate of oxygen consumption is at least 5.5, more preferably at least 6 and even more preferably at least 7 mmol/L/h.

In an embodiment the alcohol fermentation method is anaerobic, while the organic acid fermentation method is aerobic, but done under oxygen-limited conditions.

The fermentation method is preferably run at a temperature that is optimal for the microorganism used. Thus, for most yeasts or fungal cells, the fermentation method is performed at a temperature which is less than 42° C., preferably 38° C. or lower. For yeast or filamentous fungal host cells, the fermentation method is preferably performed at a temperature which is lower than 35, 33, 30 or 28° C. and at a temperature which is higher than 20, 22, or 25° C. In an embodiment the alcohol fermentation step and the organic acid fermentation step are performed between 25° C. and 35° C.

In an embodiment of the application, the fermentations are conducted with a fermenting microorganism. In an embodiment of the application, the alcohol (e.g. ethanol) fermentations of C5 sugars are conducted with a C5 fermenting microorganism. In an embodiment of the application, the alcohol (e.g. ethanol) fermentations of C6 sugars are conducted with a C5 fermenting microorganism or a commercial C6 fermenting microorganism. Commercially available yeast suitable for ethanol production include, but are not limited to, BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In an embodiment propagation of the alcohol producing microorganism and/or the organic acid producing microorganism is performed in one or more propagation containers. After propagation, the alcohol producing microorganism and/or the organic acid producing microorganism may be added to one or more fermentation containers. Alternatively, the propagation of the alcohol producing microorganism and/or the organic acid producing microorganism is combined with the fermentation by the alcohol producing microorganism and/or the organic acid producing microorganism to produce alcohol and/or organic acid, respectively.

In an embodiment the alcohol producing microorganism is a microorganism that is able to ferment at least one C5 sugar. Preferably, it also is able to ferment at least one C6 sugar. In an embodiment the application relates to a method for the preparation of ethanol from cellulosic material, comprising the steps of (a) performing a method for the preparation of a sugar product from cellulosic material as described above, (b) fermentation of the enzymatically hydrolysed cellulosic material to produce ethanol; and (c) optionally, recovery of the ethanol. The fermentation can be done with a microorganism that is able to ferment at least one C5 sugar.

In an embodiment the organic acid producing microorganism is a microorganism that is able to ferment at least one C6 sugar. In an embodiment the application relates to a method for the preparation of succinic acid from cellulosic material, comprising the steps of (a) performing a method for the preparation of a sugar product from cellulosic material as described above, (b) fermentation of the enzymatically hydrolysed cellulosic material to produce succinic acid; and (c) optionally, recovery of the succinic acid. The fermentation can be done with a microorganism that is able to ferment at least one C6 sugar.

The alcohol producing microorganisms may be a prokaryotic or eukaryotic organism. The microorganism used in the method may be a genetically engineered microorganism. Examples of suitable alcohol producing organisms are yeasts, for instance Saccharomyces, e.g. Saccharomyces cerevisiae, Saccharomyces pastorianus or Saccharomyces uvarum, Hansenula, Issatchenkia, e.g. Issatchenkia orientalis, Pichia, e.g. Pichia stipites or Pichia pastoris, Kluyveromyces, e.g. Kluyveromyces fagilis, Candida, e.g. Candida pseudotropicalis or Candida acidothermophilum, Pachysolen, e.g. Pachysolen tannophilus or bacteria, for instance Lactobacillus, e.g. Lactobacillus lactis, Geobacifius, Zymomonas, e.g. Zymomonas mobilis, Clostridium, e.g. Clostridium phytofermentans, Escherichia, e.g. E. coli, Klebsiella, e.g. Klebsiella oxytoca. In an embodiment the microorganism that is able to ferment at least one C5 sugar is a yeast. In an embodiment, the yeast is belongs to the genus Saccharomyces, preferably of the species Saccharomyces cerevisiae. The yeast, e.g. Saccharomyces cerevisiae, used in the methods as described herein is capable of converting hexose (C6) sugars and pentose (C5) sugars. The yeast, e.g. Saccharomyces cerevisiae, used in the methods as described herein can anaerobically ferment at least one C6 sugar and at least one C5 sugar. For example, the yeast is capable of using L-arabinose and xylose in addition to glucose anaerobically. In an embodiment, the yeast is capable of converting L-arabinose into L-ribulose and/or xylulose 5-phosphate and/or into a desired fermentation product, for example into ethanol. Organisms, for example Saccharomyces cerevisiae strains, able to produce ethanol from L-arabinose may be produced by modifying a host yeast introducing the araA (L-arabinose isomerase), araB (L-ribuloglyoxalate) and araD (L-ribulose-5-P4-epimerase) genes from a suitable source. Such genes may be introduced into a host cell in order that it is capable of using arabinose. Such an approach is given is described in WO 2003/095627. araA, araB and araD genes from Lactobacillus plantarum may be used and are disclosed in WO2008/041840. The araA gene from Bacillus subtilis and the araB and araD genes from Escherichia coli may be used and are disclosed in EP1499708. In another embodiment, araA, araB and araD genes may derived from of at least one of the genus Clavibacter, Arthrobacter and/or Gramella, in particular one of Clavibacter michiganensis, Arthrobacter aurescens, and/or Gramella forsetii, as disclosed in WO 2009011591. In an embodiment, the yeast may also comprise one or more copies of xylose isomerase gene and/or one or more copies of xylose reductase and/or xylitol dehydrogenase.

The yeast may comprise one or more genetic modifications to allow the yeast to ferment xylose. Examples of genetic modifications are introduction of one or more xylA-gene, XYL1 gene and XYL2 gene and/or XKS1-gene; deletion of the aldose reductase (GRE3) gene; overexpression of PPP-genes TAD, TKL1, RPE1 and RKI1 to allow the increase of the flux through the pentose phosphate pathway in the cell. Examples of genetically engineered yeast are described in EP1468093 and/or WO2006/009434.

An example of a suitable commercial yeast is RN1016 that is a xylose and glucose fermenting Saccharomyces cerevisiae strain from DSM, the Netherlands.

In an embodiment, the fermentation method for the production of ethanol is anaerobic. Anaerobic has already been defined earlier herein. In another preferred embodiment, the fermentation method for the production of ethanol is aerobic. In another preferred embodiment, the fermentation method for the production of ethanol is under oxygen-limited conditions, more preferably aerobic and under oxygen-limited conditions. Oxygen-limited conditions have already been defined earlier herein.

The volumetric ethanol productivity is preferably at least 0.5, 1.0, 1.5, 2.0, 2.5, 3.0, 5.0 or 10.0 g ethanol per litre per hour. The ethanol yield on L-arabinose and optionally xylose and/or glucose in the method preferably is at least 20, 25, 30, 35, 40, 45, 50, 60, 70, 80, 90, 95 or 98%. The ethanol yield is herein defined as a percentage of the theoretical maximum yield, which, for glucose and L-arabinose and optionally xylose is 0.51 g ethanol per g glucose or xylose.

In one aspect, the fermentation method leading to the production of ethanol, has several advantages by comparison to known ethanol fermentations methods: anaerobic methods are possible; oxygen limited conditions are possible; higher ethanol yields and ethanol production rates can be obtained; the strain used may be able to use L-arabinose and optionally xylose.

Alternatively to the fermentation methods described above, at least two distinct cells may be used, this means this method is a co-fermentation method. All preferred embodiments of the fermentation methods as described above are also preferred embodiments of this co-fermentation method: identity of the fermentation product, identity of source of L-arabinose and source of xylose, conditions of fermentation (aerobic or anaerobic conditions, oxygen-limited conditions, temperature at which the method is being carried out, productivity of ethanol, yield of ethanol).

The organic acid producing microorganisms may be a prokaryotic or eukaryotic organism. The microorganism used in the method may be a genetically engineered microorganism. Examples of suitable organic acid producing organisms are yeasts, for instance Saccharomyces, e.g. Saccharomyces cerevisiae; fungi for instance Aspergillus strains, such as Aspergillus niger and Aspergillus fumigatus, Byssochlamys nivea, Lentinus degener, Paecilomyces varioti and Penicillium viniferum; and bacteria, for instance Anaerobiospirillium succiniciproducens, Actinobacillus succinogenes, Mannhei succiniciproducers MBEL 55E, Escherichia coli, Propionibacterium species, Pectinatus sp., Bacteroides sp., such as Bacteroides amylophilus, Ruminococcus flavefaciens, Prevotella ruminicola, Succcinimonas amylolytica, Succinivibrio dextrinisolvens, Wolinella succinogenes, and Cytophaga succinicans. In an embodiment the organic acid producing microorganism that is able to ferment at least one C6 sugar is a yeast. In an embodiment, the yeast is belongs to the genus Saccharomyces, preferably of the species Saccharomyces cerevisiae. The yeast, e.g. Saccharomyces cerevisiae, used in the production methods of organic acid as described herein is capable of converting hexose (C6) sugars. The yeast, e.g. Saccharomyces cerevisiae, used in the methods as described herein can anaerobically ferment at least one C6 sugar.

The overall reaction time (or the reaction time of hydrolysis step and fermentation step together) may be reduced. In one embodiment, the overall reaction time is 300 hours or less, 200 hours or less, 150 hours or less, 140 hours or less, 130 or less, 120 hours or less, 110 hours or less, 100 hours of less, 90 hours or less, 80 hours or less, 75 hours or less, or about 72 hours at 90% glucose yield. Correspondingly, lower overall reaction times may be reached at lower glucose yield.

Fermentation products that may be produced by the methods as described herein can be any substance derived from fermentation. They include, but are not limited to, alcohol (such as arabinitol, butanol, ethanol, glycerol, methanol, 1,3-propanediol, sorbitol, and xylitol); organic acid (such as acetic acid, acetonic acid, adipic acid, ascorbic acid, acrylic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, maleic acid, malic acid, malonic acid, oxalic acid, oxaloacetic acid, propionic acid, succinic acid, and xylonic acid); ketones (such as acetone); amino acids (such as aspartic acid, glutamic acid, glycine, lysine, serine, tryptophan, and threonine); alkanes (such as pentane, hexane, heptane, octane, nonane, decane, undecane, and dodecane), cycloalkanes (such as cyclopentane, cyclohexane, cycloheptane, and cyclooctane), alkenes (such as pentene, hexene, heptene, and octene); and gases (such as methane, hydrogen ($H_2$), carbon dioxide ($CO_2$), and carbon monoxide (CO)). The fermentation product can also be a protein, a vitamin, a pharmaceutical, an animal feed supplement, a specialty chemical, a chemical feedstock, a plastic, a solvent, ethylene, an enzyme, such as a protease, a cellulase, an amylase, a glucanase, a lactase, a lipase, a lyase, an oxidoreductase, a transferase or a xylanase. In a preferred embodiment an organic acid and/or an alcohol is prepared in the fermentation methods as described herein. In a preferred embodiment succinic acid and/or ethanol is prepared in the fermentation methods as described herein.

Use of the Polypeptide and Composition as Described Herein

The variant polypeptides and compositions as described herein may be used in many different applications. For instance, they may be used to produce fermentable sugars. The fermentable sugars can then, as part of a biofuel method, be converted into biogas or ethanol, butanol, isobutanol, 2-butanol or other fermentation products. A non-extendible list is given above.

By "fermentable sugars" is meant sugars which can be consumed by a microorganism or converted by a microorganism into a fermentation product.

Alternatively, a variant polypeptide as described herein and/or a composition as described herein may be used in the production of a food product, a detergent composition, in the paper and pulp industry, in antibacterial formulations, in pharmaceutical products to name just a few. Some of the uses will be illustrated in more detail below.

In the uses and methods described below, the components of the compositions described above may be provided concomitantly (i.e. as a single composition per se) or separately or sequentially.

In principle, a variant polypeptide as described herein and/or composition as described herein may be used in any method which requires the treatment of a material which comprises polysaccharide. Thus, a variant polypeptide and/or composition as described herein may be used in the treatment of polysaccharide material. Herein, polysaccharide material is a material which comprises or consists essential of one or, more typically, more than one polysaccharide.

The application also provides use of a polypeptide and/or composition a described herein in a method for the preparation of biogas. Biogas typically refers to a gas produced by the biological breakdown of organic matter, for example cellulosic material, in the absence of oxygen. Biogas originates from biogenic material and is a type of biofuel. One type of biogas is produced by anaerobic digestion or fermentation of biodegradable materials such as biomass, manure or sewage, municipal waste, and energy crops. This type of biogas is comprised primarily of methane and carbon dioxide. The gas methane can be combusted or oxidized with oxygen. Air contains 21% oxygen. This energy release allows biogas to be used as a fuel. Biogas can be used as a low-cost fuel in any country for any heating purpose, such as cooking. It can also be utilized in modern waste management facilities where it can be used to run any type of heat engine, to generate either mechanical or electrical power. The first step in microbial biogas production consists in the enzymatic degradation of polymers and complex substrates. Accordingly, the application provides a method for preparation of a biogas in which a cellulosic substrate is contacted with a polypeptide and/or composition as described herein, thereby to yield fermentable material which may be converted into a biogas by an organism, such as a microorganism. In such a method, a polypeptide and/or composition as described herein may be provided by way of an organism, for example a microorganism which expresses a polypeptide and/or composition as described herein.

The polypeptides and/or compositions as described herein may be used in a method of treating material to degrade or modify the cellulose and/or hemicellulose and/or pectic substance constituents of the material. Such methods may be useful in the preparation of a food product. Accordingly, the application provides a method for preparing a food product which method comprises incorporating a variant polypeptide and/or composition as described herein during preparation of the food product. The application also provides a method of methoding a cellulosic material, which method comprises contacting the cellulosic material with a variant polypeptide and/or composition as described herein to degrade or modify the cellulose in the material. The present application also provides a method for reducing the viscosity, clarity and/or filterability of a cellulosic material, which method comprises contacting the material with a variant polypeptide and/or composition as described herein in an amount effective in degrading cellulose and/or hemicellulose and/or pectic substances in the material. Cellulosic materials in this respect include, but are not limited to, plant pulp, parts of plants and plant extracts. In the context of this application an extract from a plant material is any substance which can be derived from plant material by extraction (mechanical and/or chemical), methoding or by other separation techniques. The extract may be juice, nectar, base or concentrate made thereof. The plant material may comprise or be derived from vegetables (e.g. carrots, celery, onions, legumes or leguminous plants (soy, soybean, peas)) or fruit (e.g., pome or seed fruit (apples, pears, quince etc.), grapes, tomatoes, citrus (orange, lemon, lime, mandarin), melons, prunes, cherries, black currants, redcurrants, raspberries, strawberries, cranberries, pineapple and other tropical fruits), trees and parts thereof (e.g. pollen, from pine trees), or cereal (oats, barley, wheat, maize, rice). The material (to be hydrolysed) may also be agricultural residues, such as sugar beet pulp, corn cobs, wheat straw, (ground) nutshells, or recyclable materials, e.g. (waste) paper. The variant polypeptides as described herein can thus be used to treat plant material including plant pulp and plant extracts. They may also be used to treat liquid or solid foodstuffs or edible foodstuff ingredients, or be used in the extraction of coffee, plant oils, starch or as a thickener in foods. Typically, the variant polypeptides as described herein are used as a composition as described above. The composition will generally be added to plant pulp obtainable by, for example mechanical methoding such as crushing or milling plant material. Incubation of the composition with the plant will typically be carried out for at time of from 10 minutes to 5 hours. The methoding temperature is preferably from about 10° C. to about 55° C. and one can use from about 10 g to about 300 g of enzyme per ton of material to be treated. The variant polypeptides or compositions as described herein may be added sequentially or at the same time to the plant pulp. Depending on the composition of the enzyme preparation the plant material may first be macerated (e.g. to a pure) or liquefied. Using the variant polypeptides as described herein, methoding parameters such as the yield of the extraction, viscosity of the extract and/or quality of the extract can be improved. Alternatively, or in addition to the above, a variant polypeptide and/or composition as described herein may be added to the raw juice obtained from pressing or liquefying the plant pulp. Treatment of the raw juice will be carried out in a similar manner to the plant pulp in respect of dosage, temperature and holding time. Again, other enzymes such as those discussed previously may be included. Typical incubation conditions are as described above. Once the raw juice has been incubated with the variant polypeptides or compositions as described herein, the juice is then centrifuged or (ultra) filtered to produce the final product. After treatment with the variant polypeptide and/or composition as described herein, the (end) product can be heat treated, e.g. at about 100° C. for a time of from about 1 minute to about 1 hour, under conditions to partially or fully inactivate the variant polypeptide and/or composition as described herein. A variant polypeptide and/or composition as described herein may also be used during the preparation of fruit or vegetable purees. The variant polypeptide and/or composition as described herein may also be used in brewing, wine making, distilling or baking. It may therefore be used in the preparation of alcoholic beverages such as wine and beer. For example, it may improve the filterability or clarity, for example of beers, wort (e.g. containing barley and/or sorghum malt) or wine. Furthermore, a variant polypeptide and/or composition as described herein may be used for treatment of brewers spent grain, i.e. residuals from beer wort production containing barley or malted barley or other cereals, so as to improve the utilization of the residuals for e.g. animal feed. A variant polypeptide and/or composition as described herein may assist in the removal of dissolved organic substances from broth or culture media, for example where distillery waste from organic origin is bioconverted into microbial biomass. The variant polypeptide and/or composition as described herein may improve filterability and/or reduce viscosity in glucose syrups, such as from cereals produced by liquefaction (e.g. with α-amylase). In baking, the variant polypeptide and/or composition as described herein may improve the dough structure, modify its stickiness or suppleness, improve the loaf volume and/or crumb structure or impart better textural characteristics such as break, shred or crumb quality. The present application thus relates to methods for preparing a dough or a cereal-based food product comprising incorporating into the dough a variant polypeptide and/or composition as described herein. This may improve one or more properties of the dough or the cereal-based food product obtained from the dough relative to a dough or a cereal-based food product in which the variant polypeptide and/or composition is not incorporated. The preparation of the cereal-based food product further can comprise steps known in the art such as boiling, drying, frying, steaming or baking of the obtained dough. Products that are made from a dough that is boiled are for example boiled noodles, dumplings, products that are made from fried dough are for example doughnuts, beignets, fried noodles, products that are made for steamed dough are for example steamed buns and steamed noodles, examples of products made from dried dough are pasta and dried noodles and examples of products made from baked dough are bread, cookies and cake. The term "improved property" is defined herein as any property of a dough and/or a product obtained from the dough, particularly a cereal-based food product, which is improved by the action of the variant polypeptide and/or composition as described herein relative to a dough or product in which the variant polypeptide and/or composition as described herein is not incorporated. The improved property may include, but is not limited to, increased strength of the dough, increased elasticity of the dough, increased stability of the dough, improved machinability of the dough, improved proofing resistance of the dough, reduced stickiness of the dough, improved extensibility of the dough, increased volume of the cereal-based food product, reduced blistering of the cereal-based food product, improved crumb structure of the baked product, improved softness of the cereal-based food product, improved flavour of the cereal-based food product, improved anti-staling of the cereal-based food product. Improved properties related to pasta and noodle type of cereal-based products are for example improved firmness, reduced stickiness, improved cohesiveness and reduced cooking loss. Non-starch polysaccharides (NSP) can increase the viscosity of the digesta which can, in turn, decrease nutrient availability and animal performance. Adding specific nutrients to feed improves animal digestion and thereby reduces feed costs. Non-starch polysaccharides (NSPs) are also present in virtually all feed ingredients of plant origin. NSPs are poorly utilized and can, when solubilized, exert adverse effects on digestion. Exogenous enzymes can contribute to a better utilization of these NSPs and as a consequence reduce any anti-nutritional effects. A variant polypeptide and/or composition as described herein can be used for this purpose in cereal-based diets for poultry and, to a lesser extent, for pigs and other species.

A variant polypeptide and/or composition as described herein may be used in the detergent industry, for example for removal from laundry of carbohydrate-based stains. A detergent composition may comprise a variant polypeptide and/or composition as described herein and, in addition, one or more of a cellulase, a hemicellulase, a pectinase, a protease, a lipase, a cutinase, an amylase or a carbohydrase. A detergent composition comprising a variant polypeptide and/or composition as described herein may be in any convenient form, for example a paste, a gel, a powder or a liquid. A liquid detergent may be aqueous, typically containing up to about 70% water and from about 0 to about 30% organic solvent or non-aqueous material. Such a detergent composition may, for example, be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dish washing operations. In general, the properties of the variant polypeptide and/or composition as described herein should be compatible with the selected detergent (for example, pH-optimum, compatibility with other enzymatic and/or non-enzymatic ingredients, etc.) and the variant polypeptide and/or composition as described herein should be present in an effective amount. A detergent composition may comprise a surfactant, for example an anionic or non-ionic surfactant, a detergent builder or complexing agent, one or more polymers, a bleaching system (for example an $H_2O_2$ source) or an enzyme stabilizer. A detergent composition may also comprise any other conventional detergent ingredient such as, for example, a conditioner including a clay, a foam booster, a sud suppressor, an anti-corrosion agent, a soil-suspending agent, an an-soil redeposition agent, a dye, a bactericide, an optical brightener, a hydrotropes, a tarnish inhibitor or a perfume.

A variant polypeptide and/or composition as described herein may be used in the paper and pulp industry, inter alia in the bleaching method to enhance the brightness of bleached pulps whereby the amount of chlorine used in the bleaching stages may be reduced, and to increase the freeness of pulps in the recycled paper method. Furthermore, a variant polypeptide and/or composition as described herein may be used for treatment of lignocellulosic pulp so as to improve the bleachability thereof. Thereby the amount of chlorine need to obtain a satisfactory bleaching of the pulp may be reduced.

A variant polypeptide and/or composition as described herein may be used in a method of reducing the rate at which cellulose-containing fabrics become harsh or of reducing the harshness of cellulose-containing fabrics, the method comprising treating cellulose-containing fabrics with a variant polypeptide and/or composition as described above. The present application further relates to a method providing colour clarification of coloured cellulose-containing fabrics, the method comprising treating coloured cellulose-containing fabrics with a variant polypeptide and/or composition as described above, and a method of providing a localized variation in colour of coloured cellulose-containing fabrics, the method comprising treating coloured cellulose-containing fabrics with a variant polypeptide and/or composition as described above. The methods as described herein may be carried out by treating cellulose-containing fabrics during washing. However, if desired, treatment of the fabrics may also be carried out during soaking or rinsing or simply by adding the polypeptide and/or composition as described above to water in which the fabrics are or will be immersed.

In addition, a variant polypeptide and/or composition as described herein can also be used in antibacterial formulation as well as in pharmaceutical products such as throat lozenges, toothpastes, and mouthwash.

EXAMPLES

Experimental Information
Strains

WT 1: *Aspergillus niger* strain was deposited at the CENTRAAL BUREAU VOOR SCHIMMELCULTURES, Uppsalalaan 8, P.O. Box 85167, NL-3508 AD Utrecht, The Netherlands on 10 Aug. 1988 under the deposit number CBS 513.88.

WT 2: This *A. niger* strain is a WT 1 strain comprising a deletion of the gene encoding glucoamylase (glaA). WT 2 was constructed by using the "MARKER-GENE FREE" approach as described in EP0635574B1. In this patent it is extensively described how to delete glaA specific DNA sequences in the genome of CBS 513.88. The procedure resulted in a MARKER-GENE FREE ΔglaA recombinant *A. niger* CBS 513.88 strain, possessing finally no foreign DNA sequences at all.

WT 3: This *A. niger* strain is a WT 2 strain comprising a deletion of the pepA gene encoding the major extracellular aspartic protease PepA, as described by van den Hombergh et al. (van den Hombergh J P, Sollewijn Gelpke M D, van de Vondervoort P J, Buxton F P, Visser J. (1997)—Disruption of three acid proteases in *Aspergillus niger*—effects on protease spectrum, intracellular proteolysis, and degradation of target proteins—Eur J Biochem. 247(2): 605-13). The procedure resulted in a MARKER-GENE FREE WT 3 strain with the pepA gene inactivated in the WT 2 strain background.

Suitable *Rasamsonia* (*Talaromyces*) *emersonii* strains to show the effect and advantages as described herein are for example TEC-101, TEC-147, TEC-192, TEC-201 or TEC-210. They are described in WO 2011/000949. The "4E mix" or "4E composition" containing CBHI, CBHII, EG4 and BETA-GLUCOSIDASE (30 wt %, 25 wt %, 28 wt % and 8 wt %, respectively, wt % on dry matter protein) has been described in WO 2011/098577.

*Rasamsonia* (*Talaromyces*) *emersonii* strain TEC-101 (also designated as FBG 101) was deposited at CENTRAAL BUREAU VOOR SCHIMMELCULTURES, Uppsalalaan 8, P.O. Box 85167, NL-3508 AD Utrecht, The Netherlands on 30 Jun. 2010 having the Accession Number CBS 127450.
Molecular Biology Techniques In the above strains, using molecular biology techniques known to the skilled person (see: Sambrook & Russell, *Molecular Cloning: A Laboratory Manual*, 3rd Ed., CSHL Press, Cold Spring Harbor, N.Y., 2001), several genes are overexpressed and others are down regulated as described below. Examples of the general design of expression vectors for gene overexpression and disruption vectors for down-regulation, transformation, use of markers and selective media can be found in WO 1998/46772, WO 1999/32617, WO 2001/121779, WO 2005/095624, WO 2006/040312, EP0635574B, WO 2005/100573, WO 2011/009700, WO 2012/001169 and WO 2011/054899. All gene replacement vectors comprise approximately 1-2 kb flanking regions of the respective Open Reading Frame (ORF) sequences, to target for homologous recombination at the predestined genomic loci. In addition, *A. niger* vectors contain the *A. nidulans* bi-directional amdS selection marker for transformation, in between direct repeats. The method applied for gene deletion uses linear DNA, which integrates into the genome at the homologous locus of the flanking sequences by a double cross-over, thus substituting the gene to be deleted by the amdS gene. After transformation, the direct repeats allow for the removal of the selection marker by a (second) homologous recombination event. The removal of the amdS marker has been done by plating on fluoro-acetamide media, resulting in the selection of marker-gene-free strains. Using this strategy of transformation and subsequent counter-selection, which is also described as the "MARKER-GENE FREE" approach in EP 0 635 574. The amdS marker can be used indefinitely in strain modification programs.
Media and Solutions Potato dextrose agar, PDA, (Fluka, Cat. No. 70139): per litre: Potato extract 4 g; Dextrose 20 g; Bacto agar 15 g; pH 5.4; Sterilize 20 min at 120° C.

*Rasamsonia* agar medium: per litre: Salt fraction no. 3 15 g; Cellulose 30 g; Bacto peptone 7.5 g; Grain flour 15 g; $KH_2PO_4$ 5 g; $CaCl_2$).2 aq 1 g; Bacto agar 20 g; pH 6.0; Sterilize 20 min at 120° C.

Salt fraction composition: The "salt fraction no. 3" is fitting the disclosure of WO 98/37179, Table 1. Deviations from the composition of this table are $CaCl_2$).2 aq 1.0 g/l, KCl 1.8 g/L, citric acid 1 aq 0.45 g/L (chelating agent).

*Rasamsonia* shake flask medium 1: per litre: Glucose 20 g; Yeast extract (Difco) 20 g; Clerol FBA3107 (AF) 4 drops; MES 30 g; pH 6.0; Sterilize 20 min at 120° C.

*Rasamsonia* shake flask medium 2: per litre: Salt fraction no. 3 10 g; glucose 10 g; $KH_2PO_4$ 5 g; $NaH_2PO_4$ 2 g; $(NH_4)_2SO_4$ 5 g; MES 30 g; pH 5.4; Sterilize 20 min at 120° C.

*Rasamsonia* shake flask medium 3: per litre: Salt fraction no. 3 10 g; cellulose 20 g; $KH_2PO_4$ 5 g; $NaH_2PO_4$ 2 g; $(NH_4)_2SO_4$ 5 g; MES 30 g; pH 5.4; Sterilize 20 min at 120° C.

*Rasamsonia* shake flask medium 4: per litre: Salt fraction no. 3 10 g; cellulose 15 g; glucose 5 g; $KH_2PO_4$ 5 g; $NaH_2PO_4$ 2 g; $(NH_4)_2SO_4$ 5 g; MES 30 g; pH 5.4; Sterilize 20 min at 120° C.

Spore Batch Preparation for *Rasamsonia*

Strains were grown from stocks on *Rasamsonia* agar medium in 10 cm diameter Petri dishes for 5-7 days at 40° C. For MTP fermentations, strains were grown in 96-well plates containing *Rasamsonia* agar medium. Strain stocks are stored at −80° C. in 10% glycerol.

Chromosomal DNA Isolation

Strains were grown in YGG medium (per liter: 8 g KCl, 16 g glucose.$H_2O$, 20 ml of 10% yeast extract, 10 ml of 100× pen/strep, 6.66 g YNB+amino acids, 1.5 g citric acid, and 6 g $K_2HPO_4$) for 16 hours at 42° C., 250 rpm, and chromosomal DNA was isolated using the DNeasy plant mini kit (Qiagen, Hilden, Germany).

Shake Flask Growth Protocol of *Rasamsonia*

Spores were inoculated into 100 ml shake flasks containing 20 ml of *Rasamsonia* shake flask medium 1 and incubated at 45° C. at 250 rpm in an incubator shaker for 1 day (preculture 1) and 1 or 2 ml of biomass from preculture 1 was transferred to 100 ml shake flasks containing 20 ml of *Rasamsonia* shake flask medium 2 and grown under conditions as described above for 1 day (preculture 2). Subsequently, 1 or 2 ml of biomass from preculture 2 was transferred to 100 ml shake flasks containing 20 ml of *Rasamsonia* shake flask medium 3 or 4 and grown under conditions described above for 3 days.

Protein Analysis

Protein samples are separated under reducing conditions on NuPAGE 4-12% Bis-Tris gel (Invitrogen, Breda, The Netherlands) and stained. Gels are stained with either InstantBlue (Expedeon, Cambridge, United Kingdom), SimplyBlue safestain (Invitrogen, Breda, The Netherlands) or Sypro Ruby (Invitrogen, Breda, The Netherlands) according to manufacturer's instructions.

Total Protein Concentration Determination with TCA-Biuret Method

Concentrated protein samples (supernatants) were diluted with water to a concentration between 2 and 8 mg/ml. Bovine serum albumin (BSA) dilutions (0, 1, 2, 5, 8 and 10 mg/ml) were made and included as samples to generate a calibration curve. Of each diluted protein sample, 270 µl was transferred into a 10 ml tube containing 830 µl of a 12% (w/v) trichloro acetic acid solution in aceton and mixed thoroughly. Subsequently, the tubes were incubated on ice water for one hour and centrifuged for 30 minutes, at 4° C. and 6000 rpm. The supernatant was discarded and pellets were dried by inverting the tubes on a tissue and letting them stand for 30 minutes at room temperature. Next, 3 ml BioQuant Biuret reagent mix was added to the pellet in the tube and the pellet was solubilised upon mixing. Next, 1 ml water was added to the tube, the tube was mixed thoroughly and incubated at room temperature for 30 minutes. The absorption of the mixture was measured at 546 nm with a water sample used as a blank measurement and the protein concentration was calculated via the BSA calibration line.

Cellulase Activity Assays

In order to measure cellulase activity, corn stover activity assays are performed. Cellulase activity is measured in supernatants (the liquid part of the broth wherein the cells were cultured) of an empty strain and the transformant:

Preparation of Pretreated, Corn Stover Substrate.

Dilute-acid pre-treated corn stover is obtained as described in Schell, D. J., Applied Biochemistry and Biotechnology (2003), vol. 105-108, pp 69-85. A pilot scale pretreatment reactor is used operating at steady state conditions of 190° C., 1 min residence time and an effective $H_2SO_4$ acid concentration of 1.45% (w/w) in the liquid phase.

Assay 1: Microtiter Plate (MTP) 2% Unwashed Acid Pretreated Corn-Stover Sugar-Release Assay in which Supernatants are Spiked on Top of TEC-210 or 4E Mix For each (hemi-)cellulase assay, the stored samples are analyzed twice; 100 µL of sample (e.g. shake flask supernatant) and 100 µl of a (hemi-)cellulase base mix (3.5 mg/g DM TEC-210 or a 4 enzyme mix at a total dosage of 3.5 mg/g DM consisting of 0.3 mg/g DM BG (9% of total protein 4E mix), 1 mg/g DM CBHI (30% of total protein 4E mix), 0.9 mg/g DM CBHII (25% of total protein 4E mix) and 1.3 mg/g DM GH61 (36% of total protein 4E mix)) is transferred to two suitable vials: one vial containing 800 µL 2.5% (w/w) dry matter of the acid pretreated corn stover in a 50 mM citrate buffer, buffered at pH 4.5. The other vial consisted of a blank, where the 800 µL 2.5% (w/w) dry matter, acid pretreated corn stover is replaced by 800 µL 50 mM citrate buffer, buffered at pH 4.5. The assay samples are incubated for 72 hrs at 65° C. After incubation of the assay samples, a fixed volume of $D_2O$ (with 0.5 g/L DSS) containing an internal standard (maleic acid (20 g/L) and EDTA (40 g/L)) is added. The amount of sugar released, is based on the signal between 4.65-4.61 ppm, relative to DSS, and is determined by means of 1D 1H NMR operating at a proton frequency of 500 MHz, using a pulseprogram with water suppression, at a temperature of 27° C.

The (hemi)-cellulase enzyme solution may contain residual sugars. Therefore, the results of the assay are corrected for the sugar content measured after incubation of the enzyme solution.

Assay 2: Dose-Response 2% Unwashed Acid Pretreated Corn Stover Sugar Release Assay in MTP Since glucose release by cellulases is not a linear function of the quantity of enzyme in the composition, in other words, twice the amount of enzyme does not automatically result in twice the amount of glucose at a fixed time point. Therefore, the activity of the cellulose enzyme mixture is assessed in a dose response based assay, in which the dosage is based on equal amount of protein per cellulose mixture tested.

Overall cellulase activity of the mixture measured with unwashed acid pretreated corn stover as substrate. The frozen enzyme samples are thawed and a series of 6 dilutions is made ranging from undiluted in steps of two-fold up to 32-fold in 50 mM citrate buffer pH 4.5.

200 µl of sample is transferred to a vial containing 800 µL of 2.5% (w/w) dry matter of the acid pretreated corn stover in 50 mM citrate buffer, buffered at pH 4.5. Another 200 µl sample is transferred to a vial, referred to as blank, containing 800 µl of 50 mM citrate buffer, buffered at pH 4.5. In addition, a sugar background of corn stover is determined by incubating 800 µL 2.5% (w/w) dry matter of the acid pretreated corn stover in 50 mM citrate buffer, buffered at pH 4.5 with 200 µl of 50 mM citrate buffer. All vials are incubated for 72 hr at 65° C.

After incubation, 100 µl of internal standard solution (20 g/L maleic acid, 40 g/L EDTA in $D_2O$) is added to the vials. All vials containing pretreated corn stover are centrifuged for 30 minutes at 5300×g and, subsequently, 600 µl of the supernatant is transferred to a new vial containing 400 µl of $H_2O/D_2O$ 9:1.

The 1D $^1$H-NMR spectra are recorded on an Avance III Bruker operating at a proton frequency of 500 MHz, using a pulse program with water suppression, at a temperature of 27° C. Glucose quantification (arbitrary units) is performed based on the signal at 5.20 ppm, relative to 4,4-Dimethyl-4-silapentane sulfonic acid with relation to the internal standard signal at 6.30 ppm. The relative glucose release (ΔGlc) is calculated by correcting the glucose measured in the samples by the residual sugar present in the enzyme solution (measured from the blank) and the residual sugar present in the acid pretreated corn stover.

Since the protein concentration of the samples is known, the sugar release can be depicted as a function of protein mg/ml of the tested diluted sample versus the relative glucose release at time point 72 hours.

Beta-Glucosidase Basic Activity Assay

The beta-glucosidase activity of the variant polypeptides was analyzed in an MTP scale activity assay using p-nitrophenyl-β-D-glucopyranoside as substrate. *Rasamsonia emersonii* beta-glucosidase having the amino acid sequence of SEQ ID NO: 2 (wild-type/parent beta-glucosidase) was used as reference. In a total volume of 100 µl, the supernatants of the *A. niger* MTP fermentations expressing the variant polypeptides and the wild-type beta-glucosidase are incubated with 3 mM p-nitrophenyl-β-D-glucopyranoside in 50 mM acetate buffer pH 4.5 for 10 minutes at 60° C. After the incubation time, 100 µl of stop solution was added (1 M sodium carbonate) and the hydrolyzed free p-nitrophenol was determined by measuring the absorbance at 405 nm. As a blank, the substrate p-nitrophenyl-β-D-glucopyranoside was incubated in 100 µl 50 mM acetate buffer pH 4.5 at the same conditions (without enzyme) and the absorbance at 405 nm was determined after addition of the stop solution.

Beta-Glucosidase Glucose Inhibition Assay

A beta-glucosidase activity assay on cellobiose substrate was performed as described above on the *A. niger* strains expressing the variant polypeptides and the wild-type beta-glucosidase in the absence or presence of added glucose to test for glucose tolerance. All assays were performed in 500 µl reaction volume (50 mM citrate buffer, pH 4.5) of which 50 µl was a prediluted normalized beta-glucosidase enzyme sample. The amount of cellobiose substrate was 10 g/l, samples with added glucose were typically supplemeted with 20 g/l glucose, but this could range between 10 g/l and 200 g/l. After 20 minutes of incubation at 65° C., 100 µl of stop solution was added (1 M NaOH). The amount of cellobiose that was converted was measured by $^1$H-NMR. For each the variant polypeptides and for the wild-type beta-glucosidase, the ratio of the cellobiose conversion was determined in the absence and in the presence of added glucose. The ratio values were corrected for the level of substrate conversion. The corrected activity ratio values were used as indicators for glucose inhibition and the variant polypeptides with a more favourable glucose tolerance as compared to the beta-glucosidase having the amino acid sequence of SEQ ID NO: 2 (wild-type/parent beta-glucosidase) were considered to be more resistant against glucose inhibition.

Alternatively, the beta-glucosidase activity assay is performed as described in Example 2.

Example 1

Construction of *A. Niger* Expression Vectors and Expression of Variant Polypeptides This example describes the construction of an expression construct for overexpression of the variant polypeptides in *A. niger* and the expression of the variant polypeptides.

Construction of Expression Plasmids

The sequence of the wild-type polypeptide and a set of polypeptide variants as detailed below in Example 2 were synthesized as DNA fragments, subcloned, and sequence verified by sequence analysis. Subsequently, all variants were cloned into the pGBTOP vector (see FIG. 1 for general layout) using EcoRI and PacI sites, comprising the glucoamylase promoter and terminator sequence. The translational initiation sequence of the glucoamylase glaA promoter has been modified into 5'-CACCGTCAAA ATG-3' and an optimal translational termination sequence 5'-TAAA-3' was used in the generation of the expression construct (as also detailed in WO 2006/077258). The construction, general layout and use of such a vector is described in detail in WO 1999/32617. The *E. coli* part was removed by NotI digestion prior to transformation of *A. niger* WT 3.

Transformation of *A. Niger* and Shake Flask Fermentations

*A. niger* strain WT 3 was co-transformed with the pGBTOP expression constructs and pGBAAS-1 selection marker (but any appropriate selection marker—vide supra: amdS, hygromycin or phleomycin or alternative markers could be used) containing plasmid according to method described as described in for example WO 1999/32617 and WO 2011/009700 (and references therein), and selected on acetamide containing media and colony purified according to standard procedures, essentially as described in WO 98/46772 and WO 99/32617 and references therein and in the experimental information section herein. Strains containing the expression constructs were selected via PCR to verify presence of the pGBTOP expression cassette. Of recombinant strains containing the polynucleotide encoding the variant polypeptides and control *A. niger* strains, a large batch of spores was generated by plating spores or mycelia onto PDA plates (Potato Dextrose Agar, Oxoid), prepared according to manufacturer's instructions. After growth for 3-7 days at 30° C., spores were collected after adding 0.01% Triton X-100 to the plates. After washing with sterile water, about $10^7$ spores of selected transformants and control strains were inoculated into 100 ml shake flasks with baffles containing 20 ml of liquid preculture medium consisting of per liter: 30 g maltose.H$_2$O; 5 g yeast extract; 10 g hydrolyzed casein; 1 g KH$_2$PO$_4$; 0.5 g MgSO$_4$.7H$_2$O; 0.03 g ZnCl$_2$; 0.02 g CaCl$_2$); 0.01 g MnSO$_4$.4H$_2$O; 0.3 g FeSO$_4$.7H$_2$O; 3 g Tween 80; 10 ml penicillin (5000 IU/ml)/Streptomycin (5000 UG/ml); pH 5.5. These cultures were grown at 34° C. for 16-24 hours. 10 ml of this culture was inoculated into 500 ml shake flasks with baffles containing 100 ml fermentation medium consisting of per liter: 70 g glucose.H$_2$O; 25 g hydrolyzed casein; 12.5 g yeast extract; 1 g KH$_2$PO$_4$; 2 g K$_2$SO$_4$; 0.5 g MgSO$_4$.7H$_2$O; 0.03 g ZnCl$_2$; 0.02 g CaCl$_2$); 0.01 g MnSO$_4$.4H$_2$O; 0.3 g FeSO$_4$.7H$_2$O; 10 ml penicillin (5000 IU/ml)/Streptomycin (5000 UG/ml); adjusted to pH 5.6. These cultures were grown at 34° C. until all glucose was depleted (usually after 4-7 days). Samples taken from the fermentation broth were centrifuged (10 minutes at 5000×g) in a swinging bucket centrifuge and supernatants collected and filtered over a 0.2 µm filter (Nalgene).

Supernatants were analysed for expression of the variant polypeptides by SDS-PAGE and total protein measurements. *A. niger* supernatants containing the variant polypeptides are spiked on top of TEC-210 or 4E-mix and analysed in a corn stover activity assay. Spiking of supernatant of the variant polypeptides shows increased hydrolysis of corn stover compared to controls in which the supernatant of the variant polypeptides as described herein is not spiked in. The supernatants were subjected to a MTP scale activity assay as described in Example 2 and a large scale activity assay as described in Example 3 to identify variant polypeptides that are less sensitive to glucose inhibition than the parent polypeptide.

Example 2

Identification of Variant Polypeptides with a Higher Glucose Tolerance in MTP Scale All variant polypeptides were expressed in *A. niger* and grown in a shakeflask culture. The beta-glucosidase activity of the variant polypeptides was analyzed in an MTP scale activity assay using 3 mM p-nitrophenyl-β-D-glucopyranoside as substrate. *Rasamsonia emersonii* beta-glucosidase having the amino acid sequence of SEQ ID NO: 2 (wild-type/parent beta-glucosidase) was used as reference. Typically, 50 μl of pre-diluted *A. niger* shakeflask fermentation material was incubated with 50 μl 6 mM p-nitrophenyl-β-D-glucopyranoside substrate solution in 100 mM sodium acetate buffer at pH 4.5 and at a temperature of 60°. The dilution of the fermentation material was chosen to allow an absorbance measurement at 405 nm in the linear range of the 4-nitrophenol standard calibration curve. The incubation time of the supernatant and the substrate was 15 minutes. After 15 minutes, the hydrolysis conversion was stopped by addition of 100 μl 1 M sodium carbonate stop solution and the hydrolyzed free p-nitrophenol was determined by measuring the absorbance at 405 nm. As a blank, the substrate p-nitrophenyl-β-D-glucopyranoside was incubated in 100 μl 50 mM acetate buffer pH 4.5 at the same conditions (without enzyme) and the absorbance at 405 nm was determined after addition of the stop solution. For each fermentation sample, the catalytic activity was determined based on the amount of 4-nitrophenol that was formed during the incubation per mg of protein present in the incubation. The concentration of 4-nitrophenol formed, was determined by measuring the absorbance at 405 nm at basic pH and calculating the concentration via the 4-nitrophenol standard calibration curve. Activity values per mg of protein were used for normalizing the variant polypeptides to the same activity value, which allowed activity measurements within the detection limit for the follow-up experiment.

For the follow-up experiment, five dilutions were made: 2-fold, 4-fold, 8-fold, 16-fold and 32-fold. The beta-glucosidase activity of the variant polypeptides and the wild-type beta-glucosidase was further analyzed in a MTP scale activity assay using cellobiose as substrate and monitoring cellobiose hydrolysis via glucose formation with NMR of the undiluted sample and the five dilutions. The same assay was performed for all dilutions in presence of 20 g/l glucose to determine the glucose tolerance. In a total volume of 500 μl, 50 μl of the diluted supernatants of the *A. niger* MTP fermentations expressing the variant polypeptides or the wild-type beta-glucosidase were incubated with 10 g/l cellobiose with and without the addition of 20 g/l glucose in 50 mM citrate buffer pH 4.5 for 20 minutes at 65° C. Measurements (with and without 20 g/l glucose) were performed for the variant polypeptides and the wild-type beta-glucosidase. After the incubation time of 20 minutes, 50 μl of a 14 M sodium hydroxide solution was added to stop the reaction via a sudden increase of the pH. Subsequently, cellobiose and glucose levels in the samples were analyzed with NMR.

After enzymatic incubation, 100 μl of internal standard solution containing 20 g/l maleic acid and EDTA (40 g/L) in demineralized water, was added to each sample. Subsequently, the samples were lyophilized overnight. The dried residue was dissolved in 600 μL of $D_2O$ (with 0.5 g/l DSS (4,4-dimethyl-4-silapentane-1-sulfonic acid)). 1D $^1H$ NMR spectra were recorded on a Bruker Avance III HD 500 MHz, equipped with a He cooled cryo-probe, using a pulse program without water suppression at a temperature of 29° C. with a 90 degrees excitation pulse, acquisition time of 2.7 s and relaxation delay of 30 s. The analyte concentrations (in g/L) were calculated based on the following signals (δ relative to DSS): Cellobiose: H1' cellobiose peak at 4.50 ppm (d, 1H, J=8 Hz); Glucose: α-H1 glucose/α-H1 cellobiose peak at 5.22 ppm (d, 0.38 H, J=4 Hz). The glucose concentration was determined after correction for cellobiose. The signal user for the standard: Maleic acid peak at 6.0 ppm (s, 2H). As the enzyme solutions may contain residual sugars, glucose results were corrected for the sugar content measured after incubation of the enzyme solution. In addition, a negative control was included; the cellobiose solution without added enzyme was incubated at the same conditions and the cellobiose level was determined with NMR (no cellobiose hydrolysis should occur).

Next, the variant polypeptides with reduced glucose inhibition were selected. The kinetics of the variants and the wild-type beta-glucosidase were studied by measuring the cellobiose to glucose conversion via NMR after a 20 minute incubation at 6 variant concentrations in presence and absence of initial glucose (20 g/L) as described above. In total 12 experiments were performed per enzyme variant (six dilutions, with and without glucose). A computational model was applied to extract information about the kinetics of the vatriants from the obtained glucose and cellobiose concentrations. The model was defined as follows:

BG activity was modeled as irreversible Michaelis-Menten kinetics with competitive glucose inhibition:

$$rateBG = \frac{kcat[E][\text{cellobiose}]}{\text{cellobiose} + K_M\left(1 + \frac{\text{glucose}}{Ki}\right)}$$

The coupled ordinary differential equations that describe the reaction are:

$$\frac{d[\text{cellobiose}]}{dt} = -rateBG$$

$$\frac{d[\text{glucose}]}{dt} = +1.053\ rateBG$$

The concentration of cellobiose and glucose was defined in the units: g/L. The ordinary differential equations were solved numerically using ODE15s solver of MATLAB (the Mathworks, Inc., version 2012A), default options of the solver settings were used. The initial conditions for glucose cellobiose and enzyme concentrations were set according to the experimental conditions. For each variant the following analysis was applied:

simulations were performed to predict the cellobiose to glucose conversion for each of the 12 experimental conditions. The difference between model predictions and experimental data was minimized by estimating the values of kcat and $K_i$ ($K_m$ was set to 0.1 g/L). To this end, nonlinear least square regression (MATLAB function lsqnonlin) was applied. As objective function, minimization of the difference between predicted and measured cellobiose and glucose concentrations was used. Default settings of lsqnonlin were used except the option 'DiffMinChange', which was set to 0.01.

Selection of mutants with improved kinetic properties was based on the estimated $K_i$ and kcat values. The higher the value of Ki, the higher the glucose tolerance (the lower the inhibition). The higher the value of kcat, the faster is the variant: faster conversion of cellobiose into glucose. The kinetic parameters Ki and kcat were calculated as unitless parameters. The results are shown in Table 1.

The results demonstrate that variant polypeptide 3 is less sensitive to glucose inhibition than its parent polypeptide (the wild-type beta-glucosidase), as the value for Ki is higher (3.2 vs 1.7). The results further demonstrate that variant polypeptide 1 is less sensitive to glucose inhibition than its parent polypeptide (the wild-type beta-glucosidase), as the value for Ki is higher (2.7 vs 1.7). The results demonstrate that variant polypeptide 2 is less sensitive to glucose inhibition than its parent polypeptide (the wild-type beta-glucosidase), as the value for Ki is higher (2.6 vs 1.7). The results demonstrate that variant polypeptide 4 has improved kinetic properties (works faster) than its parent polypeptide (the wild-type beta-glucosidase), as the value for kcat is higher (2.7 vs 1.0).

Example 3

Identification of Variant Polypeptides with a Higher Glucose Tolerance at 100 ml Scale The hits selected from the MTP scale assay were subsequently further characterized by monitoring cellobiose conversion at multiple time points at a larger scale. The beta-glucosidase having the amino acid sequence of SEQ ID NO: 2 was used as reference (parent/wild-type beta-glucosidase). The assay was done as follows: the variant polypeptides and the reference beta-glucosidase were incubated at a concentration of 4.5 µg/ml in a 100 mM NaAc-buffer pH 4.5 with 30 mM cellobiose in a final volume of 100 ml for 2 hours at 62° C. under continuous stirring. Samples of 1 ml were taken at t=0 and after t=5 min, t=10 min, t=15 min, t=30 min, t=45 min, t=60 min, t=90 min, t=120 min and t=360 min and incubated for 5 minutes at 99° C. to stop the reaction. The glucose and cellobiose content of the samples was determined using a High-Performance Liquid Chromatography System (Agilent 1100) equipped with a refection index detector (Agilent 1260 Infinity). The separation of the sugars was achieved by using a 300×7.8 mm Aminex HPX-87P (Bio rad) column; Pre-column: Micro guard Carbo-P (Bio Rad); mobile phase was HPLC grade water; flow rate of 0.6 ml/min and a column temperature of 85° C. The injection volume was 10 µl. The samples were diluted with HPLC grade water to a maximum of 2.5 g/l glucose and filtered by using 0.2 µm filter (Afridisc LC25 mm syringe filter PVDF membrane). The glucose and cellobiose were identified and quantified according to the retention time, which was compared to the external glucose and cellobiose standards ranging from 0.2; 0.4; 1.0; 2.0 g/l.

The concentration cellobiose was plotted against time and the linear part of this curve (the linear part of the cellobiose hydrolysis) was used to calculate the V0 (the initial rate of cellobiose hydrolysis) in the presence and absence of 20 g/l glucose. The ratio of these two calculated rates (V0 in presence of glucose/V0 in absence of glucose) was calculated for the wild-type beta-glucosidase and the variant polypeptides and is listed in Table 2. Variant polypeptides with a higher ratio (V0 in presence of glucose/V0 in absence of glucose) than the wild-type beta-glucosidase have a higher tolerance against glucose (i.e. are less sensitive to glucose inhibition).

The results demonstrate that variant polypeptide 3 is less sensitive to glucose inhibition than its parent polypeptide (the wild-type beta-glucosidase), as the ratio V0 in presence of glucose/V0 in absence of glucose is higher (0.29 vs 0.18). The results further demonstrate that variant polypeptide 1 is less sensitive to glucose inhibition than its parent polypeptide (the wild-type beta-glucosidase), as the ratio V0 in presence of glucose/V0 in absence of glucose is higher (0.21 vs 0.18). The results further demonstrate that variant polypeptide 2 is less sensitive to glucose inhibition than its parent polypeptide (the wild-type beta-glucosidase), as the ratio V0 in presence of glucose/V0 in absence of glucose is higher (0.21 vs 0.18).

TABLE 1

Model prediction of Ki and kcat of variant polypeptides.

| Polypeptide | Model prediction Ki (unitless) | Model prediction kcat (unitless) |
|---|---|---|
| Wild-type beta-glucosidase (SEQ ID NO: 2) | 1.7 | 1.0 |
| Variant polypeptide 1 (SEQ ID NO: 2 with substitutions M90L + M335V + M485I) | 2.7 | 0.9 |
| Variant polypeptide 2 (SEQ ID NO: 2 with substitution N103A) | 2.6 | 1.1 |
| Variant polypeptide 3 (SEQ ID NO: 2 with substitution G142S) | 3.2 | 0.8 |
| Variant polypeptide 4 (SEQ ID NO: 2 with substitution L606A) | 1.1 | 2.7 |

TABLE 2

Ratio V0 in presence of glucose and V0 in absence of glucose of variant polypeptides.

| Polypeptide | V0 (µmol/ml · min) 0 g/l glucose | V0 (µmol/ml · min) 20 g/l glucose | Ratio (V0 in presence of glucose/V0 in absence of glucose) |
|---|---|---|---|
| Wild-type beta-glucosidase (SEQ ID NO: 2) | 0.52 | 0.09 | 0.18 |
| Variant polypeptide 1 (SEQ ID NO: 2 with substitutions M90L + M335V + M485I) | 0.72 | 0.15 | 0.21 |
| Variant polypeptide 2 (SEQ ID NO: 2 with substitution N103A) | 0.66 | 0.14 | 0.21 |
| Variant polypeptide 3 (SEQ ID NO: 2 with substitution G142S) | 0.55 | 0.16 | 0.29 |

The invention claimed is:

1. A variant polypeptide comprising substitution G142S at a position corresponding to position 142 of the polypeptide of SEQ ID NO:2, wherein the variant polypeptide has beta-glucosidase activity and at least 90% sequence identity to the polypeptide of SEQ ID NO:2.

2. The variant polypeptide according to claim 1, which further comprises at least one substitution at a position of the polypeptide of SEQ ID NO:2 selected from positions 90, 103, 335, 485, 606, and any combination thereof.

3. The variant polypeptide according to claim 1, wherein the variant polypeptide is less sensitive to glucose inhibition than the polypeptide of SEQ ID NO:2.

4. A composition comprising:
   (i) the variant polypeptide according to claim 1, and
   (ii) a cellulase and/or a hemicellulase and/or a pectinase.

5. The composition according to claim 4, wherein the cellulase is selected from the group consisting of a lytic polysaccharide monooxygenase, a cellobiohydrolase I, a cellobiohydrolase II, an endo-beta-1,4-glucanase, a beta-glucosidase and a beta-(1,3)(1,4)-glucanase or any combination thereof and the hemicellulase is selected from the group consisting of an endoxylanase, a beta-xylosidase, an alpha-L-arabinofuranosidase, an alpha-D-glucuronidase, an acetyl-xylan esterase, a feruloyl esterase, a coumaroyl esterase, an alpha-galactosidase, a beta-galactosidase, a beta-mannanase, a beta-mannosidase or any combination thereof.

6. The composition according to claim 4, wherein the composition is a whole fermentation broth.

7. A method for the treatment of a substrate comprising cellulose and/or hemicellulose which method comprises contacting the substrate with
   (i) the variant polypeptide according to claim 1 or
   (ii) a composition comprising the variant polypeptide according to claim 1, and a cellulase and/or a hemicellulase and/or a pectinase.

8. A method of producing a fermentation product, which method comprises:
   a) treating a substrate using the method according to claim 7 to produce a material, and
   b) fermenting the resulting material to produce the fermentation product.

* * * * *